US008267858B2

(12) United States Patent
Albrecht et al.

(10) Patent No.: US 8,267,858 B2
(45) Date of Patent: Sep. 18, 2012

(54) WOUND RETRACTOR WITH GEL CAP

(75) Inventors: Jeremy J. Albrecht, Rancho Santa Margarita, CA (US); Charles C. Hart, Summerville, SC (US); John R. Brustad, Dana Point, CA (US); Gary M. Johnson, Mission Viejo, CA (US); Jennifer T. Ko, Vista, CA (US); Donald L. Gadberry, Capistrano Beach, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 60 days.

(21) Appl. No.: 13/008,728

(22) Filed: Jan. 18, 2011

(65) Prior Publication Data

US 2011/0172493 A1 Jul. 14, 2011

Related U.S. Application Data

(63) Continuation of application No. 12/791,666, filed on Jun. 1, 2010, now Pat. No. 7,883,461, which is a continuation of application No. 11/548,781, filed on Oct. 12, 2006, now Pat. No. 7,727,146.

(60) Provisional application No. 60/828,089, filed on Oct. 4, 2006, provisional application No. 60/803,965, filed on Jun. 5, 2006, provisional application No. 60/803,346, filed on May 26, 2006, provisional application No. 60/745,730, filed on Apr. 26, 2006, provisional application No. 60/726,826, filed on Oct. 14, 2005.

(51) Int. Cl.
*A61B 1/32* (2006.01)

(52) U.S. Cl. ......... 600/208; 600/201; 600/203; 600/206

(58) Field of Classification Search .......... 600/201–246; 128/846, 856; 606/119
See application file for complete search history.

(56) References Cited

U.S. PATENT DOCUMENTS

| 558,364 A | 4/1896 | Doolittle |
| 1,157,202 A | 10/1915 | Bates et al. |

(Continued)

FOREIGN PATENT DOCUMENTS

DE 26 05 148 A1 8/1977

(Continued)

OTHER PUBLICATIONS

US 5,344,646, Chen (withdrawn).

(Continued)

*Primary Examiner* — Eduardo C Robert
*Assistant Examiner* — Christina Negrelli
(74) *Attorney, Agent, or Firm* — Cynthia A. Bonner

(57) ABSTRACT

An incrementally adjustable wound retractor, which provides access to a body cavity, includes an inner ring having a diameter greater than the desired diameter of the wound incision, an outer ring having an annular axis and a diameter greater than the desired diameter of the wound incision, and a flexible sleeve disposed in a generally cylindrical form between the inner and outer rings. The outer ring includes first and second circular tubes spaced apart axially with each including a lumen having a rigid, noncompliant split hoop positioned therein. The outer ring may be rolled over itself and around the annular axis to retract the sleeve with sufficient force to stretch the incision to the desired diameter. A gel cap seal may be coupled to the outer ring outside of the biological body to seal the opening produced by the wound retractor between the body cavity and outside the body cavity.

16 Claims, 78 Drawing Sheets

U.S. PATENT DOCUMENTS

| | | | |
|---|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | M. Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds, Jr. et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |

| | | |
|---|---|---|
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Ritchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |

| | | | | | |
|---|---|---|---|---|---|
| 5,634,936 A | 6/1997 | Linden et al. | 5,913,847 A | 6/1999 | Yoon |
| 5,634,937 A | 6/1997 | Mollenauer et al. | 5,916,198 A | 6/1999 | Dillow |
| 5,636,645 A | 6/1997 | Ou | 5,916,232 A | 6/1999 | Hart |
| 5,640,977 A | 6/1997 | Leahy et al. | 5,919,476 A | 7/1999 | Fischer et al. |
| 5,643,301 A | 7/1997 | Mollenauer | 5,931,832 A | 8/1999 | Jensen |
| 5,649,550 A | 7/1997 | Crook | 5,947,922 A | 9/1999 | MacLeod |
| 5,651,771 A | 7/1997 | Tangherlini et al. | 5,951,467 A | 9/1999 | Picha et al. |
| 5,653,705 A | 8/1997 | de la Torre et al. | 5,951,588 A | 9/1999 | Moenning |
| 5,657,963 A | 8/1997 | Hinchliffe et al. | 5,957,888 A | 9/1999 | Hinchliffe |
| 5,658,272 A | 8/1997 | Hasson | 5,957,913 A | 9/1999 | de la Torre |
| 5,658,306 A | 8/1997 | Kieturakis | 5,962,572 A | 10/1999 | Chen |
| 5,662,615 A | 9/1997 | Blake, III | 5,964,781 A | 10/1999 | Mollenauer et al. |
| 5,672,168 A | 9/1997 | de la Torre et al. | 5,976,174 A | 11/1999 | Ruiz |
| 5,681,341 A | 10/1997 | Lunsford et al. | 5,989,232 A | 11/1999 | Yoon |
| 5,683,378 A | 11/1997 | Christy | 5,989,233 A | 11/1999 | Yoon |
| 5,685,854 A | 11/1997 | Green et al. | 5,989,266 A | 11/1999 | Foster |
| 5,685,857 A | 11/1997 | Negus et al. | 5,993,471 A | 11/1999 | Riza et al. |
| 5,697,914 A | 12/1997 | Brimhall | 5,993,485 A | 11/1999 | Beckers |
| 5,707,703 A | 1/1998 | Rothrum et al. | 5,994,450 A | 11/1999 | Pearce |
| 5,709,664 A | 1/1998 | Vandenbroek et al. | 5,997,515 A | 12/1999 | de la Torre et al. |
| 5,713,858 A | 2/1998 | Heruth et al. | 6,004,303 A | 12/1999 | Peterson |
| 5,713,869 A | 2/1998 | Morejon | 6,010,494 A | 1/2000 | Schafer et al. |
| 5,720,730 A | 2/1998 | Blake, III | 6,017,355 A | 1/2000 | Hessel et al. |
| 5,725,536 A | 3/1998 | Oberlin et al. | 6,018,094 A | 1/2000 | Fox |
| 5,728,103 A | 3/1998 | Picha et al. | 6,024,736 A | 2/2000 | de la Torre et al. |
| 5,730,748 A | 3/1998 | Fogarty et al. | 6,025,067 A | 2/2000 | Fay |
| 5,735,791 A | 4/1998 | Alexander et al. | 6,033,426 A | 3/2000 | Kaji |
| 5,738,628 A | 4/1998 | Sierocuk et al. | 6,033,428 A | 3/2000 | Sardella |
| 5,741,234 A | 4/1998 | Aboul-Hosn | 6,035,559 A | 3/2000 | Freed et al. |
| 5,741,298 A | 4/1998 | MacLeod | 6,042,573 A | 3/2000 | Lucey |
| 5,743,884 A | 4/1998 | Hasson et al. | 6,045,535 A | 4/2000 | Ben Nun |
| 5,749,882 A | 5/1998 | Hart et al. | 6,048,309 A | 4/2000 | Flom et al. |
| 5,753,150 A | 5/1998 | Martin et al. | 6,050,871 A | 4/2000 | Chen |
| 5,755,660 A | 5/1998 | Tyagi | 6,053,934 A | 4/2000 | Andrews et al. |
| 5,760,117 A | 6/1998 | Chen | 6,059,816 A | 5/2000 | Moenning |
| 5,769,783 A | 6/1998 | Fowler | 6,066,117 A | 5/2000 | Fox et al. |
| 5,782,812 A | 7/1998 | Hart et al. | 6,068,639 A | 5/2000 | Fogarty et al. |
| 5,782,817 A | 7/1998 | Franzel et al. | 6,077,288 A | 6/2000 | Shimomura et al. |
| 5,782,859 A | 7/1998 | Nicholas et al. | 6,086,603 A | 7/2000 | Termin et al. |
| 5,788,676 A | 8/1998 | Yoon | 6,090,043 A | 7/2000 | Austin et al. |
| 5,792,119 A | 8/1998 | Marx | 6,099,506 A | 8/2000 | Macoviak et al. |
| 5,795,290 A | 8/1998 | Bridges | 6,110,154 A | 8/2000 | Shimomura et al. |
| 5,803,919 A | 9/1998 | Hart et al. | 6,123,689 A | 9/2000 | To et al. |
| 5,803,921 A | 9/1998 | Bonadio | 6,142,935 A | 11/2000 | Flom et al. |
| 5,803,923 A | 9/1998 | Singh-Derewa et al. | 6,142,936 A | 11/2000 | Beane et al. |
| 5,807,350 A | 9/1998 | Diaz | 6,149,642 A | 11/2000 | Gerhart et al. |
| 5,810,712 A | 9/1998 | Dunn | 6,150,608 A | 11/2000 | Wambeke et al. |
| 5,810,721 A | 9/1998 | Mueller et al. | 6,159,182 A | 12/2000 | Davis et al. |
| 5,813,409 A | 9/1998 | Leahy et al. | 6,162,172 A | 12/2000 | Cosgrove et al. |
| 5,814,026 A | 9/1998 | Yoon | 6,162,196 A | 12/2000 | Hart et al. |
| 5,817,062 A | 10/1998 | Flom et al. | 6,162,206 A | 12/2000 | Bindokas |
| 5,819,375 A | 10/1998 | Kastner | 6,163,949 A | 12/2000 | Neuenschwander |
| 5,820,555 A | 10/1998 | Watkins, III et al. | 6,164,279 A | 12/2000 | Tweedle |
| 5,820,600 A | 10/1998 | Carlson et al. | 6,171,282 B1 | 1/2001 | Ragsdale |
| 5,830,191 A | 11/1998 | Hildwein et al. | 6,183,486 B1 | 2/2001 | Snow et al. |
| 5,832,925 A | 11/1998 | Rothrum | 6,197,002 B1 | 3/2001 | Peterson |
| 5,836,871 A | 11/1998 | Wallace et al. | 6,217,555 B1 | 4/2001 | Hart et al. |
| 5,841,298 A | 11/1998 | Huang | 6,217,590 B1 | 4/2001 | Levinson |
| 5,842,971 A | 12/1998 | Yoon | 6,224,612 B1 | 5/2001 | Bates |
| 5,848,992 A | 12/1998 | Hart et al. | 6,228,063 B1 | 5/2001 | Aboul-Hosn |
| 5,853,395 A | 12/1998 | Crook et al. | 6,238,373 B1 | 5/2001 | de la Torre |
| 5,853,417 A | 12/1998 | Fogarty et al. | 6,241,768 B1 | 6/2001 | Agarwal et al. |
| 5,857,461 A | 1/1999 | Levitsky et al. | 6,254,533 B1 | 7/2001 | Fadem et al. |
| 5,860,995 A | 1/1999 | Berkelaar | 6,254,534 B1 | 7/2001 | Butler et al. |
| 5,865,728 A | 2/1999 | Moll et al. | 6,258,065 B1 | 7/2001 | Dennis et al. |
| 5,865,729 A | 2/1999 | Meehan et al. | 6,264,604 B1 | 7/2001 | Kieturakis et al. |
| 5,865,807 A | 2/1999 | Blake, III | 6,267,751 B1 | 7/2001 | Mangosong |
| 5,865,817 A | 2/1999 | Moenning et al. | 6,276,661 B1 | 8/2001 | Laird |
| 5,871,474 A | 2/1999 | Hermann et al. | 6,287,280 B1 | 9/2001 | Lampropoulos |
| 5,876,413 A | 3/1999 | Fogarty et al. | 6,315,770 B1 | 11/2001 | de la Torre et al. |
| 5,879,368 A | 3/1999 | Hoskin et al. | 6,319,246 B1 | 11/2001 | de la Torre |
| 5,882,344 A | 3/1999 | Stouder, Jr. | 6,322,541 B2 | 11/2001 | West et al. |
| 5,884,639 A | 3/1999 | Chen | 6,325,384 B1 | 12/2001 | Berry, Sr. et al. |
| 5,894,843 A | 4/1999 | Benetti et al. | 6,346,074 B1 | 2/2002 | Roth |
| 5,895,377 A | 4/1999 | Smith et al. | 6,371,968 B1 | 4/2002 | Kogasaka et al. |
| 5,899,208 A | 5/1999 | Bonadio | 6,382,211 B1 | 5/2002 | Crook |
| 5,899,913 A | 5/1999 | Fogarty et al. | 6,383,162 B1 | 5/2002 | Sugarbaker |
| 5,904,703 A | 5/1999 | Gilson | 6,391,043 B1 | 5/2002 | Moll et al. |
| 5,906,577 A | 5/1999 | Beane et al. | 6,413,244 B1 | 7/2002 | Bestetti et al. |

| | | | | | | |
|---|---|---|---|---|---|---|
| 6,413,458 B1 | 7/2002 | Pearce | | 6,945,932 B1 | 9/2005 | Caldwell et al. |
| 6,420,475 B1 | 7/2002 | Chen | | 6,949,893 B2 | 9/2005 | Higuchi |
| 6,423,036 B1 | 7/2002 | Van Huizen | | 6,958,037 B2 | 10/2005 | Ewers et al. |
| 6,440,061 B1 | 8/2002 | Wenner et al. | | 6,972,026 B1 | 12/2005 | Caldwell et al. |
| 6,440,063 B1 | 8/2002 | Beane et al. | | 6,979,324 B2 | 12/2005 | Bybordi et al. |
| 6,443,957 B1 | 9/2002 | Addis | | 6,991,602 B2 | 1/2006 | Nakazawa et al. |
| 6,447,489 B1 | 9/2002 | Peterson | | 6,997,909 B2 | 2/2006 | Goldberg |
| 6,450,983 B1 | 9/2002 | Rambo | | 7,001,397 B2 | 2/2006 | Davison et al. |
| 6,454,783 B1 | 9/2002 | Piskun | | 7,008,377 B2 | 3/2006 | Beane et al. |
| 6,464,686 B1 | 10/2002 | O'Hara et al. | | 7,014,628 B2 | 3/2006 | Bousquet |
| 6,468,292 B1 | 10/2002 | Mollenauer et al. | | 7,033,319 B2 | 4/2006 | Pulford et al. |
| 6,482,181 B1 | 11/2002 | Racenet et al. | | 7,052,454 B2 | 5/2006 | Taylor |
| 6,485,435 B1 | 11/2002 | Bakal | | 7,056,304 B2 | 6/2006 | Bacher et al. |
| 6,485,467 B1 | 11/2002 | Crook et al. | | 7,056,321 B2 | 6/2006 | Pagliuca et al. |
| 6,488,620 B1 | 12/2002 | Segermark et al. | | 7,067,583 B2 | 6/2006 | Chen |
| 6,488,692 B1 | 12/2002 | Spence et al. | | 7,077,852 B2 | 7/2006 | Fogarty et al. |
| 6,494,893 B2 | 12/2002 | Dubrul et al. | | 7,081,089 B2 | 7/2006 | Bonadio et al. |
| 6,527,787 B1 | 3/2003 | Fogarty et al. | | 7,083,626 B2 | 8/2006 | Hart et al. |
| 6,533,734 B1 | 3/2003 | Corley, III et al. | | 7,093,599 B2 | 8/2006 | Chen |
| 6,551,270 B1 | 4/2003 | Bimbo et al. | | 7,100,614 B2 | 9/2006 | Stevens et al. |
| 6,551,276 B1 | 4/2003 | Mann et al. | | 7,101,353 B2 | 9/2006 | Lui et al. |
| 6,551,344 B2 | 4/2003 | Thill | | 7,105,009 B2 | 9/2006 | Johnson |
| 6,552,109 B1 | 4/2003 | Chen | | 7,105,607 B2 | 9/2006 | Chen |
| 6,554,793 B1 | 4/2003 | Pauker et al. | | 7,112,185 B2 | 9/2006 | Hart et al. |
| 6,558,371 B2 | 5/2003 | Dorn | | 7,118,528 B1 | 10/2006 | Piskun |
| 6,569,120 B1 | 5/2003 | Green et al. | | 7,134,929 B2 | 11/2006 | Chen |
| 6,578,577 B2 | 6/2003 | Bonadio et al. | | 7,153,261 B2 | 12/2006 | Wenchell |
| 6,579,281 B2 | 6/2003 | Palmer et al. | | 7,163,510 B2 | 1/2007 | Kahle et al. |
| 6,582,364 B2 | 6/2003 | Butler et al. | | 7,192,436 B2 | 3/2007 | Sing et al. |
| 6,589,167 B1 | 7/2003 | Shimomura et al. | | 7,193,002 B2 | 3/2007 | Chen |
| 6,589,211 B1 | 7/2003 | MacLeod | | 7,195,590 B2 | 3/2007 | Butler et al. |
| 6,607,504 B2 | 8/2003 | Haarala et al. | | 7,214,185 B1 | 5/2007 | Rosney et al. |
| 6,613,952 B2 | 9/2003 | Rambo | | 7,217,277 B2 | 5/2007 | Parihar et al. |
| 6,623,426 B2 | 9/2003 | Bonadio et al. | | 7,222,380 B2 | 5/2007 | Chen |
| 6,627,275 B1 | 9/2003 | Chen | | 7,223,257 B2 | 5/2007 | Shubayev et al. |
| 6,663,598 B1 | 12/2003 | Carrillo et al. | | 7,223,278 B2 | 5/2007 | Davison et al. |
| 6,669,674 B1 | 12/2003 | Macoviak et al. | | 7,226,484 B2 | 6/2007 | Chen |
| 6,676,639 B1 | 1/2004 | Ternström | | 7,235,062 B2 | 6/2007 | Brustad |
| 6,702,787 B2 | 3/2004 | Racenet et al. | | 7,235,084 B2 | 6/2007 | Skakoon et al. |
| 6,705,989 B2 | 3/2004 | Cuschieri et al. | | 7,238,154 B2 | 7/2007 | Ewers et al. |
| 6,706,050 B1 | 3/2004 | Giannadakis | | 7,244,244 B2 | 7/2007 | Racenet et al. |
| 6,714,298 B2 | 3/2004 | Ryer | | 7,276,075 B1 | 10/2007 | Callas et al. |
| 6,716,201 B2 | 4/2004 | Blanco | | 7,290,367 B2 | 11/2007 | Chen |
| 6,723,044 B2 | 4/2004 | Pulford et al. | | 7,294,103 B2 | 11/2007 | Bertolero et al. |
| 6,723,088 B2 | 4/2004 | Gaskill, III et al. | | 7,297,106 B2 | 11/2007 | Yamada et al. |
| 6,725,080 B2 | 4/2004 | Melkent et al. | | 7,300,399 B2 | 11/2007 | Bonadio et al. |
| 6,793,621 B2 | 9/2004 | Butler et al. | | 7,316,699 B2 | 1/2008 | McFarlane |
| 6,794,440 B2 | 9/2004 | Chen | | 7,331,940 B2 | 2/2008 | Sommerich |
| 6,796,940 B2 | 9/2004 | Bonadio et al. | | 7,338,473 B2 | 3/2008 | Campbell et al. |
| 6,797,765 B2 | 9/2004 | Pearce | | 7,344,547 B2 | 3/2008 | Piskun |
| 6,800,084 B2 | 10/2004 | Davison et al. | | 7,344,568 B2 | 3/2008 | Chen |
| 6,811,546 B1 | 11/2004 | Callas et al. | | 7,377,898 B2 | 5/2008 | Ewers et al. |
| 6,814,078 B2 | 11/2004 | Crook | | 7,390,317 B2 | 6/2008 | Taylor et al. |
| 6,814,700 B1 | 11/2004 | Mueller et al. | | 7,393,322 B2 | 7/2008 | Wenchell |
| 6,817,974 B2 | 11/2004 | Cooper et al. | | 7,412,977 B2 | 8/2008 | Fields et al. |
| 6,830,578 B2 | 12/2004 | O'Heeron et al. | | 7,445,597 B2 | 11/2008 | Butler et al. |
| 6,837,893 B2 | 1/2005 | Miller | | 7,473,221 B2 | 1/2009 | Ewers et al. |
| 6,840,946 B2 | 1/2005 | Fogarty et al. | | 7,481,765 B2 | 1/2009 | Ewers et al. |
| 6,840,951 B2 | 1/2005 | de la Torre et al. | | 7,537,564 B2 | 5/2009 | Bonadio et al. |
| 6,846,287 B2 | 1/2005 | Bonadio et al. | | 7,540,839 B2 | 6/2009 | Butler et al. |
| 6,860,463 B2 | 3/2005 | Hartley | | 7,559,893 B2 | 7/2009 | Bonadio et al. |
| 6,863,674 B2 | 3/2005 | Kasahara et al. | | 7,578,832 B2 | 8/2009 | Johnson |
| 6,866,861 B1 | 3/2005 | Luhman | | 7,645,232 B2 | 1/2010 | Shluzas |
| 6,867,253 B1 | 3/2005 | Chen | | 7,650,887 B2 | 1/2010 | Nguyen et al. |
| 6,869,393 B2 | 3/2005 | Butler | | 7,661,164 B2 | 2/2010 | Chen |
| 6,878,110 B2 | 4/2005 | Yang et al. | | 7,704,207 B2 | 4/2010 | Albrecht et al. |
| 6,884,253 B1 | 4/2005 | McFarlane | | 7,717,847 B2 | 5/2010 | Smith |
| 6,890,295 B2 | 5/2005 | Michels et al. | | 7,727,146 B2 | 6/2010 | Albrecht et al. |
| 6,895,965 B2 | 5/2005 | Scarberry et al. | | 7,727,255 B2 | 6/2010 | Taylor et al. |
| 6,902,541 B2 | 6/2005 | McNally et al. | | 7,736,306 B2 | 6/2010 | Brustad et al. |
| 6,902,569 B2 | 6/2005 | Parmer et al. | | 7,749,415 B2 | 7/2010 | Brustad et al. |
| 6,908,430 B2 | 6/2005 | Caldwell et al. | | 7,753,901 B2 | 7/2010 | Piskun et al. |
| 6,909,220 B2 | 6/2005 | Chen | | 7,758,500 B2 | 7/2010 | Boyd et al. |
| 6,913,609 B2 | 7/2005 | Yencho et al. | | 7,766,824 B2 | 8/2010 | Jensen et al. |
| 6,916,310 B2 | 7/2005 | Sommerich | | 7,811,251 B2 | 10/2010 | Wenchell et al. |
| 6,916,331 B2 | 7/2005 | Mollenauer et al. | | 7,815,567 B2 | 10/2010 | Albrecht et al. |
| 6,929,637 B2 | 8/2005 | Gonzalez et al. | | 7,837,612 B2 | 11/2010 | Gill et al. |
| 6,936,037 B2 | 8/2005 | Bubb et al. | | 7,850,667 B2 | 12/2010 | Gresham |
| 6,939,296 B2 | 9/2005 | Ewers et al. | | 7,867,164 B2 | 1/2011 | Butler et al. |

| | | |
|---|---|---|
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler et al. |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler et al. |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen et al. |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |

| | | | |
|---|---|---|---|
| 2010/0261975 A1 | 10/2010 | Huey et al. | |
| 2010/0286484 A1 | 11/2010 | Stellon et al. | |
| 2010/0298646 A1 | 11/2010 | Stellon et al. | |
| 2011/0021877 A1 | 1/2011 | Fortier et al. | |
| 2011/0028891 A1 | 2/2011 | Okoniewski | |
| 2011/0034935 A1 | 2/2011 | Kleyman | |
| 2011/0034946 A1 | 2/2011 | Kleyman | |
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO95/07056 | 3/1995 |
| WO | WO 95/07056 | 3/1995 |
| WO | WO 95/22289 | 8/1995 |
| WO | WO95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO00/32116 | 6/2000 |
| WO | WO 00/32119 | 6/2000 |
| WO | WO 00/32120 | 6/2000 |
| WO | WO 00/35356 | 6/2000 |
| WO | WO 00/321176 | 6/2000 |
| WO | WO00/54675 | 9/2000 |
| WO | WO 00/54675 | 9/2000 |
| WO | WO00/54676 | 9/2000 |
| WO | WO 00/54676 | 9/2000 |
| WO | WO00/54677 | 9/2000 |
| WO | WO 00/54677 | 9/2000 |
| WO | WO 01/08563 | 2/2001 |
| WO | WO 01/08581 | 2/2001 |
| WO | WO01/08581 | 2/2001 |
| WO | WO 01/26558 | 4/2001 |
| WO | WO 01/26559 | 4/2001 |
| WO | WO 01/45568 | 6/2001 |
| WO | WO 01/045568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO03/032819 | 4/2003 |
| WO | WO03/034908 | 5/2003 |
| WO | WO 03/034908 | 5/2003 |
| WO | WO 03/061480 | 7/2003 |
| WO | WO03/061480 | 7/2003 |
| WO | WO 03/077726 | 9/2003 |
| WO | WO 03/077726 A2 | 9/2003 |
| WO | WO 03/103548 | 12/2003 |
| WO | WO 03/103548 A1 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

Co-Pending U.S. Appl. No. 10/381,220, filed Mar. 20, 2003; Title: Surgical Access Apparatus and Method.
Co-Pending U.S. Appl. No. 10/516,198, filed Nov. 30, 2004; Title: Wound Retractor.
Co-Pending U.S. Appl. No. 10/927,551, filed Aug. 25, 2004; Title: Surgical Access System.

Co-Pending U.S. Appl. No. 11/244,647, filed Oct. 5, 2005; Title: Surgical Access Apparatus and Method.
Co-Pending U.S. Appl. No. 11/245,709, filed Oct. 7, 2005; Title: Surgical Access System.
Co-Pending U.S. Appl. No. 11/330,661, filed Jan. 12, 2006; Title: Sealed Surgical Access Device.
Co-Pending U.S. Appl. No. 11/548,746; filed Oct. 12, 2006; Title Method of Making a Hand Access Laparoscopic Device.
Co-Pending U.S. Appl. No. 11/548,758, filed Oct. 12, 2006; Title: Split Hoop Wound Retractor With Gel Pad.
Co-Pending U.S. Appl. No. 11/548,765; filed Oct. 12, 2006; Title: Split Hoop Wound Retractor.
Co-Pending U.S. Appl. No. 11/548,767, filed Oct. 12, 2006; Title: Circular Surgical Retractor.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Dexterity Protractor Instruction Manual by Dexterity Surgical, Inc.
Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov. 1989, vol. 72, No. 11, pp. 3230-3232.
McSweeney, Cannullation of the Rumen in Cattle and Buffaloes, Australian Veterinary Journal, Aug. 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
European Patent Office, International Search Report and Written Opinion of the International Searching Authority for International Application No. PCT/US2006/039905, mailed Jan. 17, 2007.
Co-Pending U.S. Appl. No. 11/755,305, filed May 30, 2007; Title: Wound Retraction Apparatus and Method.
Co-Pending U.S. Appl. No. 11/548,955, filed Oct. 12, 2006; Title: Hand Access Laparoscopic Device.
Co-Pending U.S. Appl. No. 11/564,409, filed Nov. 29, 2006; Title: Surgical Instrument Access Device.
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/2006/039799 mailed Mar. 27, 2007.
The International Bureau of WIPO, International Preliminary Report on Patentability, dated Aug. 29, 2006, for international application No. PCT/US2004/028250.
The International Bureau of WIPO, International Preliminary Report on Patentability dated Apr. 16, 2008 for PCT Application No. PCT/US2006/039799 mailed Mar. 27, 2007.
The International Bureau of WIPO, International Preliminary Report on Patentability for International Application No. PCT/US2006/039800 dated Apr. 16, 2008.
European Patent Office, International Search Report and the Written Opinion of the International Searching Authority for International Application No. PCT/2006/040073 mailed Jan. 26, 2007.
European Patent Office, International Search Report and the Written Opinion of the International Searching Authority for International Application No. PCT/2006/039905 mailed Jan. 17, 2007.
European Patent Office, International Search Report and the Written Opinion of the International Searching Authority for International Application No. PCT/2006/039883, mailed Jan. 31, 2007.
European Patent Office, International Search Report and the Written Opinion of the International Searching Authority for International Application No. PCT/2006/039800, mailed Apr. 16, 2007.
International Search Report and Written Opinion of the International Searching Authority for PCT application No. PCT/US01/129682.
Co-Pending U.S. Appl. No. 11/548,746, filed Oct. 12, 2006, Title: Method of Making a Hand Access Laparoscopic Device.
Co-Pending U.S. Appl. No. 11/548,765, filed Oct. 12, 2006; Title: Split Hoop Wound Retractor.
Co-Pending U.S. Appl. No. 11/548,781, filed Oct. 12, 2006; Title: Wound Retractor With Gel Cap.
Co-Pending U.S. Appl. No. 12/108,400, filed Apr. 23, 2008; Title: Wound Retraction Apparatus and Method.
Co-Pending U.S. Appl. No. 12/358,080, filed Jan. 22, 2009; Title: Surgical Instrument Access Device.
European Patent Office, Supplementary European Search Report for European Application No. EP 01 97 3379, dated Jul. 5, 2007, based on International Patent Application No. PCT/US01/29682, filed Sep. 21, 2001.
European Patent Office, International Search Report and the Written Opinion of the International Searchinig Authority for PCT Application No. PCT/US2004/05484.
Nternational Bureau of WIPO, International Preliminary Report on Patentability for International Patent Application No. PCT/US2006/039905, mailed Apr. 24, 2008.
Declaration of John R. Brustad Under 37 C.F. R. 1.132, dated Dec. 10, 2009.
"Applied GelPort™ Advanced Access Device" product sales brochure dated 2001.
"Cap Ring" production drawing dated Jan. 19, 2001.
"Gelport® Laparoscopic Hand Access System" product sales brochure dated 2005.
"Cap Ring Medium" production drawing dated Aug. 16, 2005.
US 5,334,646, Chen (withdrawn).
U.S. Appl. No. 10/902,756, filed Jul. 29, 2004; Title: Hand Access Port Device, now abandoned.
U.S. Appl. No. 10/802,125, filed Mar. 15, 2004; Title: Surgical Guide Valve, now abandoned.
U.S. Appl. No. 10/927,551, filed Aug. 25, 2004; Title: Surgical Access System, now abandoned.
U.S. Appl. No. 10/695,295; filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.

U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.
Office Action in co-pending patent application No. 12/360,634, dated Jan. 24, 2011 in 12 pages.
Office Action in co-pending patent application No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Apr. 16, 2008, for International Application No. PCT/US2006/039799.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80.
International Search Report and Written Opinion in PCT/IE2005/000113 mailed on Feb. 22, 2006.
International Search Report and Written Opinion in PCT/IE2007/000050 mailed on Aug. 13, 2007.
Declaration of John R. Brustad dated Dec. 10, 2009, submitted in U.S. Appl. No. 11/548,955, including Appendices A-D regarding product sales brochures and production drawings from 2001 and 2005.
The International Searching Authority, The International Search Report and Written Opinion of the International Searching Authority for International Application No. PCT/US08/63445, mailed Sep. 29, 2008.
The International Searching Authority, The International Search Report and Written Opinion of the International Searching Authority for International Application No. PCT/US08/063463 mailed Sep. 10, 2008.
The International Bureau of WIPO, International Preliminary Report on Patentability for International Application No. PCT/US2008/063463, dated Nov. 17, 2009, entitled "Surgical Retractor".
The International Bureau of WIPO, International Preliminary Report on Patentability for International Application No. PCT/US08/63445, issued Nov. 17, 2009, entitled "Surgical Retractor with Gel Pad".
International Searching Authority—US, International Search Report and Written Opinion of the International Searching Authority for International Application No. PCT/US04/25511, mailed Nov. 7, 2007.
International Bureau of WIPO, International Report on Patentability for International Application No. PCT/US04/25511, mailed Dec. 6, 2007.
European Patent Office, European Search Report for European Patent No. 11172709.5, dated Aug. 16, 2011.
European Patent Office, European Search Report for European Patent No. 11172706.1, dated Aug. 16, 2011.
Harold W. Harrower, M.D. Isolation of Incisions into Body Cavities, The American Journal of Surgery, p. 824-826, Dec. 1968.

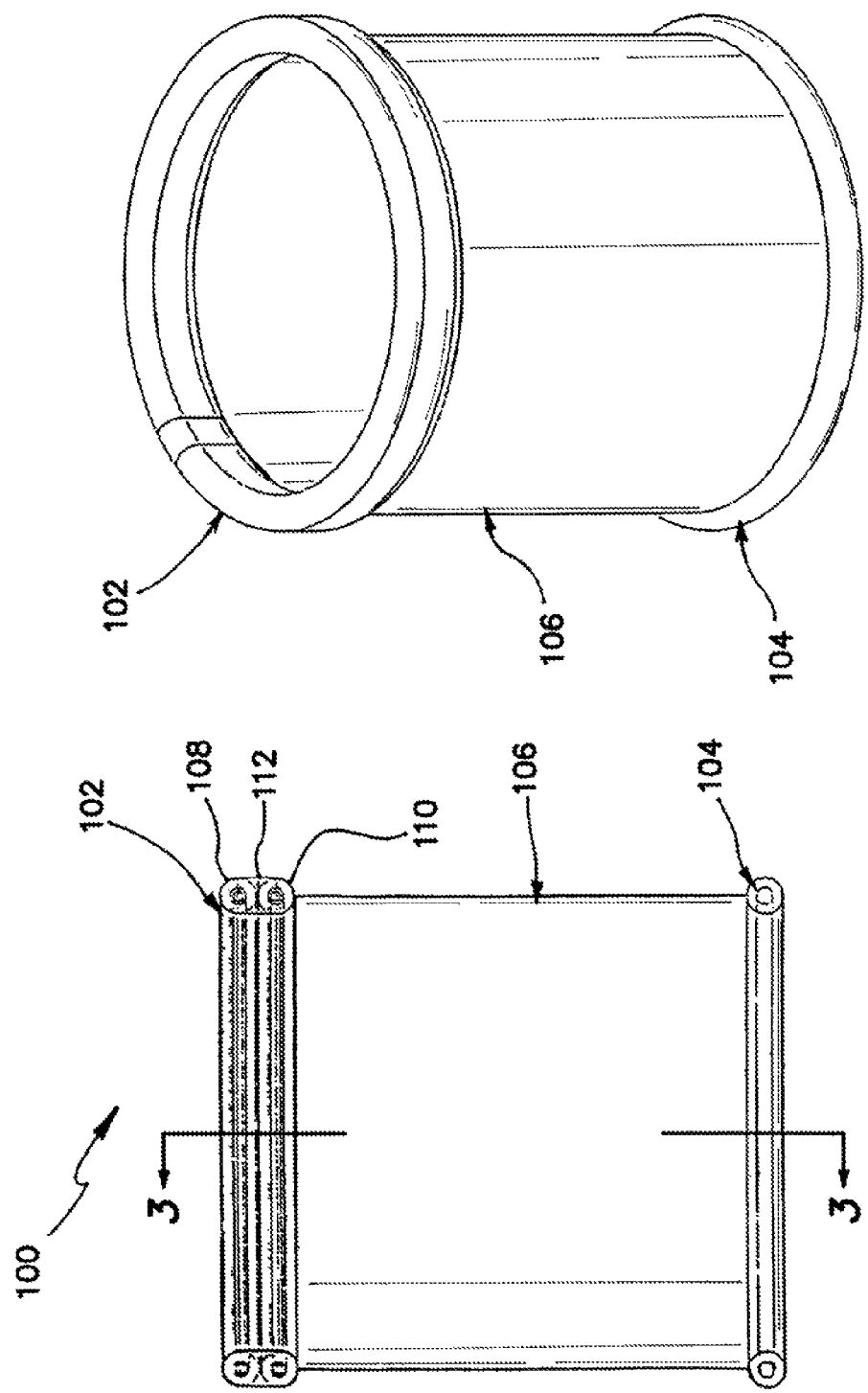

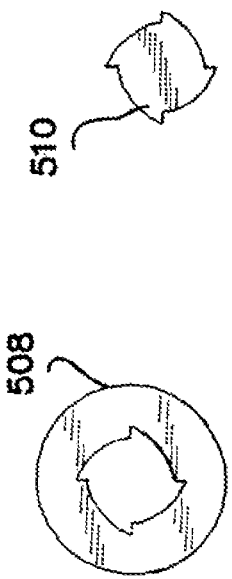
FIG. 7b
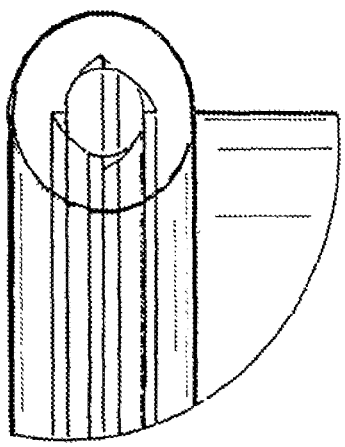
510
FIG. 6
508
FIG. 5
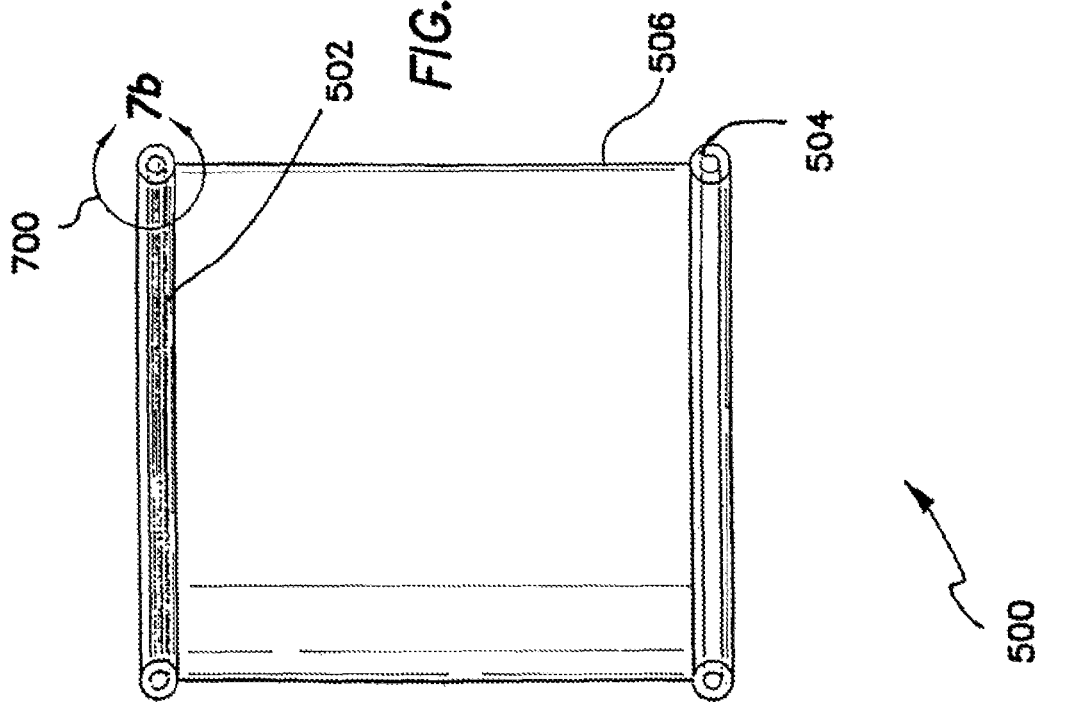
FIG. 7a

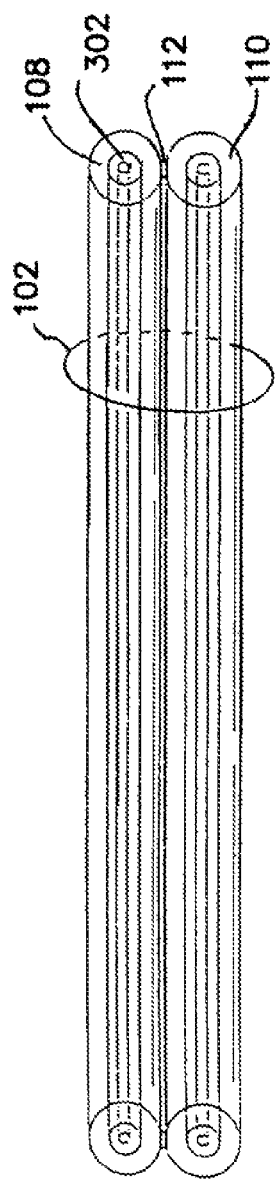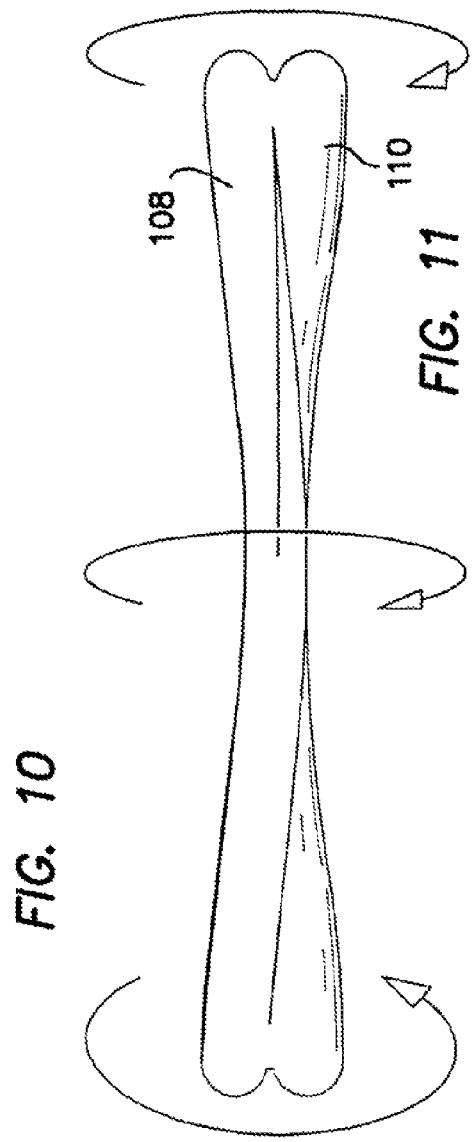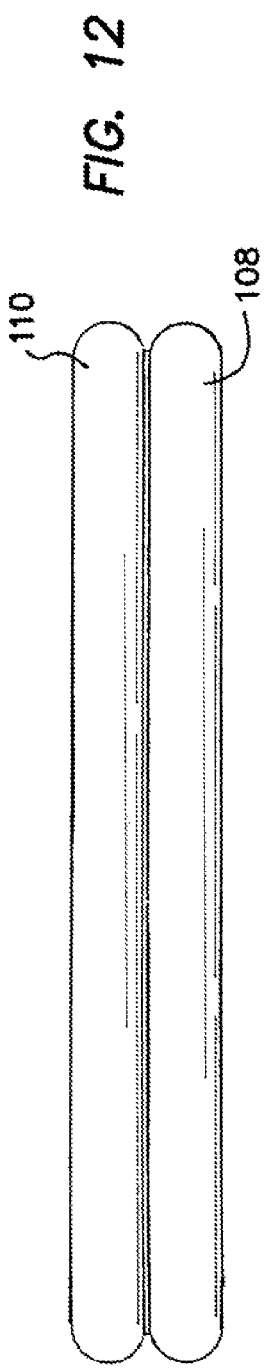

510

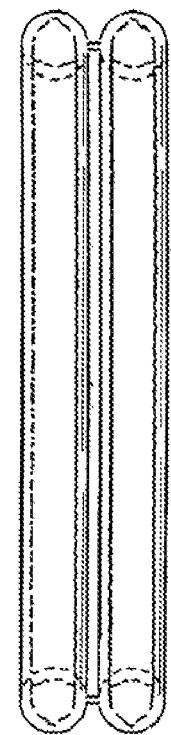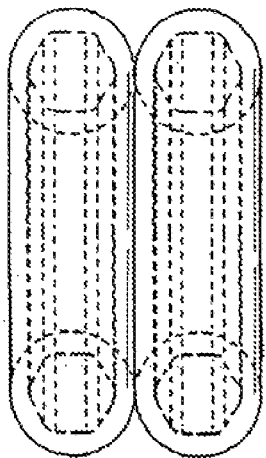
FIG. 17b
FIG. 17c
FIG. 17a

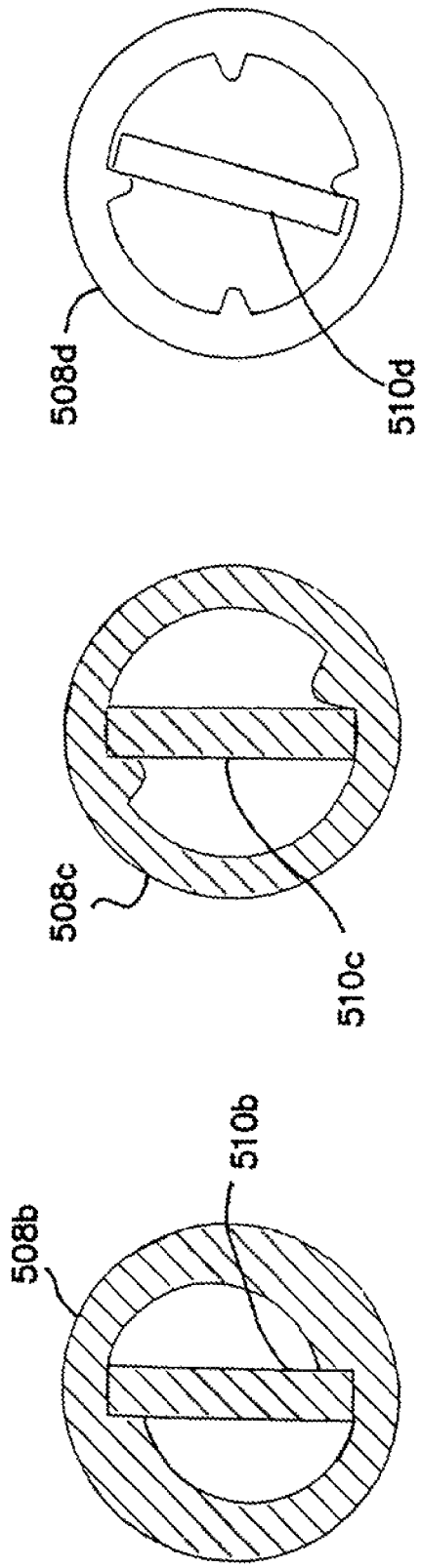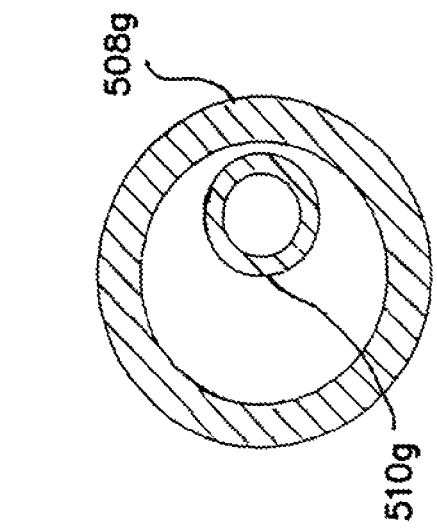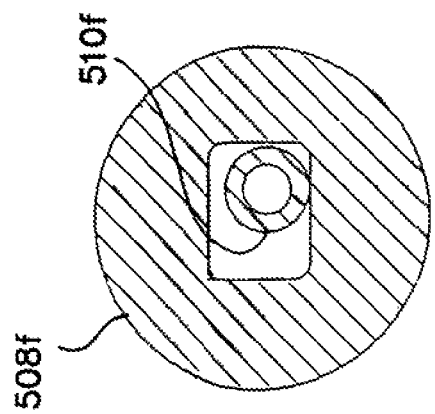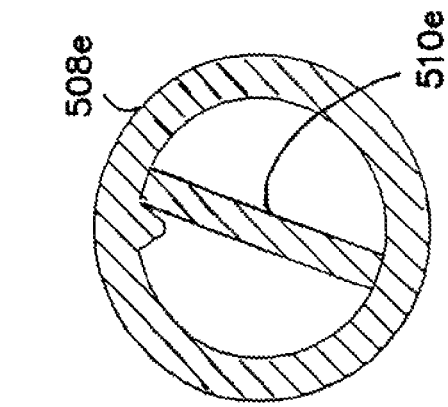

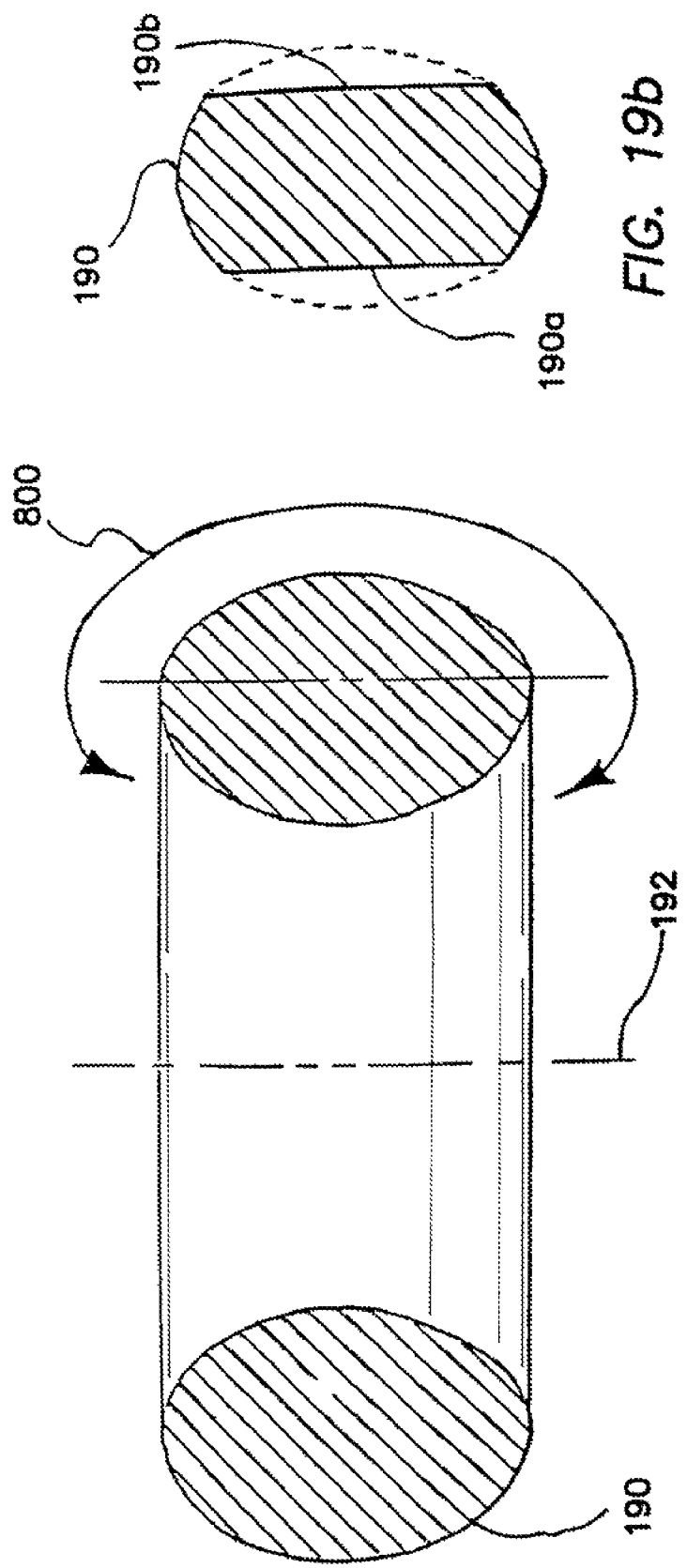

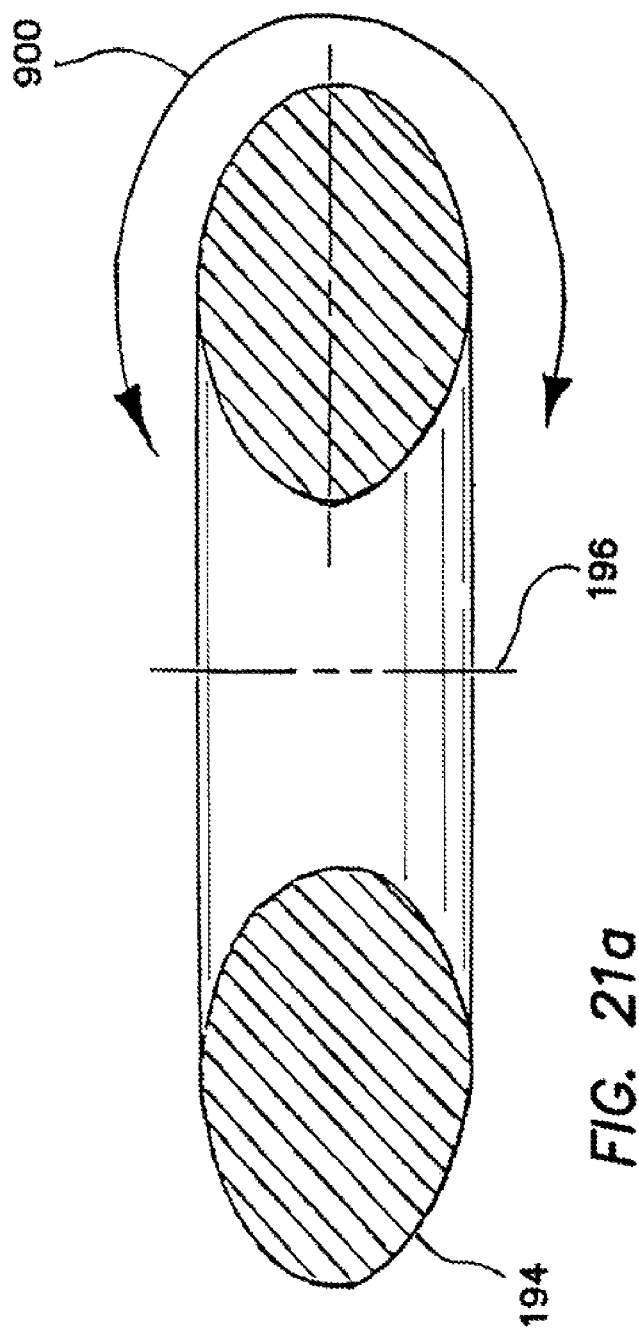
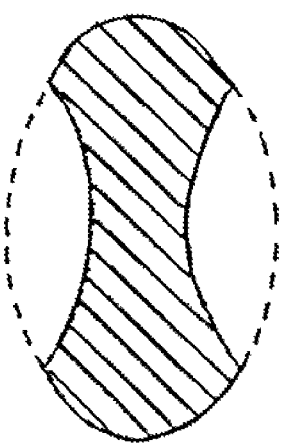
FIG. 21a
FIG. 21b

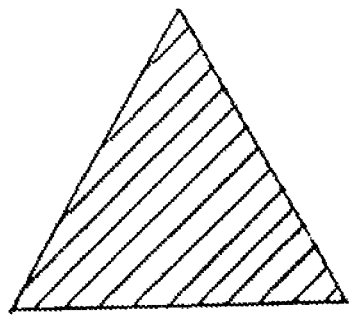
FIG. 23a
FIG. 23b
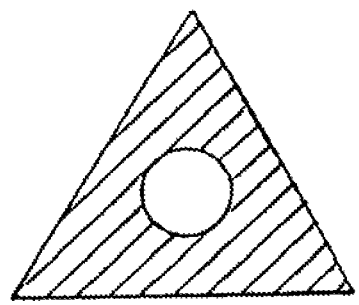
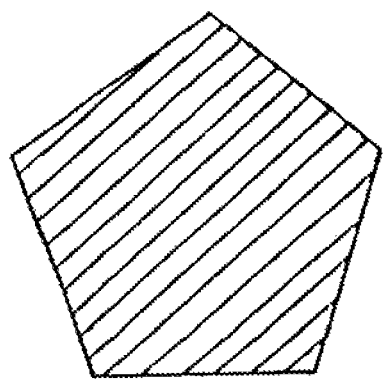
FIG. 24b
FIG. 24a
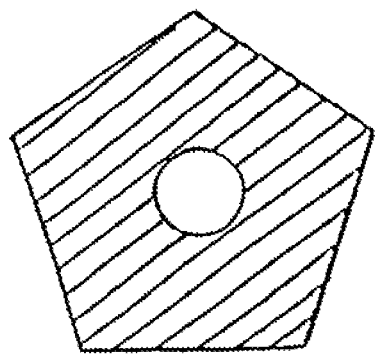

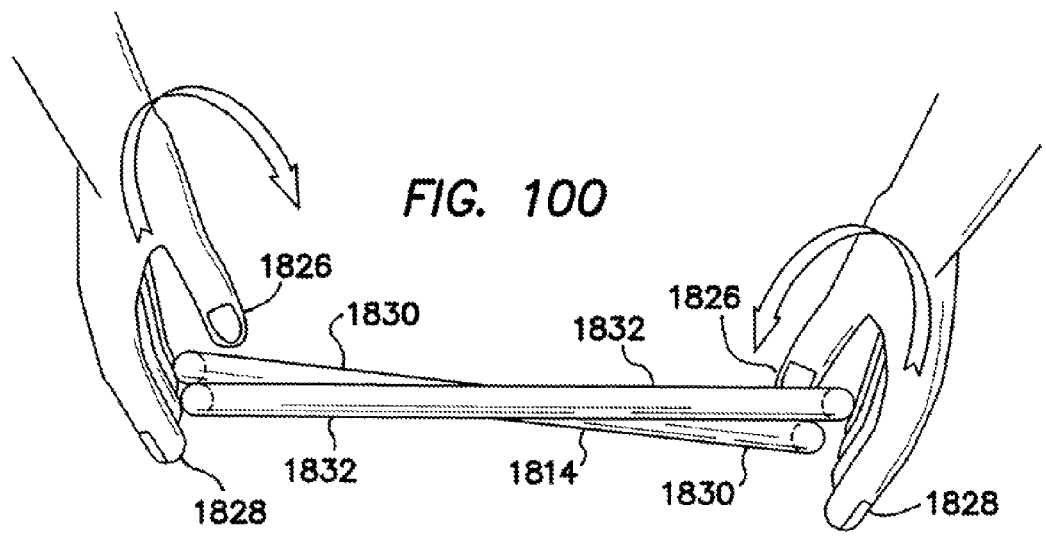
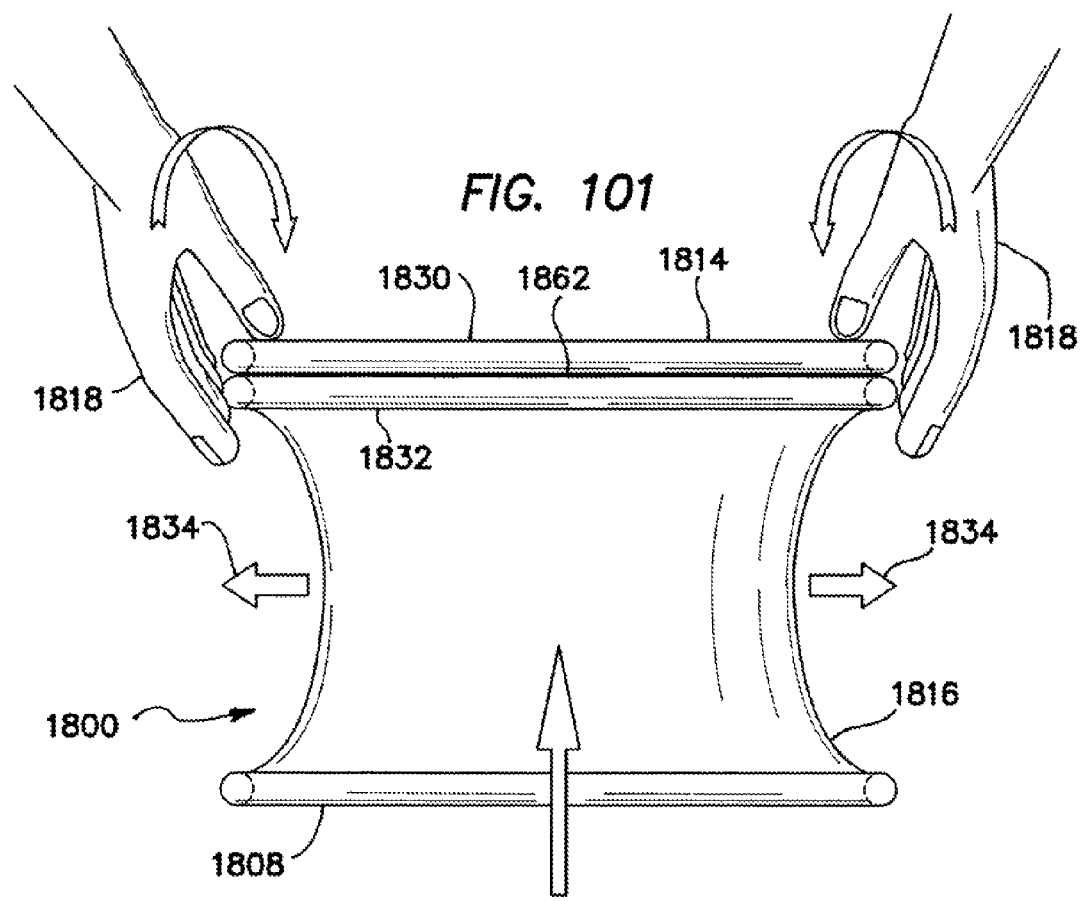

WOUND RETRACTOR WITH GEL CAP

CROSS-REFERENCE TO RELATED APPLICATIONS

This application is a continuation of U.S. patent application Ser. No. 12/791,666 filed Jun. 1, 2010, now U.S. Pat. No. 7,883,461, which is a continuation of U.S. patent application Ser. No. 11/548,781, filed Oct. 12, 2006, now U.S. Pat. No. 7,727,146, which claims the benefit of U.S. Patent Application No. 60/828,089, filed on Oct. 4, 2006; U.S. Patent Application No., 60/803,965, filed Jun. 5, 2006; U.S. Patent Application No. 60/803,346, filed May 26, 2006; U.S. Patent Application No. 60/745,730, filed Apr. 26, 2006; and U.S. Patent Application No. 60/726,826, filed Oct. 14, 2005, of which the entire disclosures are incorporated by reference herein.

BACKGROUND

This invention relates substantially to devices and other apparatuses facilitating sealed access with surgical instruments, such as a surgeon's hand, across a body wall and into a body cavity. This invention also relates to an improved wound retractor providing ease of incremental retraction and alignment to fit a wide range of incision sizes.

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery that relies on surgical instruments inserted through the abdominal wall to reach an operative site within the abdominal cavity. In order to increase space around the operative site within the cavity, insufflation gases are typically introduced to inflate the cavity and elevate the abdominal wall. The pressurizing of the abdominal cavity is referred to as pneumoperitoneum. In this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals that prevent the escape of the gases in the absence of instruments, and instrument seals that prevent the escape of the gases in the presence of instruments. Unfortunately, the instrument seals have been able to accommodate only a narrow range of instrument diameters. Multiple seal pairs had to be provided where wider ranges were desired.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used, but only for very small diameter access such as that required by a guidewire.

Each of the prior devices suffers from drawbacks that make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeon's arm. When the arm is removed, a separate zero seal has been required to prevent the escape of blood or insufflation gases.

Surgery typically involves making an incision large enough to accommodate a surgeon's hand and/or multiple instruments. The incision must be kept clean since it is susceptible to infection if touched by diseased body parts and/or contaminated instruments. As such, wound protectors are available to insure that exposed sides of an incision are covered and protected from contaminants. A common deficiency of wound protectors is their lack of ease of retraction adjustability and stability. There is a need in the art for an improved wound retractor that can be easily retracted to fit a wide range of incision sizes.

SUMMARY

The invention is directed to a wound retractor that is adapted to retract a surgical incision in a biological body wall to a desired diameter. The wound retractor includes a double-tube outer ring that has an annular axis. The double-tube outer ring includes a first circular tube and a second circular tube that are separated axially. Each of the circular tubes includes a lumen. The outer ring is adapted for juxtaposition with an outer surface of the body wall and for disposition relative to the incision in the body wall. The wound retractor also includes an inner ring that is adapted for juxtaposition with an inner surface of the body wall and for disposition relative to the incision in the body wall. The wound retractor further includes a distensible sleeve that couples the outer ring to the inner ring. The sleeve is adapted to traverse the incision in the body wall. Additionally, the wound retractor includes a first substantially noncompliant, split hoop positioned in the lumen of the first circular tube and a second substantially noncompliant, split hoop positioned in the lumen of the second circular tube. The outer ring is adapted to roll over itself and around the annular axis to roll the sleeve around the outer ring.

In one aspect, each of the first and second split hoops functions as an axle about which the outer ring may turn for half a rotation. In another aspect, the sleeve includes a material that is flexible and impermeable to fluids and bacteria. In another aspect, the inner ring is made of materials having sufficient hardness to retain the shape of the inner ring after insertion of the inner ring into a body cavity. In another aspect, the outer ring is made of materials that allow the outer ring to be turned around its annular axis. In another aspect, the first circular tube of the outer ring is coupled to the second circular tube of the outer ring by a web. In another aspect, at least one of the first and second noncompliant split hoops includes a single split about its circumference with the split creating a first end of the split hoop and a second end of the split hoop. In one aspect, the first and second ends of the split hoop substantially abut each other when the split hoop is in its neutral position. In another aspect, the split hoop includes a space between the first and second ends when the split hoop is in its neutral position. In this aspect, the space between the first and second ends of the split hoop is sufficient to substantially prevent the first and second ends of the split hoop from contacting each other when the split hoop contracts while rolling the sleeve around the outer ring. In another aspect, at least one of the first and second noncompliant split hoops includes two or more splits about the circumference of the split hoop. The splits create a plurality of hoop portions with each hoop portion including a first end and a second end. The two or more splits are substantially equally spaced about the circumference of the split hoop. In one aspect, the first and second ends of adjacent hoop portions substantially abut each other when the split hoop is in its neutral position. In another aspect, the split hoop includes a space between the first and second ends of adjacent hoop portions when the split hoop is in its neutral position. In this aspect, the sum of the spaces between the first and second ends of adjacent hoop portions is sufficient to substantially prevent the first and second ends of adjacent hoop portions from contacting each other when the split hoop contracts while rolling the sleeve around the outer ring.

These and other features and advantages of the invention will become more apparent with a discussion of embodiments in reference to the associated drawings.

BRIEF DESCRIPTION OF THE DRAWINGS

FIGS. 1a and 1b illustrate an elevation view and a perspective view of an incrementally adjustable wound retractor in accordance with an embodiment of the invention;

FIG. 5 is a cross-section view of a hollow tube of an outer ring of a wound retractor;

FIG. 6 is a cross-section view of an inner rod of the outer ring of the wound retractor of FIG. 5;

FIG. 7a is a side view of the incrementally adjustable wound retractor of FIG. 5;

FIG. 7b is a cutaway side view of the incrementally adjustable wound retractor of FIG. 5;

FIG. 10 is a side section view of an outer ring of a wound retractor including a wire;

FIG. 11 is a side view of the outer ring of FIG. 10 being rolled to retract an incision;

FIG. 12 is a side view of the outer ring of FIG. 10 after being rolled to retract an incision;

FIGS. 17a through 17e are section views of the outer ring of the invention;

FIGS. 18a through 18l are section views of hollow tubes and inner rods of the outer rings;

FIGS. 19a through 19g are section views of outer rings having generally prolate cross-sections;

FIGS. 21a through 21e are section views of outer rings having generally oblate cross-sections;

FIG. 23a is a section view of an outer ring having a triangular cross-section;

FIG. 23b is a section view of the outer ring of FIG. 23a further including a lumen;

FIG. 24a is a section view of an outer ring having a cross-section including an odd number of sides, such as a pentagon;

FIG. 24b is a section view of the outer ring of FIG. 24a further including a lumen;

FIG. 100 is a side view depicting the third step of the technique employed to wind the sleeve of the wound retractor upon the rigid outer ring of the wound retractor;

FIG. 101 is a side view of the assembled wound retractor prior to winding the sleeve upon the rigid outer ring;

FIG. 118 is a section view of the rigid outer ring having three portions with a lumen in each of the three portions;

FIG. 119 is a section view of the rigid outer ring having three portions with a lumen in each of the three portions;

FIG. 120 is a section view of the rigid outer ring having three portions with two lumens with the lumens being positioned in the outer portions;

FIG. 121 is a perspective view of an assembled wound retractor having a twisted, rigid outer ring;

FIG. 122 is a perspective view of the outer ring of the wound retractor of FIG. 121; and FIG. 123 is a side view of the wound retractor of FIG. 121.

DETAILED DESCRIPTION

Figure 2A:
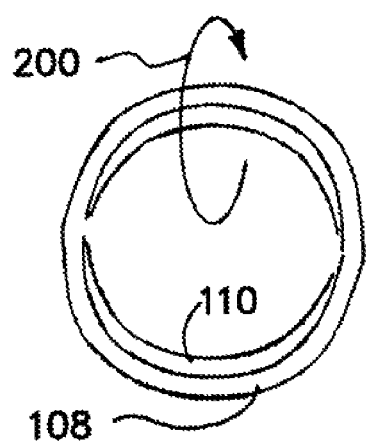
FIGS. 2a through 2c illustrate the retraction of the outer ring of the wound retractor of FIG. 1 to retract a desired incision.
Figure 2B:
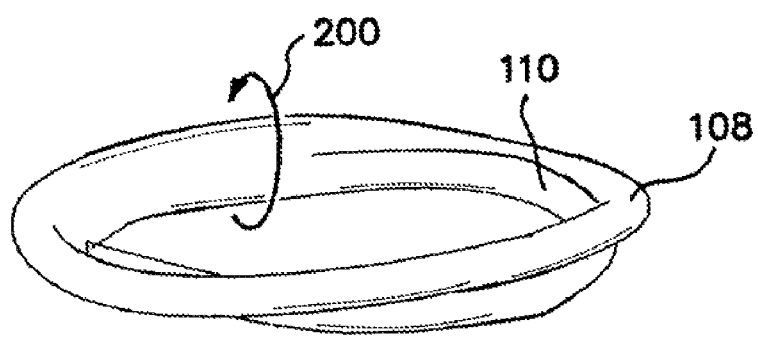
Figure 2C:
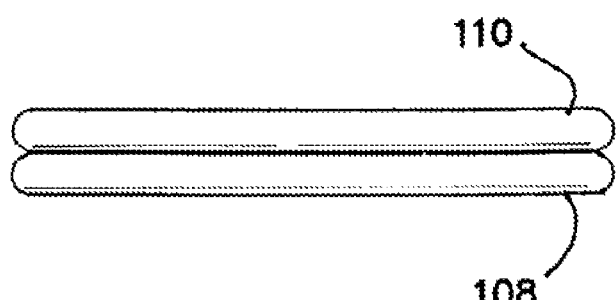
Figure 3:
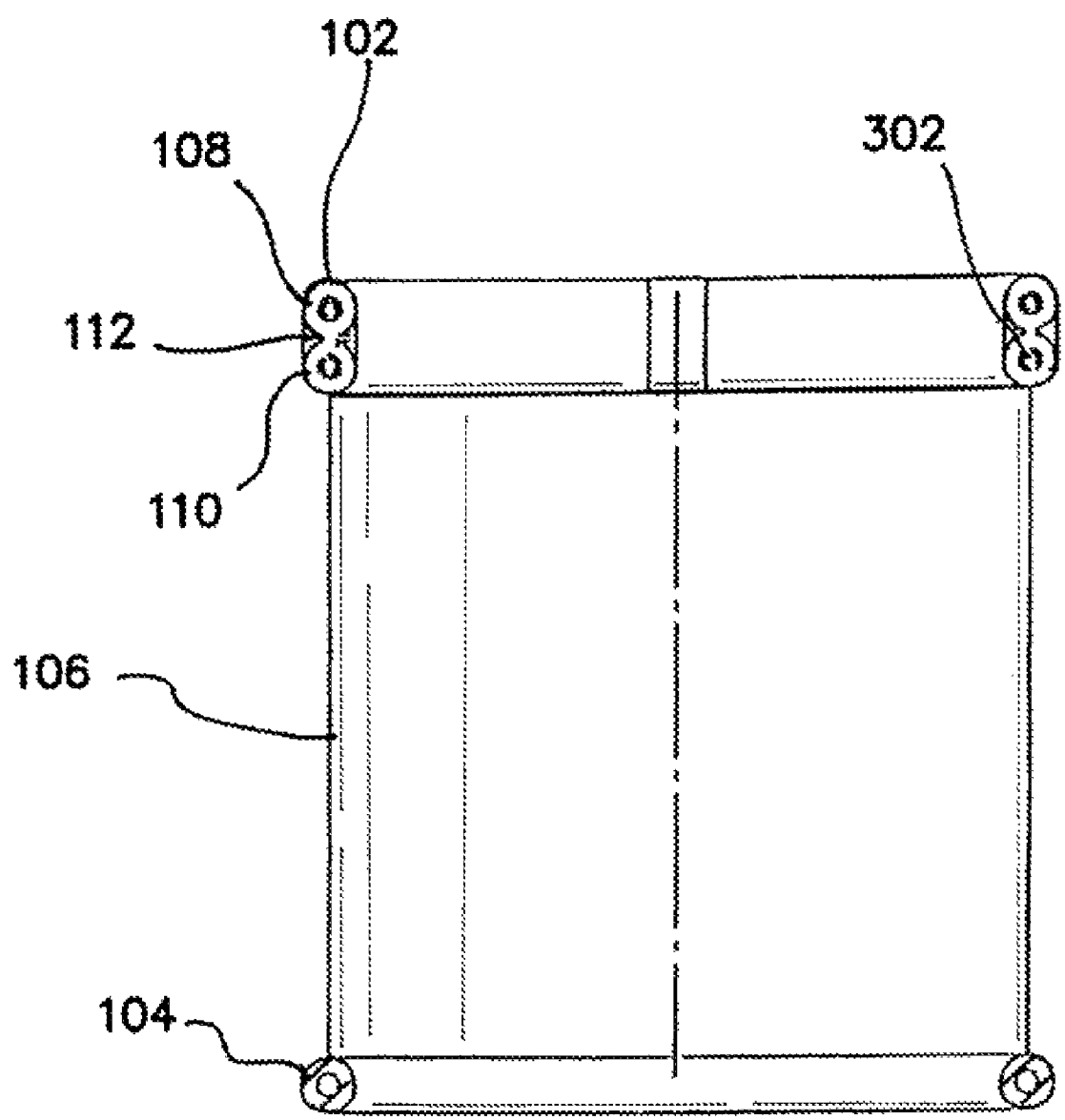
FIG. 3 is a longitudinal cross-section view of the wound retractor of FIG. 1 taken along line 3-3.
Figure 4:
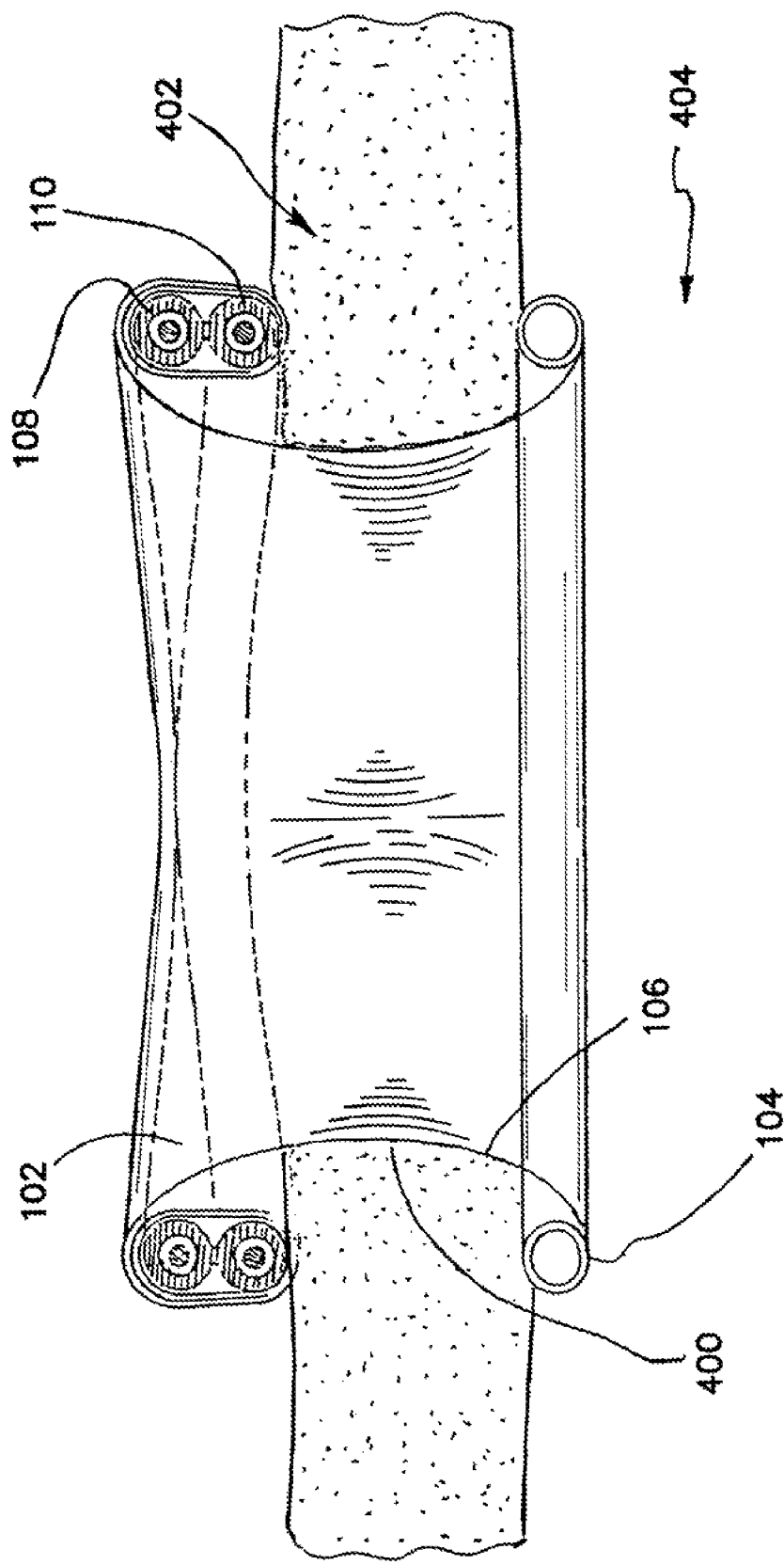
FIG. 4 illustrates the wound retractor of FIG. 1 deployed in an incision.

FIGS. 1a, 1b and 3 illustrate a wound retractor 100 in accordance with a first embodiment of the invention. The wound retractor 100 includes a double-tube outer ring 102, an inner ring 104, and a distensible sleeve 106 coupling the outer ring and the inner ring. The sleeve 106 may be coupled to the outer ring 102 and the inner ring 104 by heat seal, adhesive, or other means that are well known in the art. The sleeve 106 may be made of a material that is flexible and impermeable to fluids and bacteria. The inner ring 104 may be made of materials of sufficient hardness to retain its shape after insertion into a body cavity 404 (FIG. 4). The materials of which the outer ring 102 is made must allow the outer ring to be turned around its annular axis as further described below and illustrated in FIGS. 2a-2c. The shape of the outer ring 102 affects both its ability to grip and to provide stability during and after adjustment. The double-tube outer ring 102 includes a first circular tube 108 and a second circular tube 110 that are separated axially. The first and second circular tubes 108, 110 may be joined together by a small web 112. Each of the circular tubes 108 and 110 may be solid or include a lumen.

FIGS. 2a-2c illustrate the retraction and adjustment of the outer ring 102 to fit an incision. In accordance with the invention, the wound retractor 100 is axially adjustable in increments. In particular, the upper end of the sleeve 106 can be wrapped around the outer ring 102 so as to tightly seal the sides or edges of the incision. The unique shape of the outer ring 102 provides for an easy snap action when rolled about itself. The outer ring 102 also provides for incremental shortening of the sleeve 106 and for stability after installation. FIG. 3 illustrates a longitudinal cross-section view of the wound retractor 100 taken along line 3-3.

FIG. 4 illustrates the wound retractor 100 deployed in a wound opening 400. To deploy the wound retractor 100, an incision in the shape of a slit is first made in the body wall 402 of a patient, such as the abdominal wall 402. The inner ring 104 is compressed and the inner ring and sleeve 106 are manually inserted into the body cavity 404 through the incision with the outer ring 102 remaining external to the body cavity. Once the inner ring 104 is within the body cavity 404, it expands around the inner surface of the incision 400 so as to be generally parallel to the outer surface of the abdominal wall 402. The sleeve 106 provides a working channel from outside the body cavity 404 to inside the body cavity.

The outer ring 102 initially rests above the abdominal wall 402 around the wound opening 400. Since the upper end of the sleeve 106 is coupled to the outer ring 102, the sleeve 106 can be drawn upwards and radially outward or inward, thereby drawing the inner ring 104 tightly against the inner surface of the abdominal wall 402. Moreover, the intermediate portion of the sleeve 106 is drawn tightly against the sides and edges of the wound opening 400, thereby retracting the adjacent tissue and producing a tightly sealed opening in the body cavity 404. The sleeve 106 contacts the entire surface of the wound 400 and protectively covers and seals it from contamination and infection. Depending on the size and depth of the incision 400, the user can roll up the sleeve 106 by gripping the double-tube outer ring 102 and turning it in a direction 200 as illustrated in FIGS. 2a-2c until the sleeve 106 abuts the outer edge of the wound opening 400. The inner ring 104 is adapted for juxtaposition with the inner surface of the abdominal wall 402 and the outer ring 102 is adapted for juxtaposition with the outer surface of the abdominal wall. Both the inner ring 104 and the outer ring 102 are adapted for disposition relative to the incision 400 in the abdominal wall 402. The sleeve 106 is adapted to traverse the incision 400 in the abdominal wall 402.

The outer ring 102 has a unique and novel double-tube configuration wherein through simple manipulation of forcing a first tube in a first direction and a second tube in a second direction, the positions of the first and second tubes can be inverted resulting in fast and easy turning of the tubes as illustrated in FIGS. 2a-2c. In one embodiment of the invention, the outer ring 102 is rotated by pushing the bottom tube or second circular tube 110 inward while pulling the top tube or first circular tube 108 outward (see FIG. 2a). The combination of the above steps results in inversion of the first and second circular tubes as illustrated in FIG. 2c. The outer ring 102 can be rotated in 180° turns, thereby retracting the sleeve 106. The above process can be repeated until a desired compression or wound opening is achieved.

An advantage of the wound retractor 100 of the present invention is it provides for an easier, faster and higher retraction rate than that known in the prior art, thereby resulting in less traumatic effects to the patient. Another advantage of the wound retractor 100 of the present invention is it provides tactile gripping and incremental rolling of the sleeve 106 about the outer ring 102. In the above description, the first and second tubes of the outer ring are in a vertical position but it should be appreciated that the first and second tubes may be in different positions relative to one another, such as a horizontal position. In comparison to retractors of the prior art, the substantially noncompliant hoops 118 in the lumens of the outer ring 102 provide greater strength, which in turn provides better retraction. The substantially noncompliant hoops 118 control the shape of the wound opening 400, rather than the wound opening controlling the shape of the wound retractor 100. In this manner, the wound retractor 100 of the present invention provides better isolation, protection, and sealing of the wound 400.

In another embodiment of the invention, a small wire 302, such as a stainless steel wire, is placed inside a lumen of the double-tube outer ring 102 (see FIGS. 3 and 10-13) so as to provide an audible signal as the outer ring 102 is turned. As the double-tube outer ring 102 is turned, the wire 302 deflects against the tubing wall so as to provide audible feedback to the user. Another feature of the wire 302 is it provides retraction stability to the wound retractor 100.

After surgery, the wound retractor 100 may be retrieved by grabbing the inner ring 104 and the sleeve 106 and pulling them through the wound opening 400. The use of the sleeve 106 and the ease of retracting the outer ring 102 provide higher compression between the inner and outer rings. As a result, the wound retractor 100 provides incremental adjustability to fit a wide range of incision sizes and isolates and protects the wound from bacterial infection as diseased body parts and contaminated instruments are passed through the wound.

FIGS. 5-9 and 14-16 illustrate a wound retractor 500 having a roller design in accordance with another embodiment of the invention. The wound retractor 500 includes an outer ring 502, an inner ring 504, and a distensible sleeve 506 coupling the outer ring 502 and the inner ring 504. The sleeve 506 can be coupled to the outer ring 502 and the inner ring 504 by heat seal, adhesive or other means that are well known in the art. The outer ring 502 also includes a hollow tube or lumen 508 that has a fan-like shape cross-section as illustrated in FIG. 5. The outer ring 502 further includes an inner rod 510 that has a similar fan-like geometry on its outer surface, as illustrated in FIG. 6. The hollow tube 508 and the inner rod 510 are coaxially joined to form the outer ring 502 of the wound retractor 500.

Figure 8:
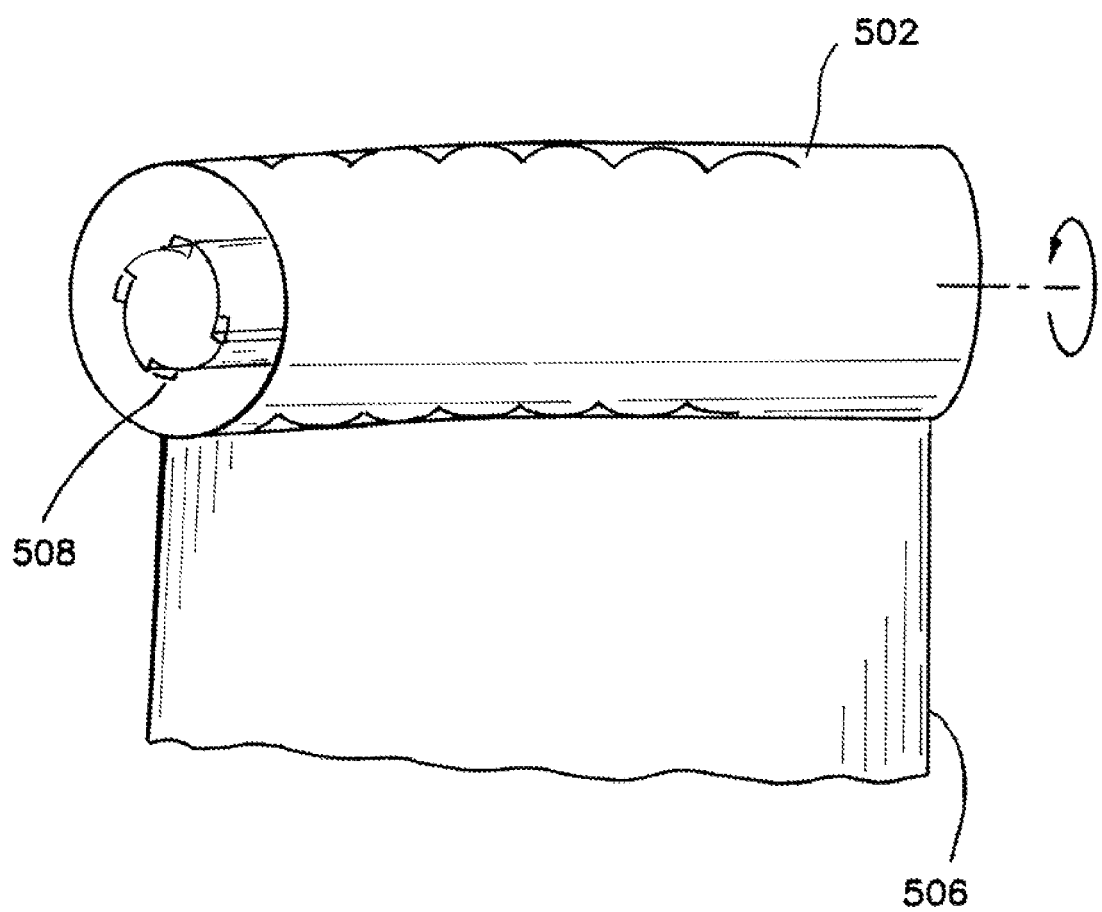
FIG. 8 illustrates the retraction and alignment of the outer ring of FIG. 7 to fit an incision.

The fan-like geometry of the outer ring 502 serves as an incremental rotating mechanism. In particular, when the hollow tube 508 is manually rolled out of its coaxial alignment with respect to the inner rod 510, the hollow tube 508 will index itself until it matches the next alignment point of the inner rod 510 as illustrated in FIG. 8. When the hollow tube 508 and the inner rod 510 are coaxially aligned, they lock in place, thereby preventing further indexing until the steps of retracting are repeated. It is appreciated that each of the hollow tube 508 and the inner rod 510 has at least one alignment point providing indexing and incremental rotation of the outer ring 502. That is, the outer ring 502 can incrementally retract in steps based on the number of alignment points or indexes on the fan.

Figure 9:
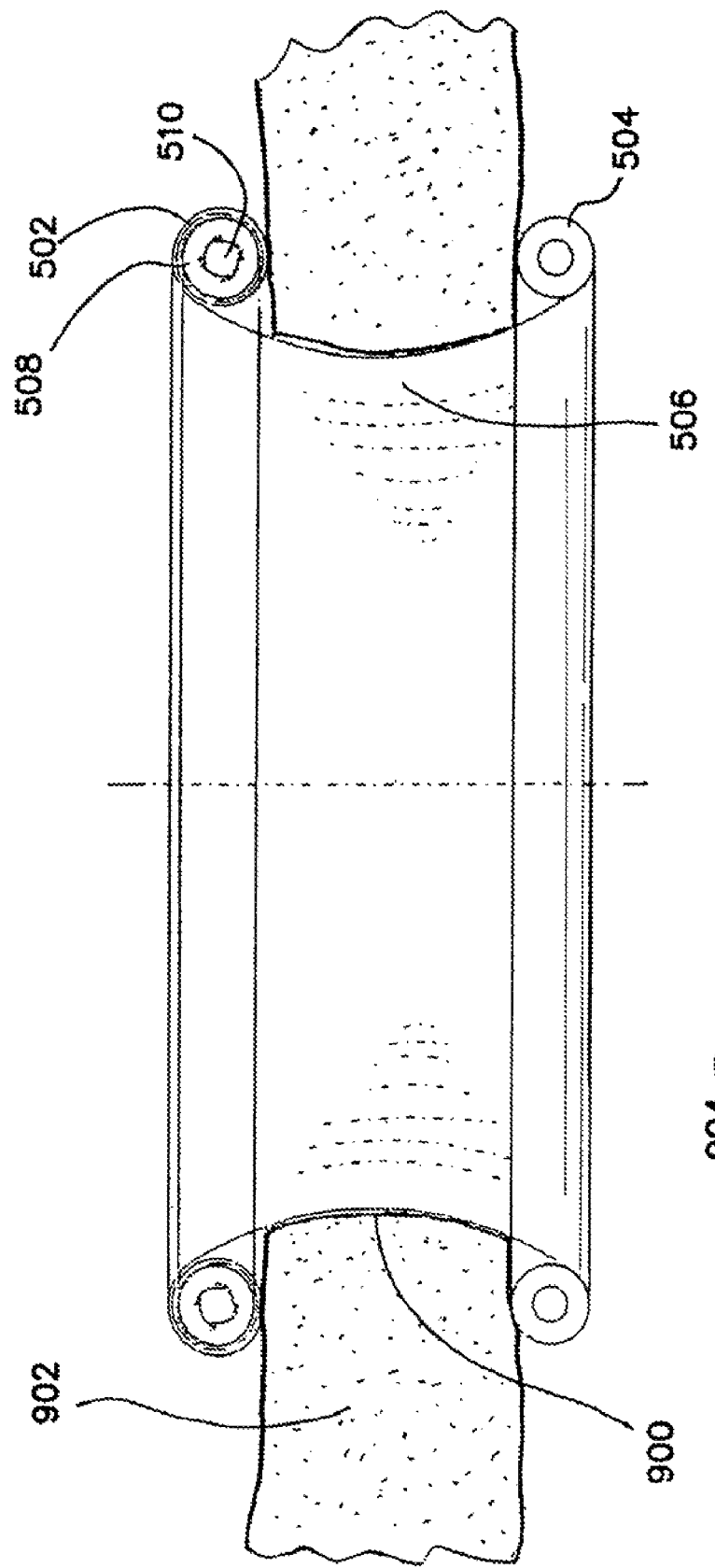
FIG. 9 illustrates the wound retractor of FIG. 7 deployed in an incision.
Figure 13:
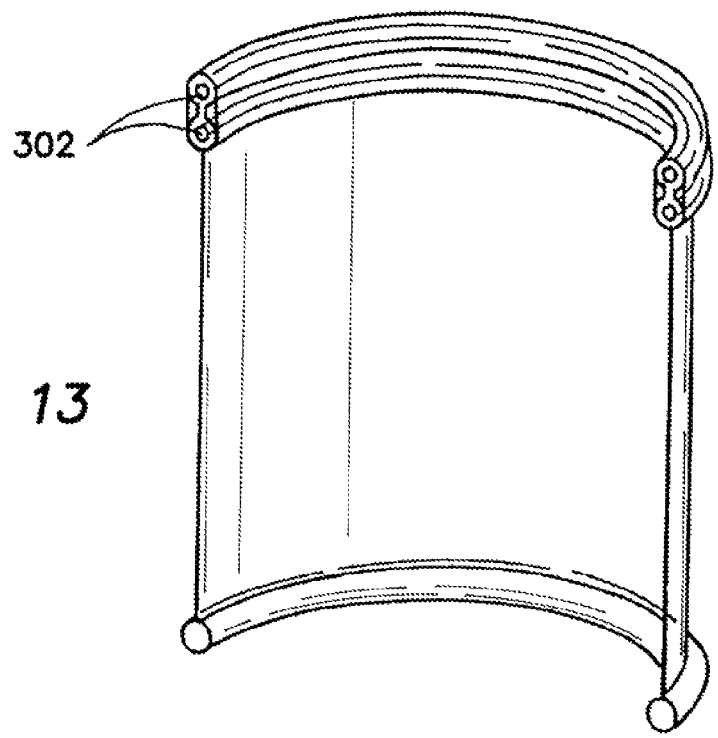
FIG. 13 is a perspective section view of the wound retractor of FIG. 10.
Figure 14:
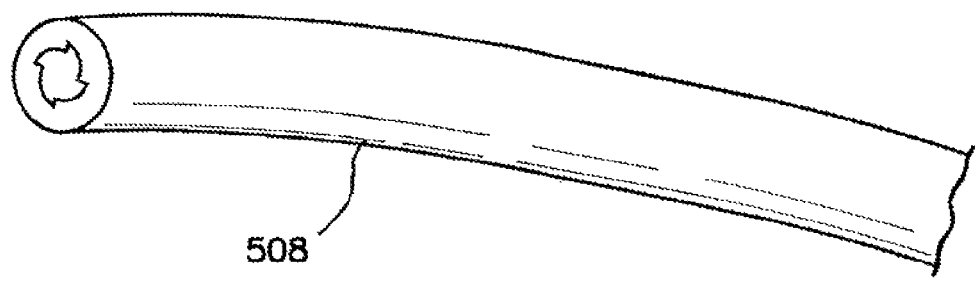
FIG. 14 is a perspective section view of the hollow tube of the outer ring of the wound retractor of FIG. 7.
Figure 15:
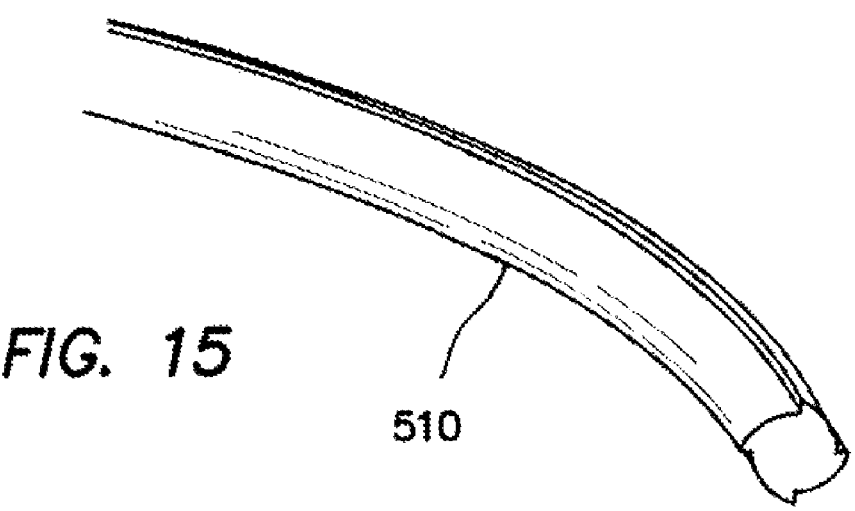
FIG. 15 is a perspective section view of the inner rod of the outer ring of the wound retractor of FIG. 7.
Figure 16:
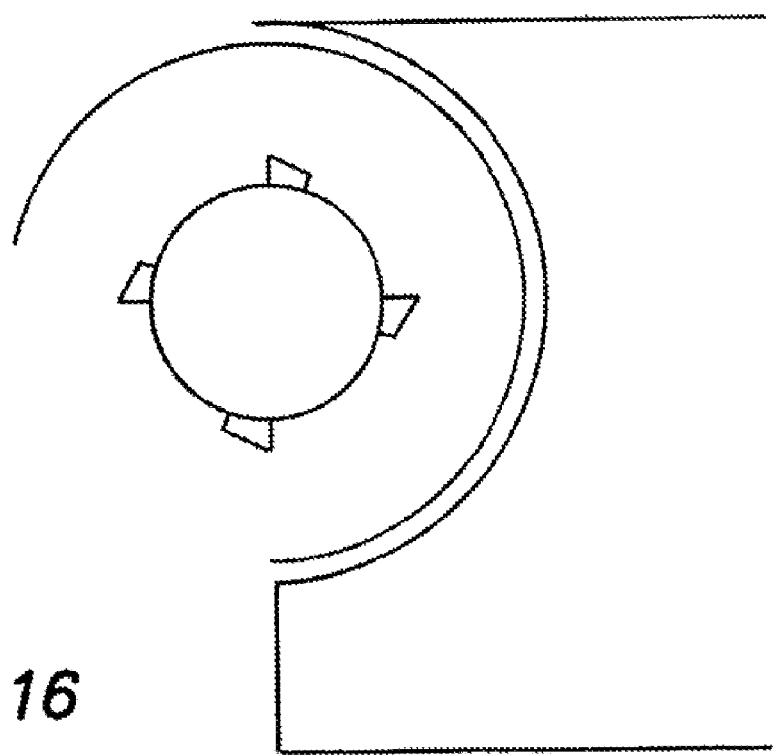
FIG. 16 is a section view of the hollow tube and inner rod of FIG. 7 coaxially joined.
Figure 17E:
Figure 17D:
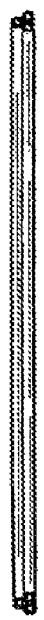
Figure 18A:
Figure 18J:
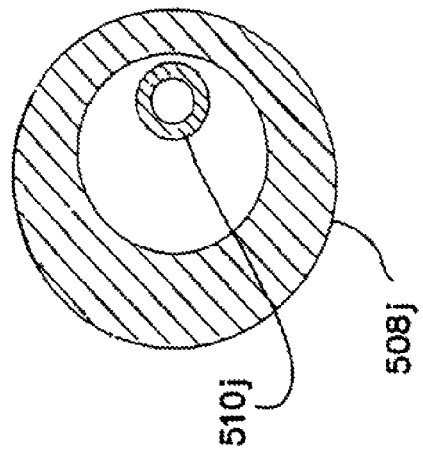
Figure 18I:
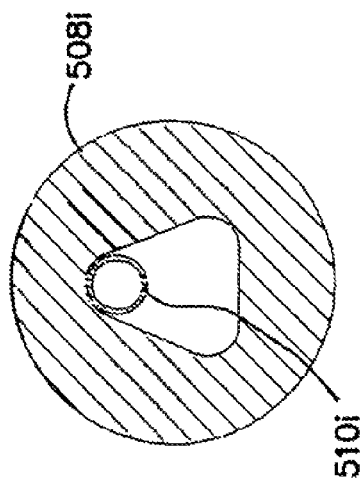
Figure 18L:
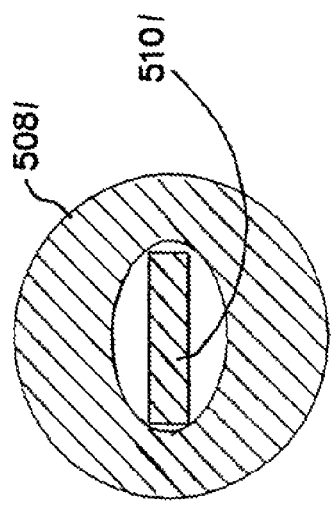
Figure 18H:
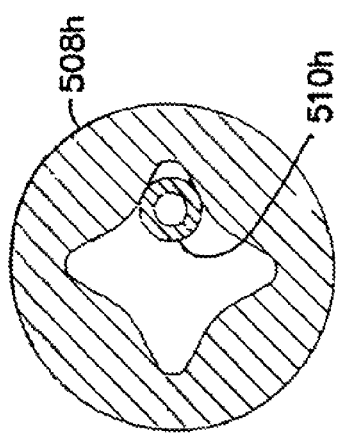
Figure 18K:
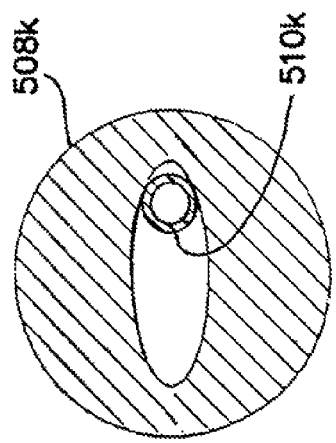

FIG. 9 illustrates a process of installing the wound retractor 500 in a wound opening 900. An incision in the shape of a slit is first made in a body wall 902 of a patient, such as the abdominal wall. The inner ring 504 is compressed and the inner ring and sleeve 506 are manually inserted into the body cavity 904 through the incision 900 with the outer ring 502 remaining external to the body cavity. Once the inner ring 504 is within the body cavity 904, it expands around the inner surface of the incision 900 so as to be generally parallel to the outer surface of the abdominal wall 902. The sleeve 506 provides a working channel from outside the body cavity 904 to inside the body cavity. Retraction of the sleeve 506 can then be achieved by rolling the outer ring 502 over the sleeve 506 in a direction 700 as shown in FIG. 8 until a desired compression or wound opening is achieved. Incremental retraction is achieved by manually rolling the hollow tube 508 out of its coaxial alignment with the inner rod 510, i.e., the hollow tube 508 can be rolled and indexed to match the next alignment point between the hollow tube 508 and the inner rod 510.

The hollow tube 508 and the inner rod 510 lock in place when they are coaxially aligned, thereby preventing further indexing until the outer ring 502 is rolled out of its alignment again. This process is repeated until a desired retraction is achieved. Once surgery is complete, the wound retractor 500 can be retrieved by grabbing the inner ring 504 and the sleeve 506 and pulling them through the wound opening 900.

It is appreciated that the outer ring can be designed in various shapes and sizes to achieve various retraction rates and/or to conform to different body surfaces as illustrated in FIGS. 17a-17e. For example, the outer ring may include a single tube or multiple tubes of different shapes and sizes. The single or multiple tubes may be solid or include lumens of different shapes and sizes.

Similarly, the wound retractor having the roller design could be of various geometries. As illustrated in FIGS. 18a-18l, hollow tubes 508a-508l and inner rods 510a-510l, respectively, of the outer ring may have different shapes and sizes and may contain multiple locking mechanisms. For example, the inner rods 510b-510e and 510l have solid rectangular cross-sections. In comparison, the inner rods 510f-510k have hollow circular cross-sections. The hollow tubes and inner rods may be made of the same or different materials (e.g., soft and/or hard). For example, the inner rods may be rigid, such as a wire or piece of metal, or they may be flexible, such as an extension spring. The lumens of the hollow tubes 508a-508l may have cross-sections of different geometries such as fan-like geometry, circular, oval, circular with lumps, triangular, rectangular, any geometric shape with multiple sides, etc. Advantages of the above embodiments of the invention include improved retraction adjustability and stability.

Figure 19C:
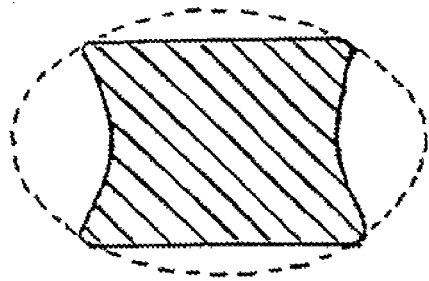
Figure 19D:
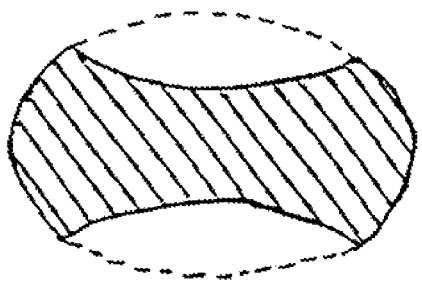
Figure 19E:
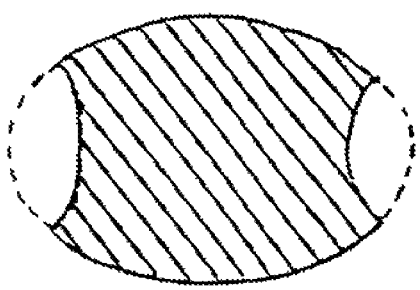
Figure 19F:
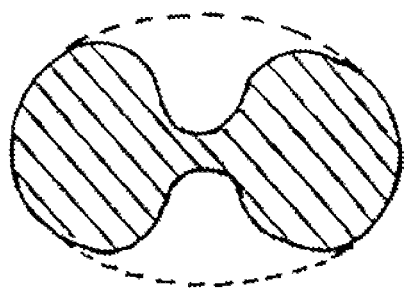
Figure 19G:
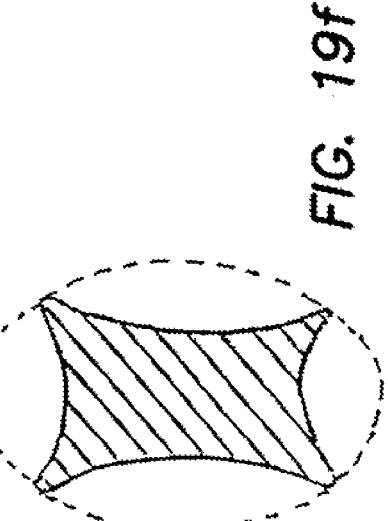
Figure 20B:
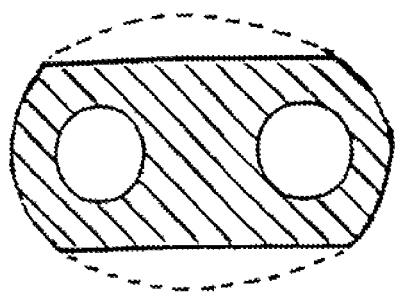
FIGS. 20a through 20g are section views of outer rings having generally prolate cross-sections and including lumens.
Figure 20A:
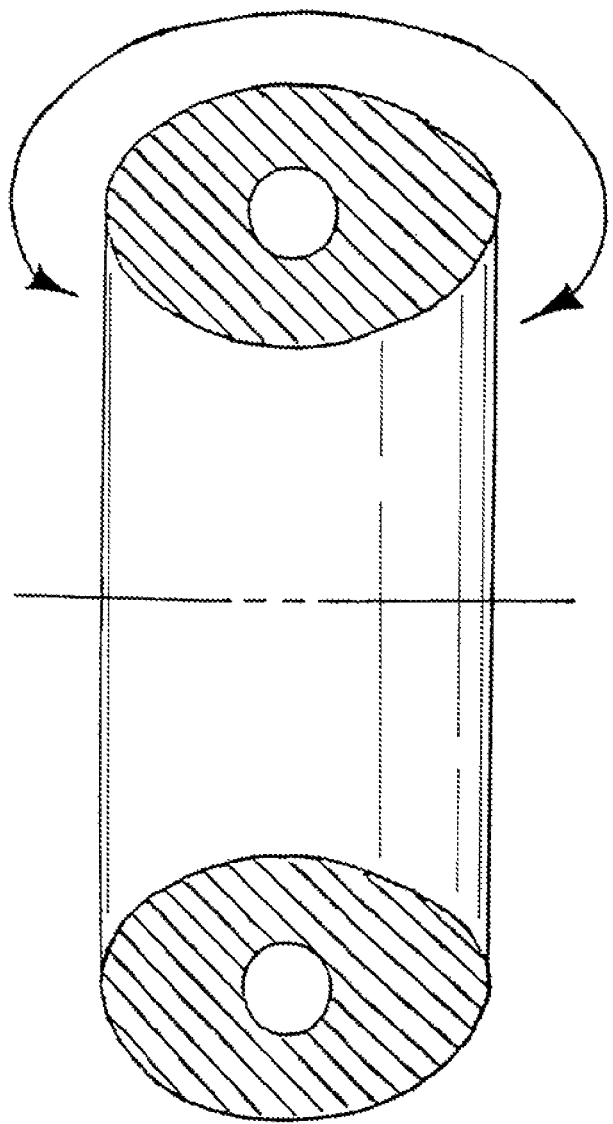
Figure 20E:
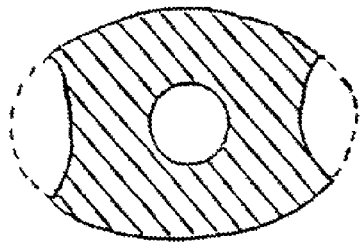
Figure 20D:
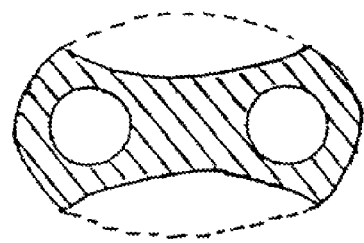
Figure 20C:
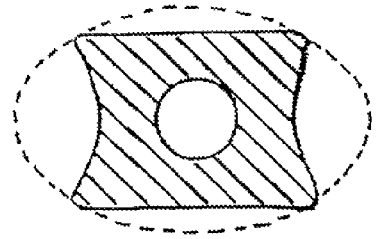
Figure 20G:
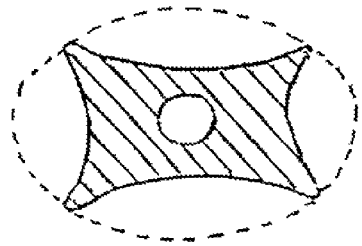
Figure 20F:
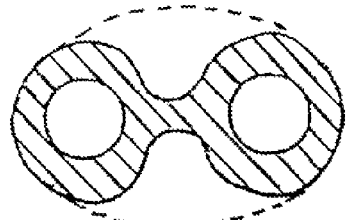

FIGS. 19a through 19g illustrate additional embodiments of the outer ring 190 of the invention having generally prolate cross-sections. The longer axis of the cross-section of the outer ring is generally parallel to an axis 92 of the outer ring as illustrated in FIG. 19a. The outer ring 190 can be turned around the axis 192 in either an outward or inward direction 800 to roll up the sleeve (not shown). The outer rings 190 of FIGS. 19*a*-19*g* provide tactile gripping and incremental rolling of the sleeve about the rings. FIG. 19*b* illustrates an outer ring 190 having two straight chordal surfaces 190*a* and 190*b* that are generally parallel to the axis 192. FIG. 19*c* illustrates an outer ring having two straight chordal surfaces and two curved chordal surfaces. FIGS. 19*d*-19*g* illustrate outer rings having at least two curved chordal surfaces.

FIGS. 20*a* through 20*g* illustrate outer rings of FIGS. 19*a*-19*g*, respectively, including at least one lumen in each ring. The lumen may house an inner rod (not shown) that deflects against the lumen wall, thereby providing audible feedback to the user. The lumen and inner rod may be of different geometries and sizes.

Figure 21C:
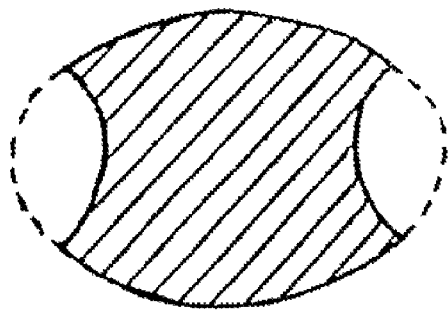
Figure 21D:
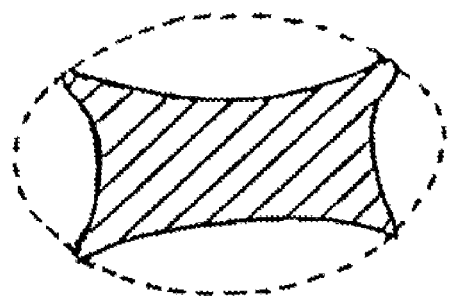
Figure 21E:
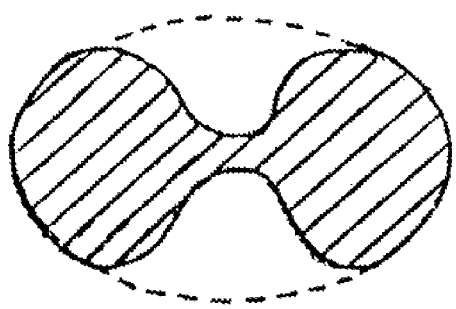
Figure 22B:
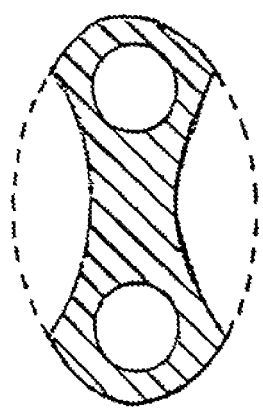
FIGS. 22a through 22e are section views of outer rings having generally oblate cross-sections and including lumens.
Figure 22A:
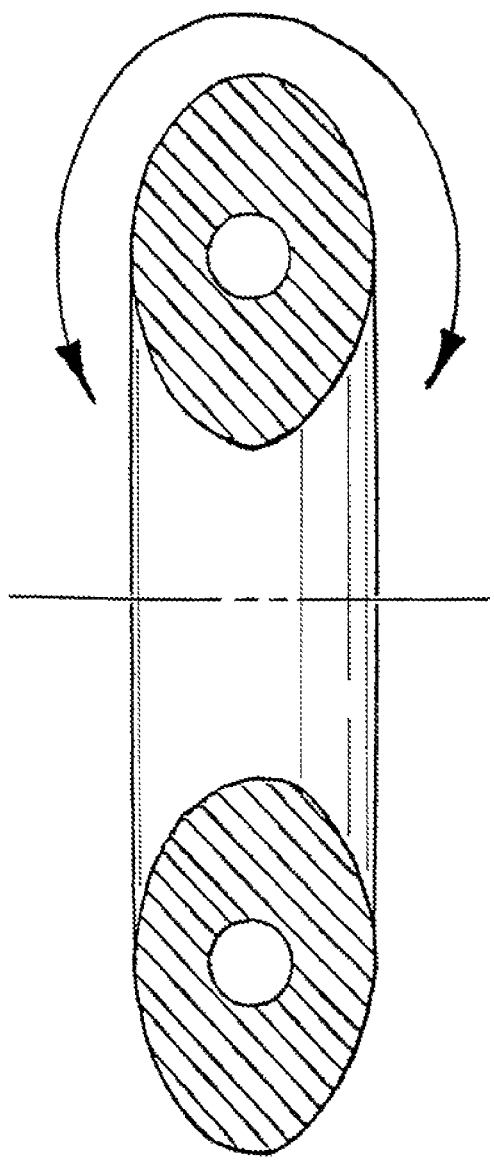
Figure 22C:
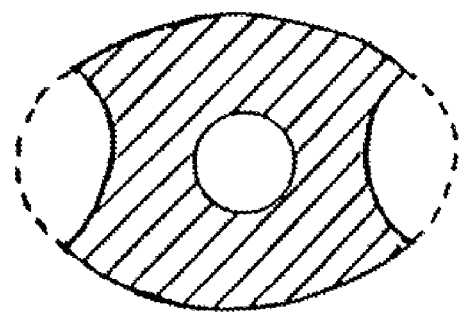
Figure 22D:
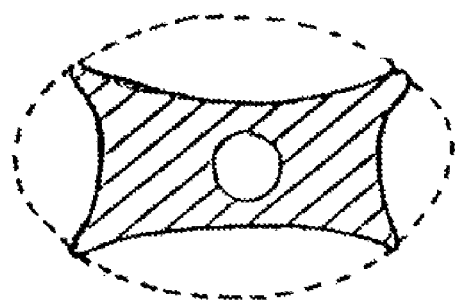
Figure 22E:
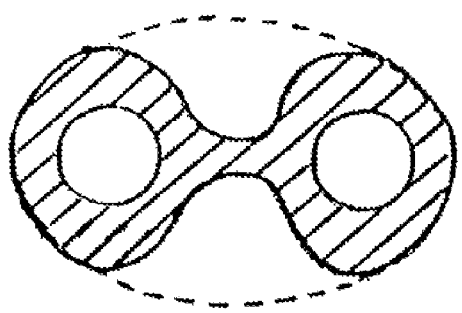

FIGS. 21*a* through 21*e* illustrate additional embodiments of an outer ring 194 of the invention having generally oblate cross-sections. The longer axis of the cross-section of the outer ring 194 is generally perpendicular to an axis 196 as illustrated in FIG. 21*a*. The outer ring 194 can be turned around the axis 196 in either an outward or inward direction 900 to roll up the sleeve (not shown). The outer rings of FIGS. 21*a*-21*e* provide tactile gripping and incremental rolling of the sleeve about the rings. FIGS. 21*b* through 21*e* illustrate outer rings having at least two curved chordal surfaces.

FIGS. 22*a*-22*e* illustrate the outer rings 194 of FIGS. 21*a*-21*e*, respectively, further including at least one lumen in each ring. The lumen may house an inner rod (not shown) that deflects against the lumen wall, thereby providing audible feedback to the user. The lumen and inner rod may be of different geometries and sizes.

FIG. 23*a* illustrates another embodiment of the outer ring of the invention having a triangular cross-section, and FIG. 23*b* illustrates the outer ring of FIG. 23*a* including a lumen. In another embodiment of the invention, FIG. 24*a* illustrates the outer ring of the invention having an odd number of sides, such as a pentagon, and FIG. 24*b* illustrates the outer ring of FIG. 24*a* including a lumen. These outer rings provide tactile gripping and incremental rolling of the sleeve about the rings. The lumens of the outer rings in FIGS. 23*b* and 24*b* may be of different shapes and sizes to house inner rods (not shown) having different shapes and sizes. It is appreciated that the outer ring can be designed in various shapes and sizes to achieve various retraction rates and/or to conform to different body shapes.

Figure 25A:
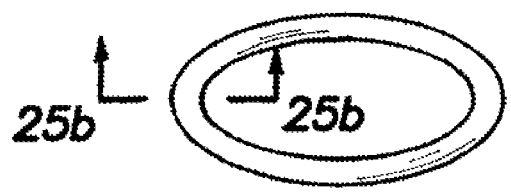
FIGS. 25a through 25b illustrate a process of forming the outer ring.
Figure 25B:
Figure 25C:
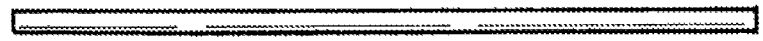
FIGS. 25c through 25e illustrate a process of forming the outer ring.
Figure 25D:
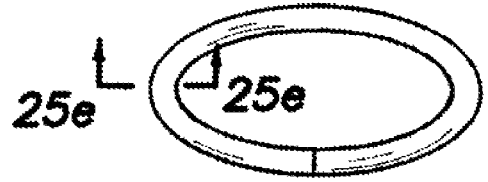
Figure 25E:

FIGS. 25*a* through 25*e* illustrate different processes of forming the outer ring of the invention. The outer ring, which may be solid (FIG. 25*b*) or include a lumen (FIG. 25*e*), may be molded as a circular ring as shown in FIGS. 25*a* and 25*b*, or the outer ring may be formed by joining a single or multiple extruded tubes into a circular ring as shown in FIGS. 25*c*-25*e*.

In another embodiment of the invention, access into and out of a patient's body is achieved by a hand assisted laparoscopic (HAL) procedure using a surgical access device such as the Gelport™ device as described in applicants' international application PCT/US01/29682, filed on Sep. 21, 2001, entitled "Surgical Access Apparatus and Method," which is incorporated herein by reference, while retraction is provided by the wound retractor of the present invention. The purpose of this embodiment is to combine the features and advantages of both the wound retractor of the present invention and the surgical access device as described in the PCT application. As explained in the PCT application, the current surgical access device uses a polyisoprene sheath that is wrapped distally around an O-ring, and once placed into a wound incision, the sheath is then stretched over extended tabs onto an abdominal base. The sheath of the surgical access device requires stretching and often times requires multiple attempts to secure it to the abdominal base. A novelty of this embodiment is to modify the cap and/or the abdominal base of the surgical access device so that it will accept the wound retractor of the present invention to replace the polyisoprene sheath and to maintain an airtight seal. The use of the wound retractor would simplify the HAL procedure and would not require stretching.

Figure 26:
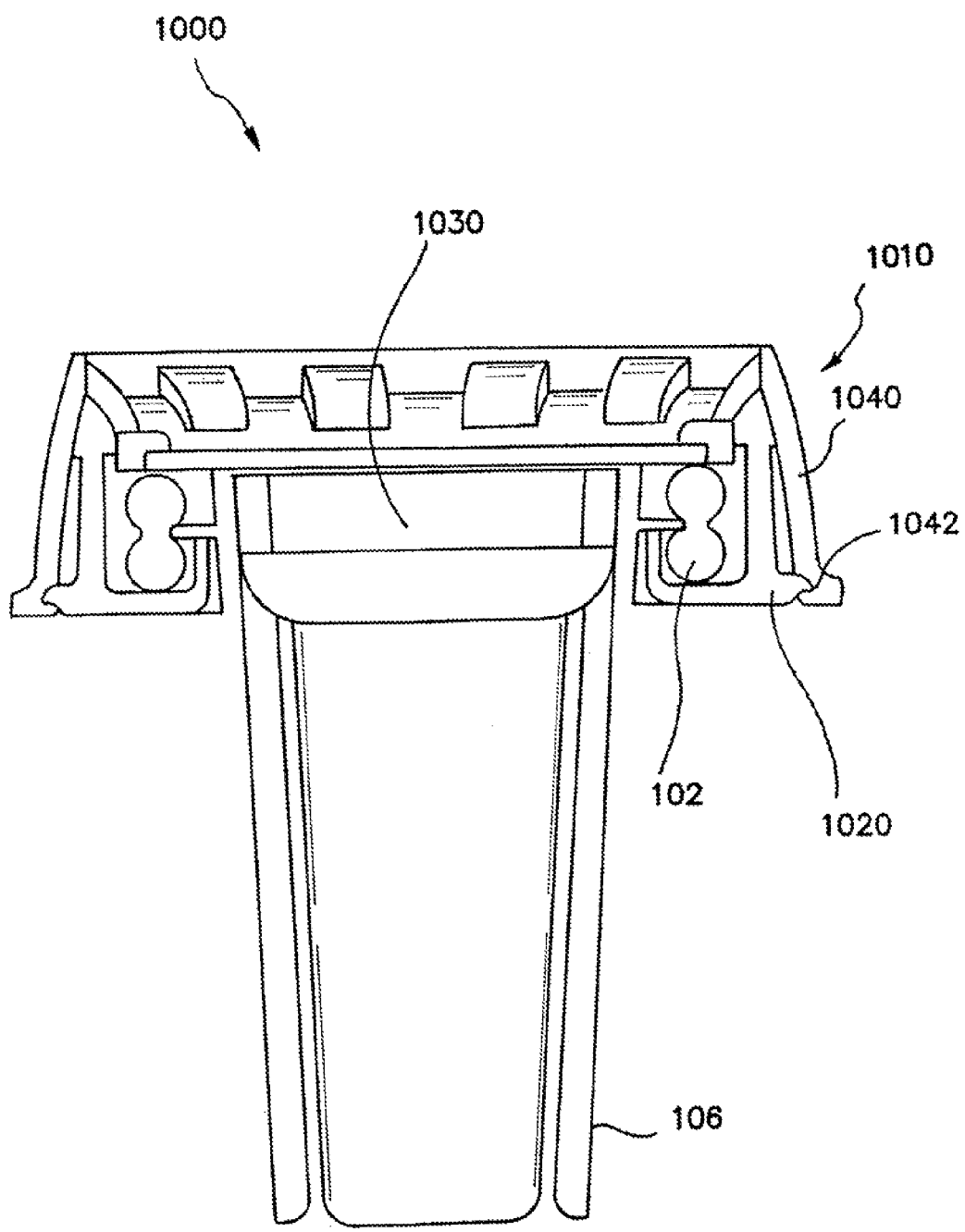
FIG. 26 is a section view of a surgical access device with a slightly modified gel cap and/or abdominal base.
Figure 27:
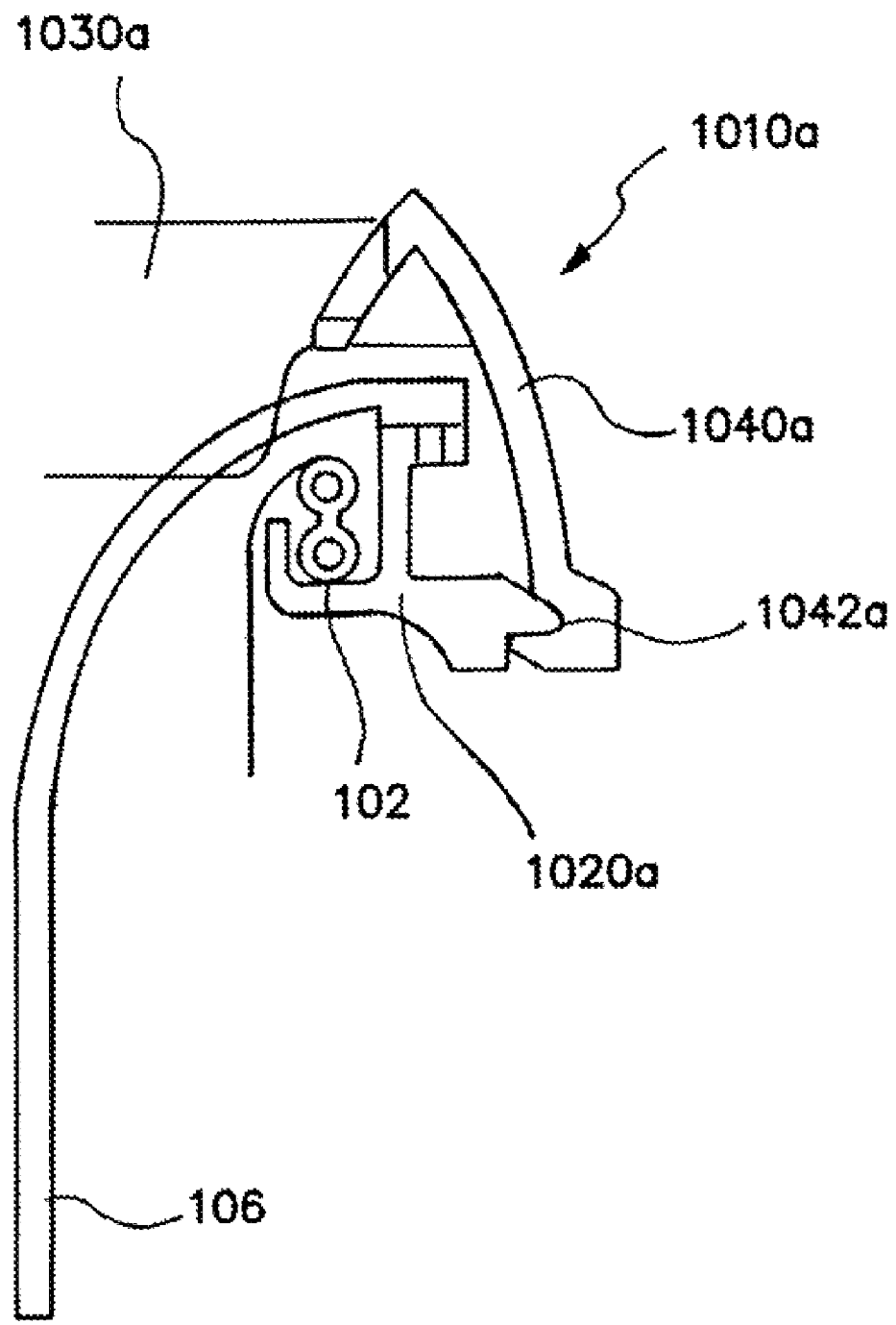
FIG. 27 is a section view of a surgical access device.
Figure 28:
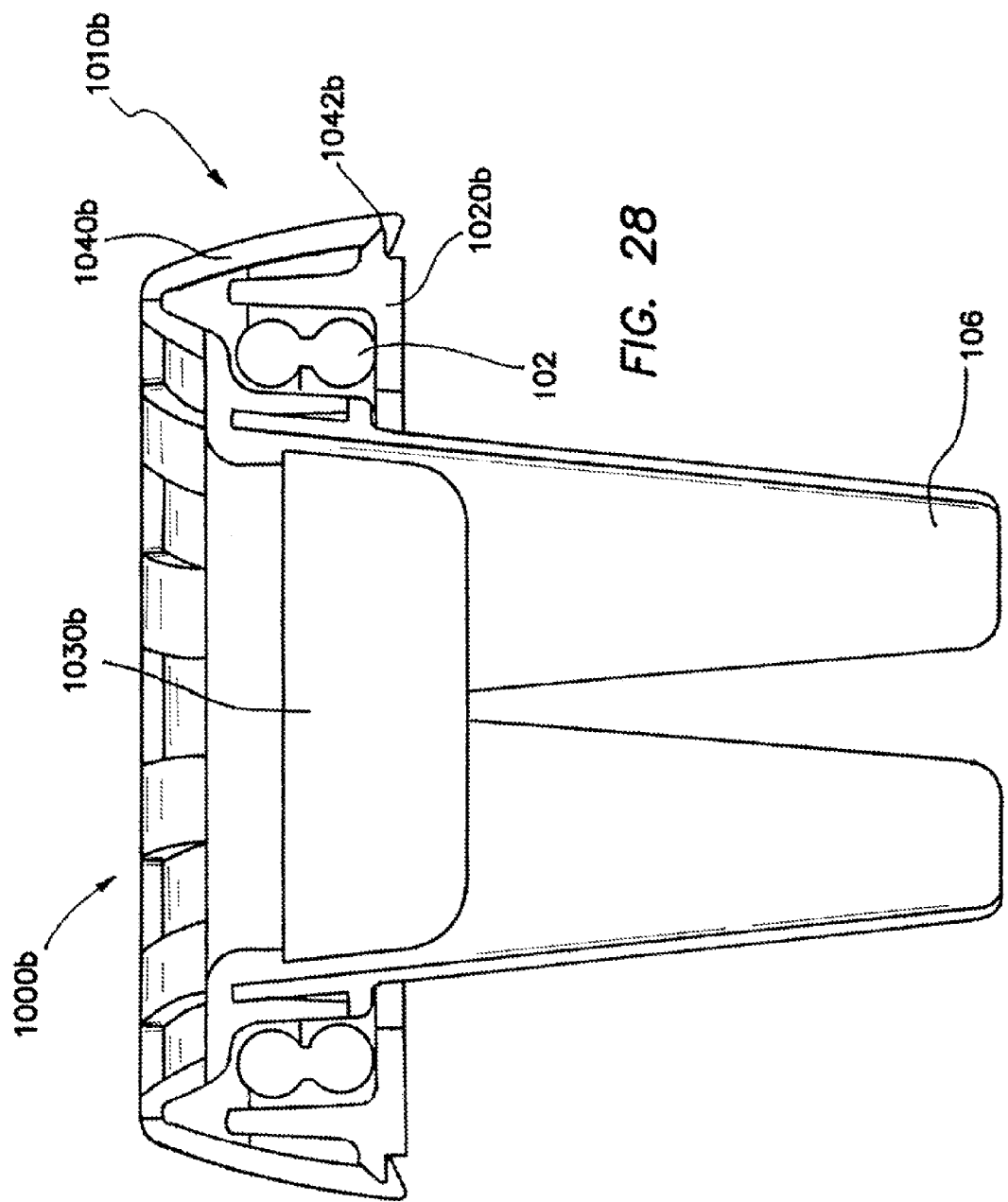
FIGS. 28-30 illustrate modifications that could be made to the gel cap and/or the abdominal base so that the surgical access device can be used with the wound retractor.
Figure 29:
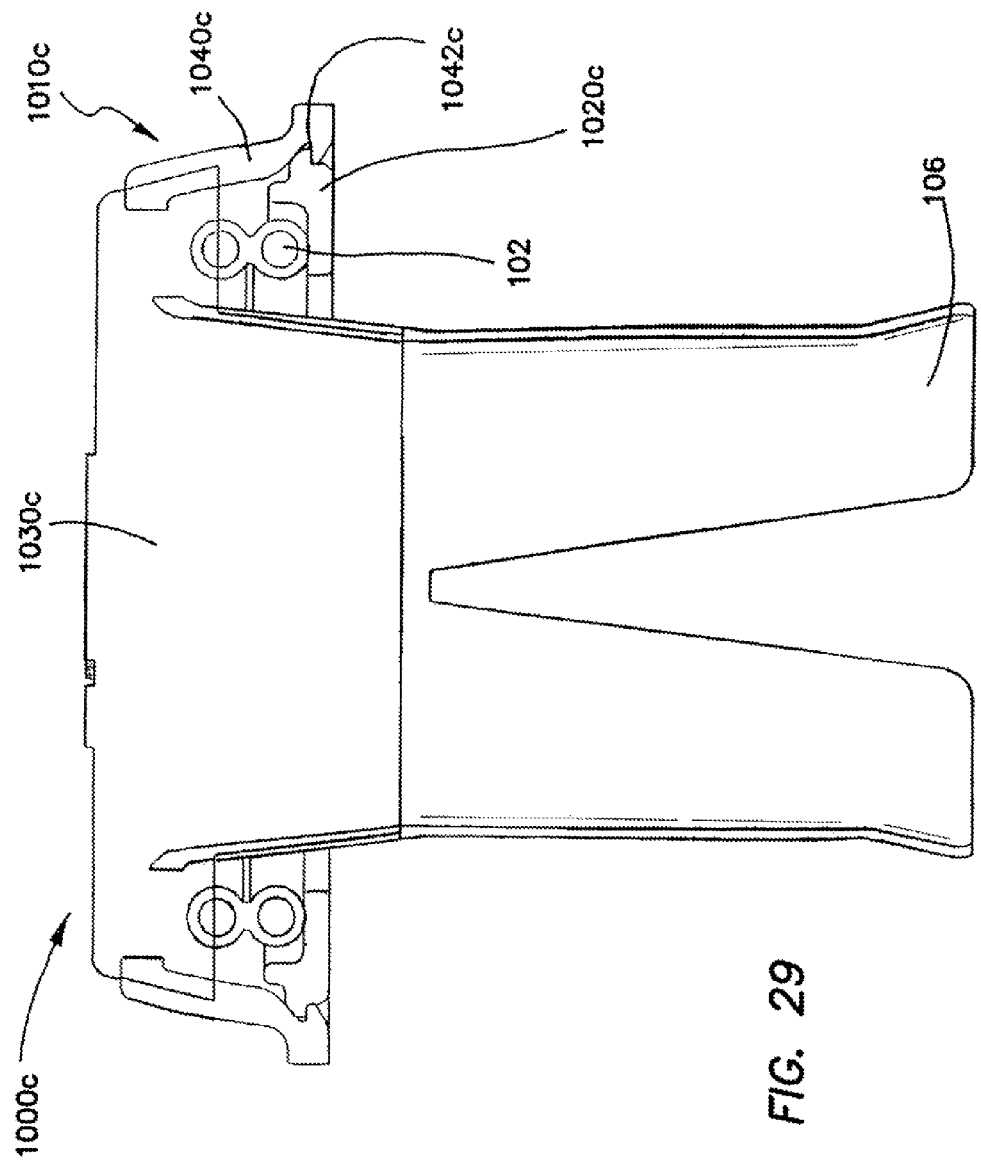
Figure 30:
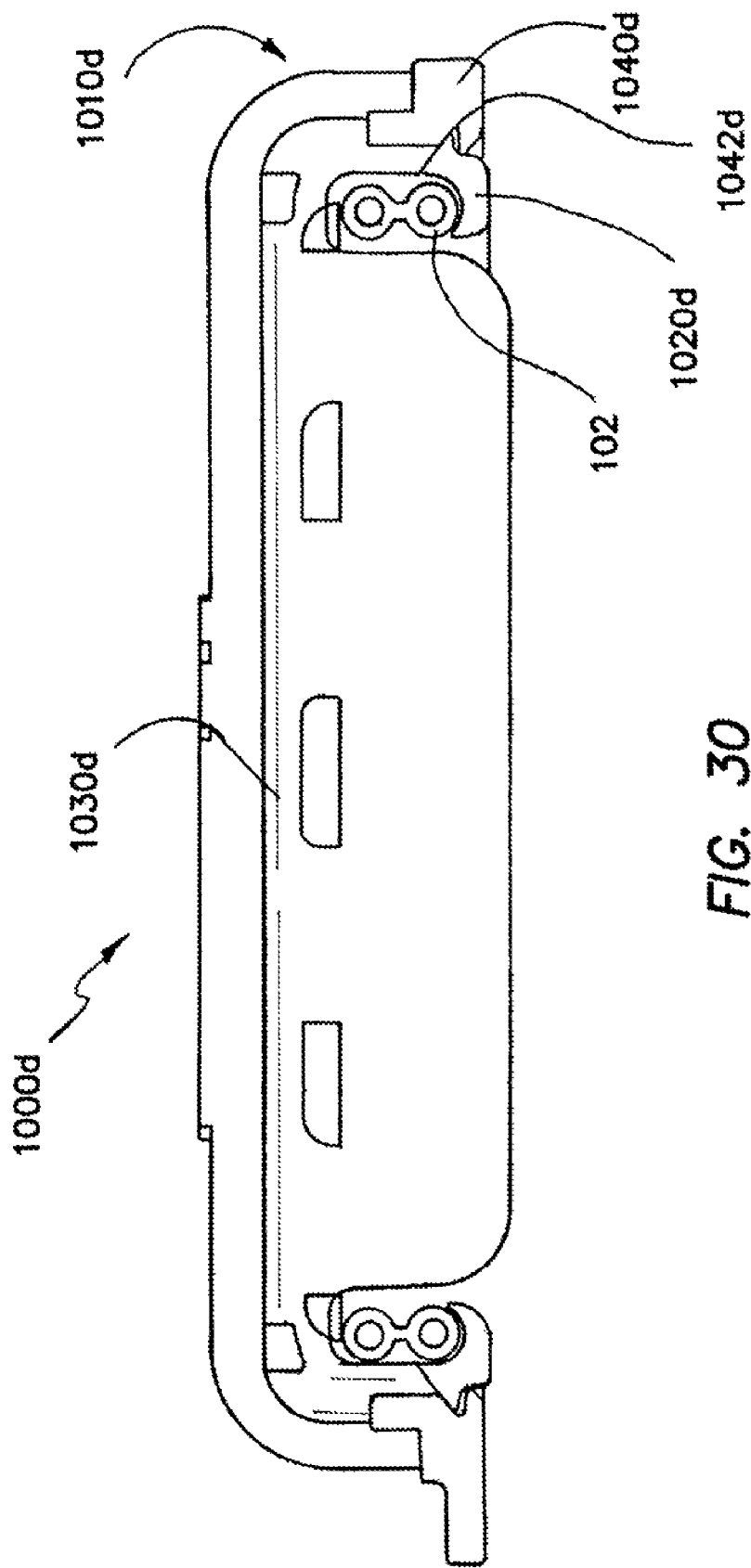

Referring to FIG. 26, there is shown a surgical access device 1000 with slight or moderate modifications to a gel cap 1010 and to an abdominal base 1020. The gel cap 1010 further includes a gel pad 1030 and a circumferential cap ring 1040, which can be inserted and molded to the pad 1030. The resulting gel cap 1010 forms a seal with the base 1020 and defines a working channel through the pad 1030, the cap ring 1040, the base 1020, and the sleeve 106 of the wound retractor. In this manner, the working channel includes a single valve formed by the gel pad 1030 that provides both a zero seal and an instrument seal for a wide range of instrument diameters. Referring to FIG. 27, the gel cap 1010*a* includes an annular void 1042*a* that is formed on the inner circumference of cap ring 1040*a*. The void 1042*a* is of particular advantage in forming a sealing relationship with a base 1020*a*. FIGS. 28-30 illustrate additional exemplary embodiments of the invention having modifications that could be made to the gel cap and/or the abdominal base so that the surgical access device can be used with the wound retractor.

Figure 31:
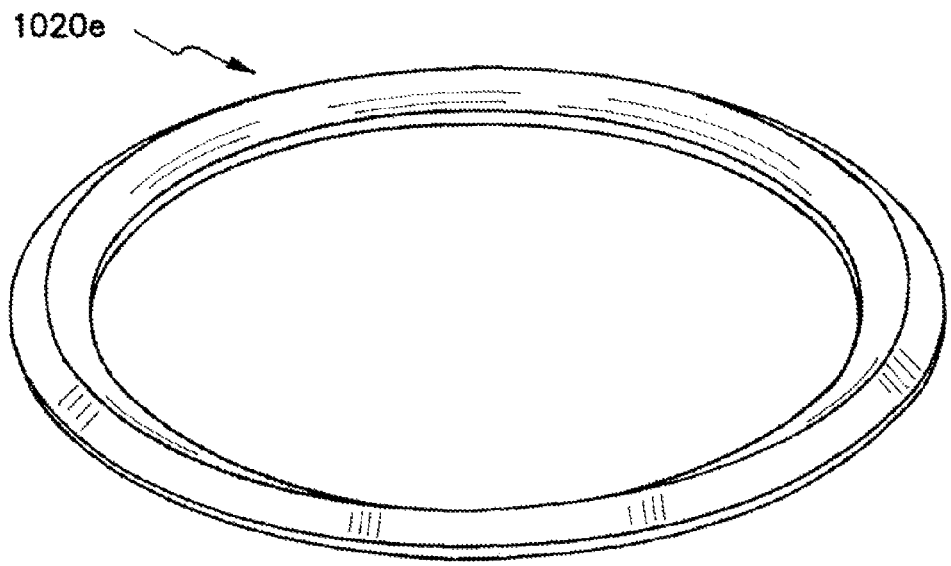
FIG. 31 is a perspective view of a base of a surgical access device.
Figure 32:
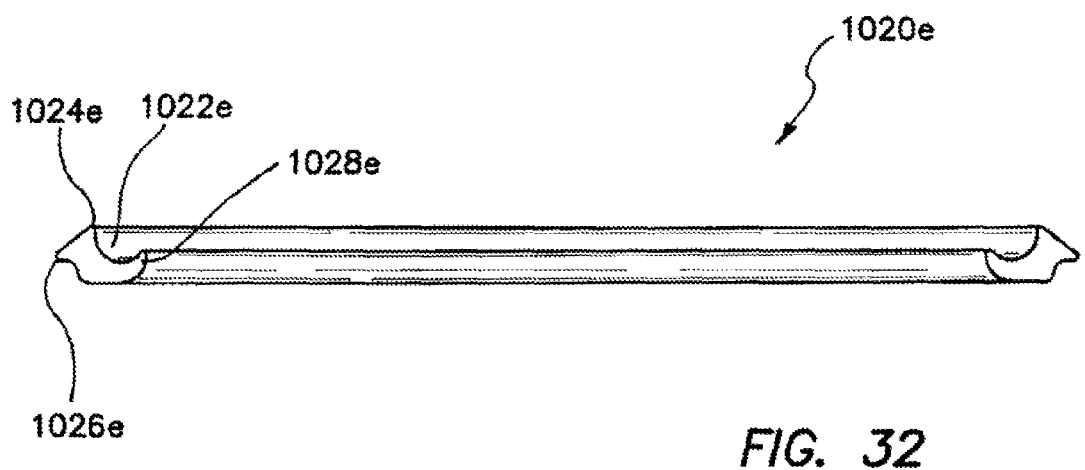
FIG. 32 is a section view of the embodiment illustrated in FIG. 31.

FIG. 31 illustrates a perspective view of a base 1020*e* in accordance with another embodiment of the invention. FIG. 32 is a section view of the embodiment illustrated in FIG. 31. From these views, it will be noted that the base 1020*e* can be provided with a smooth, generally cylindrical inner surface 1022*e* which extends proximally to a rounded end surface 1024*e* and outwardly from the end surface 1024*e* along an annular lip 1026*e*, which is sized and configured to fit into an annular void formed on the inner circumference of a corresponding cap ring. Proximal to the inner surface 1022*e*, the base 1020*e* can also include a rounded end surface 1028*e* along its inner diameter for securing the outer ring of the wound retractor once the sleeve has been shortened.

Figure 33:
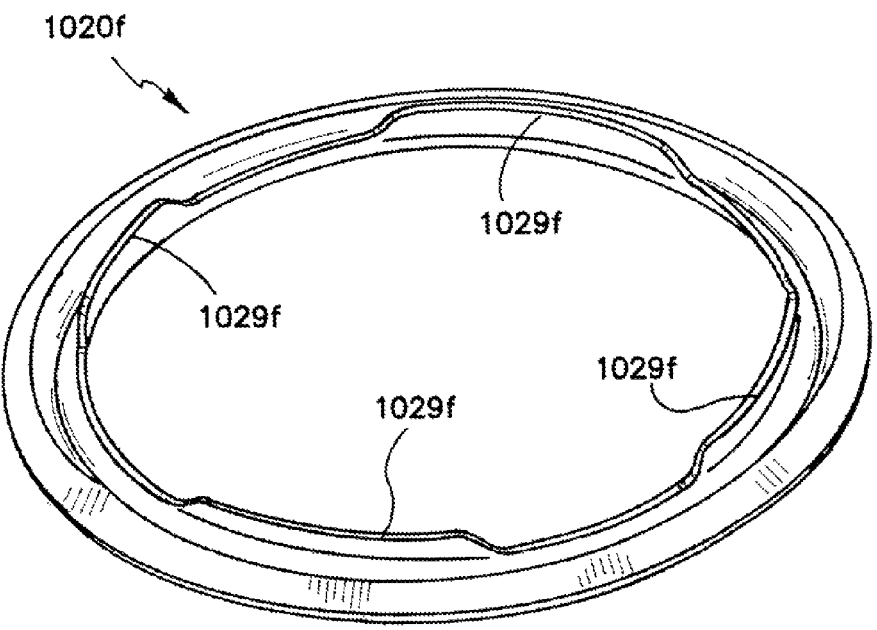
FIGS. 33 and 34 illustrate a base of a surgical access device having at least one toggle or latch adapted to fit a corresponding cap ring.
Figure 34:
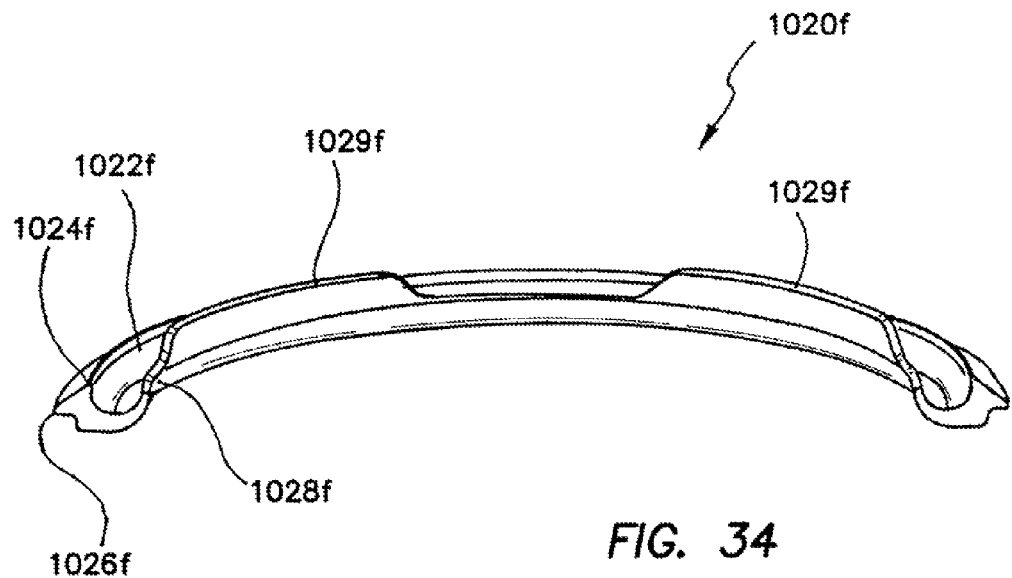
Figure 35:
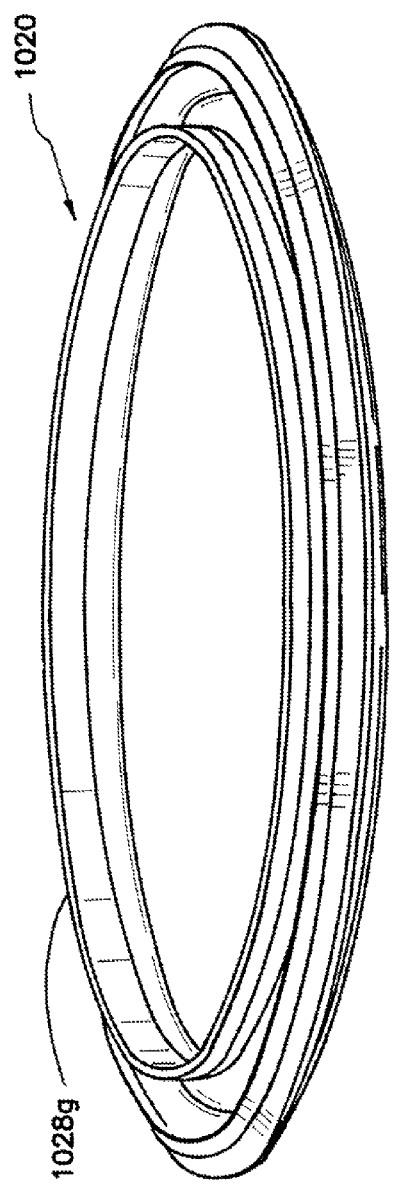
FIGS. 35 and 36 illustrate a base of a surgical access device having a raised wall on an inner diameter and adapted to fit a corresponding cap ring.
Figure 36:
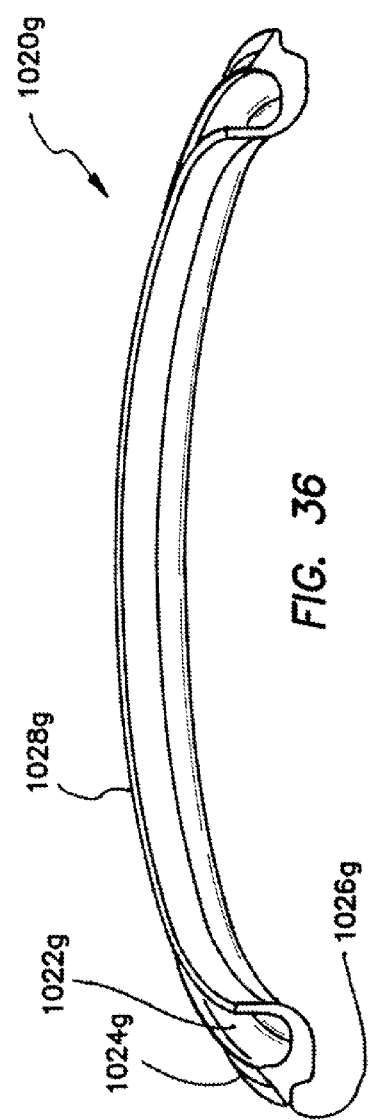

In another embodiment of the invention, FIGS. 33 and 34 illustrate a base 1020*f* having a smooth generally cylindrical inner surface 1022*f*, a rounded end surface 1024*f*, an annular lip 1026*f*, and an end surface 1028*f* having at least one toggle or latch 1029*f* sized and configured to fit a corresponding cap ring. In this embodiment, the toggle or latch 1029*f* operates to change the inner diameter of the cap ring to create a seal or release the cap ring from the base. In yet another embodiment of the invention, FIGS. 35 and 36 illustrate a base 1020*g* having a smooth generally cylindrical inner surface 1022*g*, a rounded end surface 1024*g*, an annular lip 1026*g*, and an end surface 1028*g* having a raised wall sized and configured to fit a corresponding cap ring.

Figure 37:
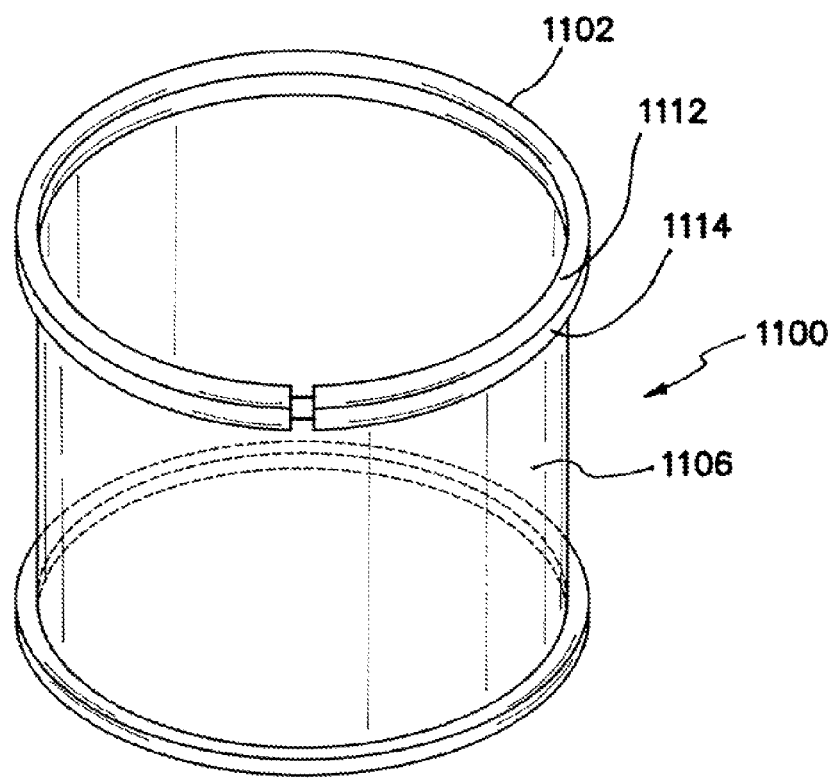
FIG. 37 is a perspective view of a wound retractor having a double-tube outer ring with a rigid, noncompliant hoop positioned in each of the circular tubes of the outer ring.
Figure 38:
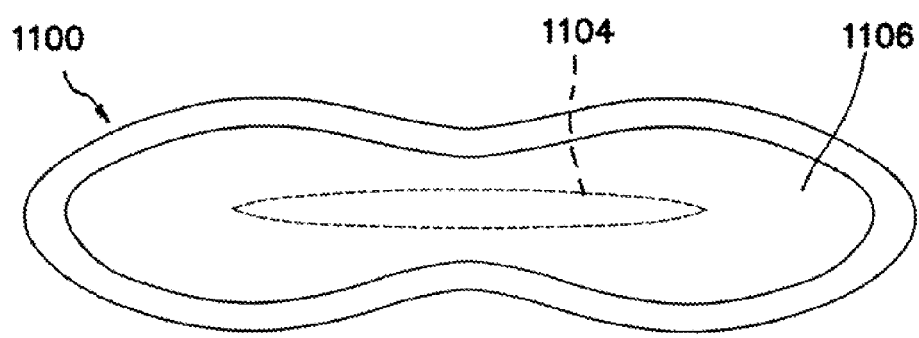
FIG. 38 is a plan view of the wound retractor of FIG. 37 disposed in a wound in a biological body wall with the outer ring of the wound retractor not having the rigid, noncompliant hoops positioned in the circular tubes of the outer ring.

Referring to FIGS. 37 and 38, other embodiments of a retractor 1100 include a double-tube outer ring 1102 that is formed of a material having a low durometer. The double-tube outer ring 1102 may be made of an elastomeric material, such as a low durometer polymeric material. The elastomeric material for forming the double-tube outer ring 1102 may include Kraton. The low durometer material of the double-tube outer ring 1102 does not have sufficient strength to adequately retract a wound 1104 without the inclusion of a hoop placed within the outer ring. As depicted in FIG. 38, without a hoop within the outer ring 1102, a sleeve 1106 of the retractor 1100 remains substantially closed when deployed through the wound 1104. Similar to previously described embodiments, the double-tube outer ring 1102 includes a first circular tube 1112 and a second circular tube 1114. The first and second circular tubes 1112, 1114 may each include a lumen.

Figure 39:
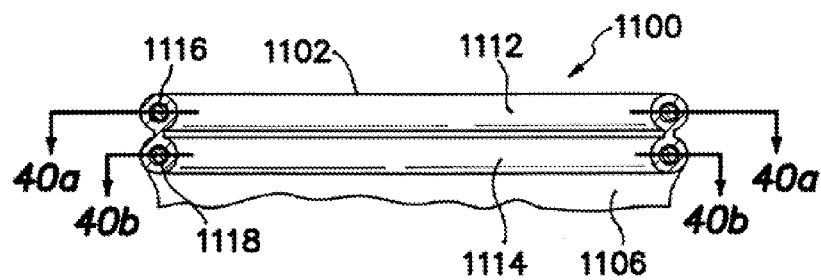
FIG. 39 is a side section view of the double-tube outer ring of the wound retractor having a continuous hoop in one of the circular tubes of the outer ring and a split hoop in the other circular tube with the ends of the split hoop abutting each other.
Figure 40A:
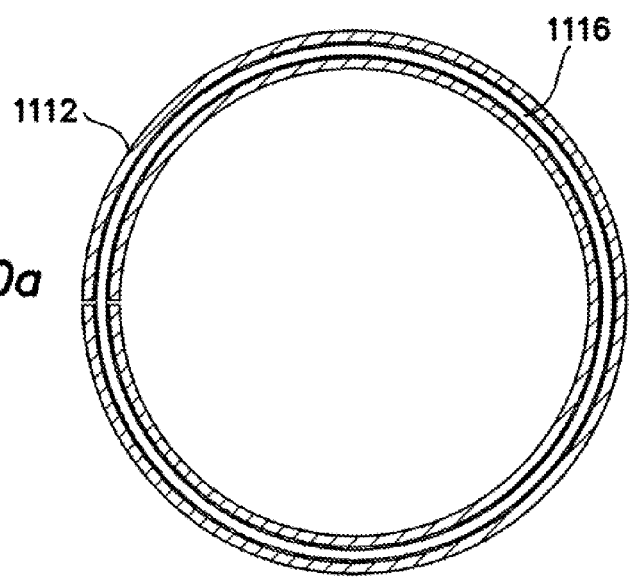
FIG. 40a is a section view taken from line 40a-40a in FIG. 39 and showing the continuous hoop in a circular tube of the outer ring.
Figure 40B:
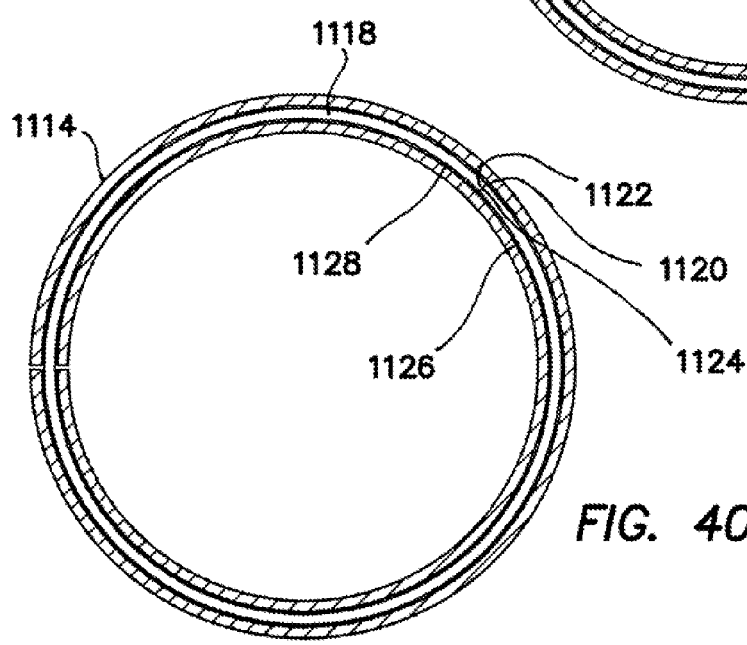
FIG. 40b is a section view taken from line 40b-40b in FIG. 39 and showing the split hoop in a circular tube of the outer ring.

Referring to FIGS. 39-40, the double-tube outer ring 1102 of the wound retractor 1100 may include a substantially rigid, noncompliant, first continuous hoop 1116 in the first circular tube 1112 of the outer ring. The lumen of the second circular tube 1114 may include a substantially noncompliant, second split hoop 1118 therein. The split hoop 1118 includes a hoop having a single split 1120 about its circumference with the split creating a first end 1122 of the split hoop and a second end 1124 of the split hoop. In its neutral position, the first and second ends 1122, 1124 substantially abut each other. As will be discussed below, the split 1120 in the hoop 1118 permits the circumference of the split hoop 1118 to expand and contract when rolling the sleeve 1106 around the outer ring.

As shown in FIGS. 25c through 25e, the outer ring 1102 may be formed by transforming an extruded elastomeric tube into a circular ring. To place the continuous hoop 1116 into the first circular tube 1112, the hoop may include a split that produces at least a first and second end. One of the first and second ends of the hoop 1116 may be fed into the lumen of the first circular tube 1112 and continually fed until substantially the entire hoop 1116 is within the lumen of the first circular tube. The at least first and second ends of the hoop 1116 may then be joined together to form the continuous hoop 1116. The at least first and second ends of the hoop 1116 may be joined by welding, brazing, mechanical means, or any other means that is well known in the art. The split hoop 1118 may be placed into the second circular tube 1114 in similar fashion to placing the continuous hoop 1116 into the first circular tube 1112, except that the first and second ends 1122, 1124 of the split hoop are not subsequently joined together.

Figure 41A:
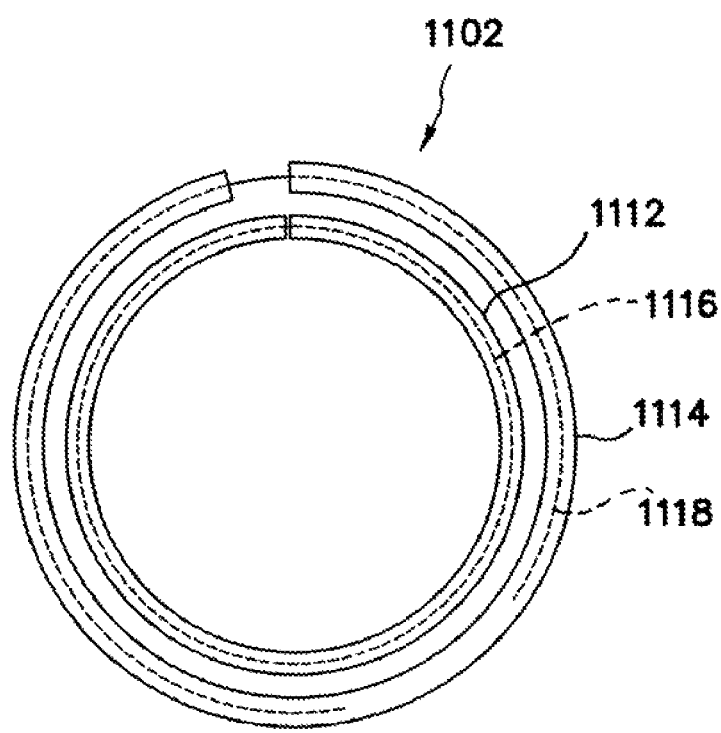
FIGS. 41a and 41b depict the circular tube having the split hoop of FIG. 39 being turned around the circular tube having the continuous hoop.
Figure 41B:
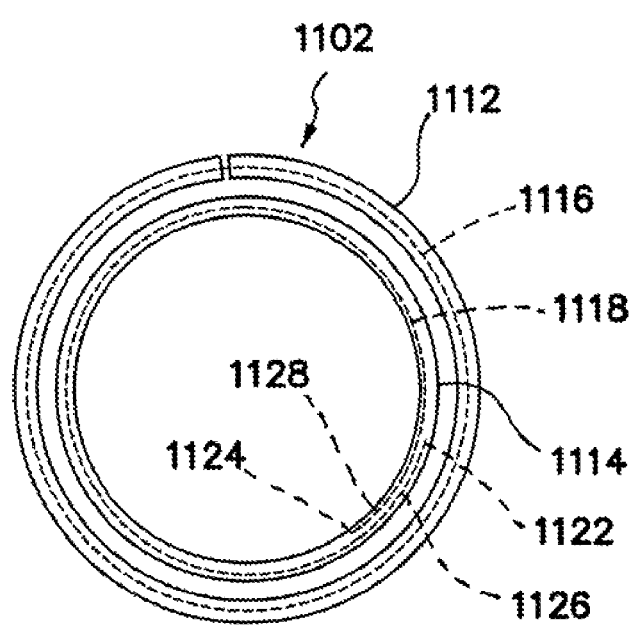
Figure 42:
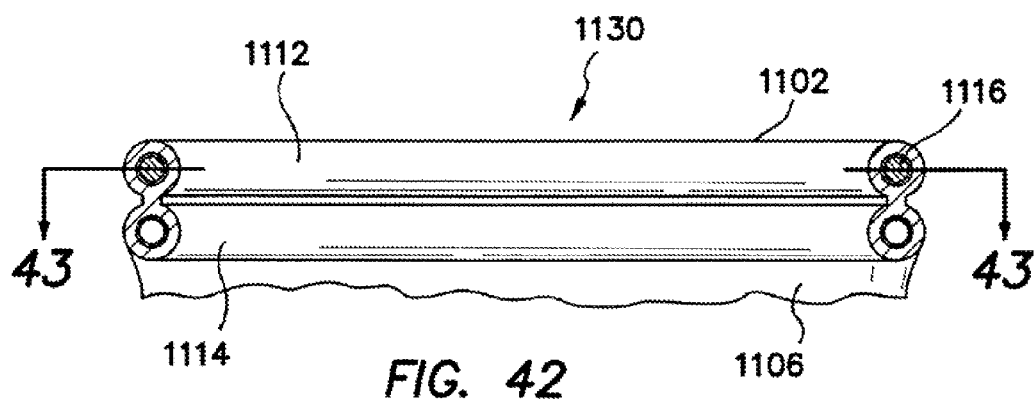
FIG. 42 is a side section view of the double-tube outer ring of the wound retractor having a continuous hoop in one of the circular tubes of the outer ring and the lumen of the other circular tube being hollow.
Figure 43:
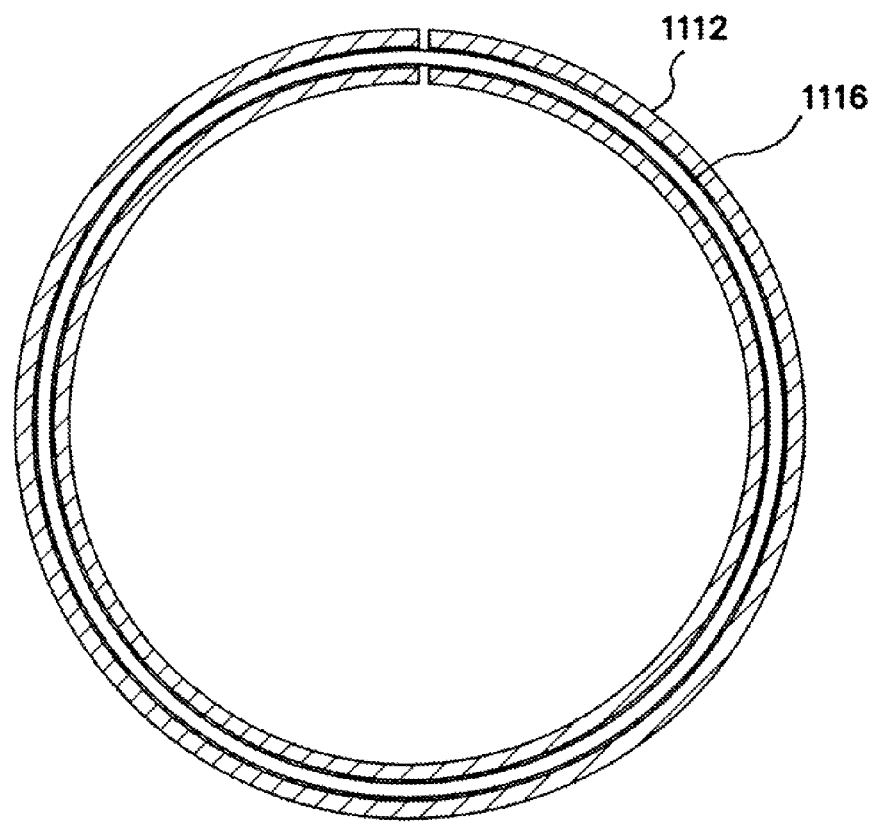
FIG. 43 is a section view taken from line 43-43 in FIG. 42 and showing the continuous hoop in a circular tube of the outer ring.
Figure 44:
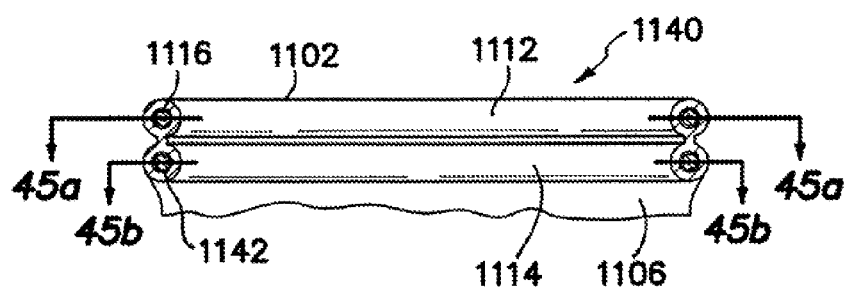
FIG. 44 is a side section view of the double-tube outer ring of the wound retractor having a continuous hoop in one of the circular tubes of the outer ring and a split hoop in the other circular tube with a space between the ends of the split hoop.
Figure 45A:
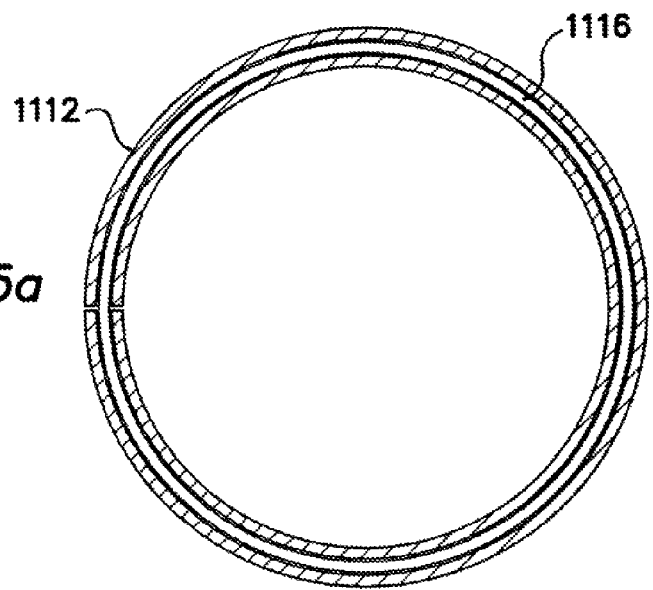
FIG. 45a is a section view taken from line 45a-45a in FIG. 44 and showing the continuous hoop in a circular tube of the outer ring.
Figure 45B:
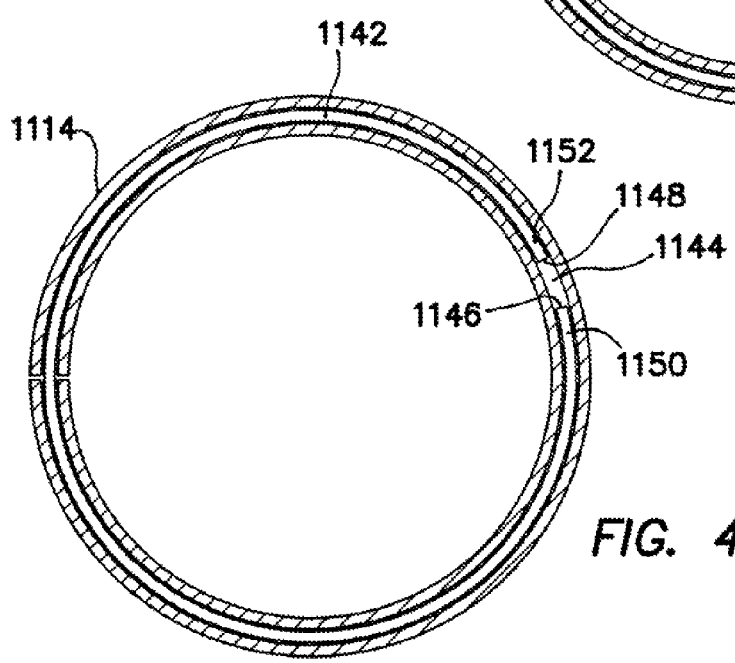
FIG. 45b is a section view taken from line 45b-45b in FIG. 44 and showing the split hoop in a circular tube of the outer ring.
Figure 46:
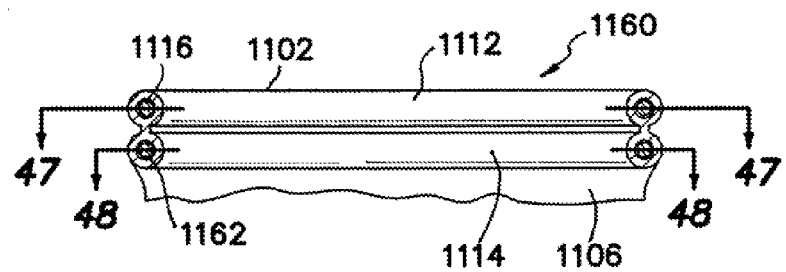
FIG. 46 is a side section view of the double-tube outer ring of the wound retractor having a continuous hoop in one of the circular tubes of the outer ring and a split hoop in the other circular tube with the split hoop having more than one split and the ends of the split hoop abutting each other.
Figure 47:
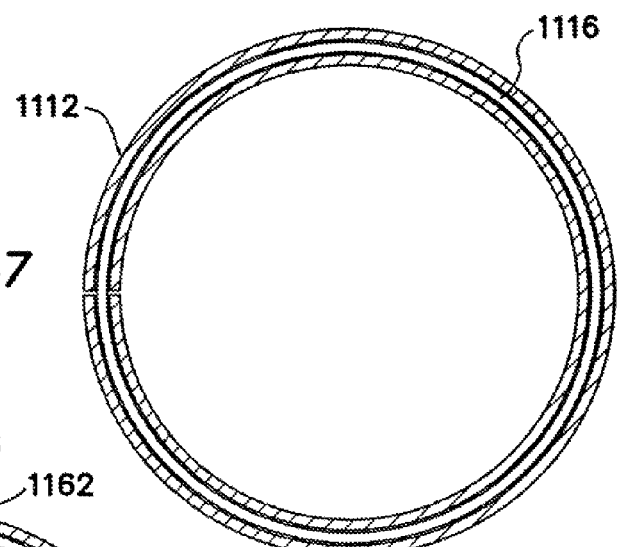
FIG. 47 is a section view taken from line 47-47 in FIG. 46 and showing the continuous hoop in a circular tube of the outer ring.
Figure 48:
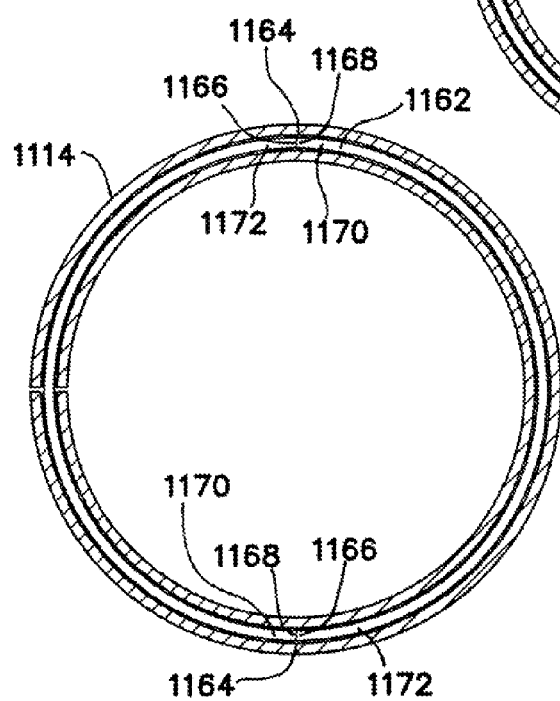
FIG. 48 is a section view taken from line 48-48 in FIG. 46 and showing the split hoop in a circular tube of the outer ring.
Figure 49:
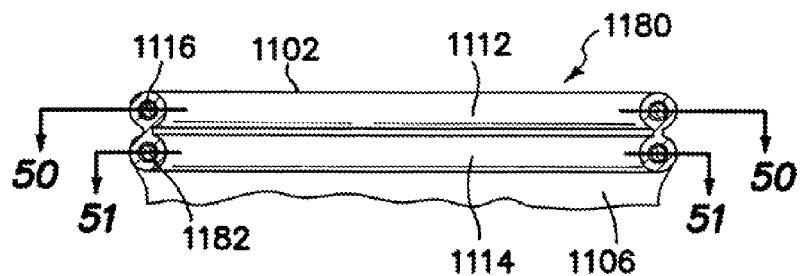
FIG. 49 is a side section view of the double-tube outer ring of the wound retractor having a continuous hoop in one of the circular tubes of the outer ring and a split hoop in the other circular tube with the split hoop having more than one split and spaces between the ends of the split hoop.
Figure 50:
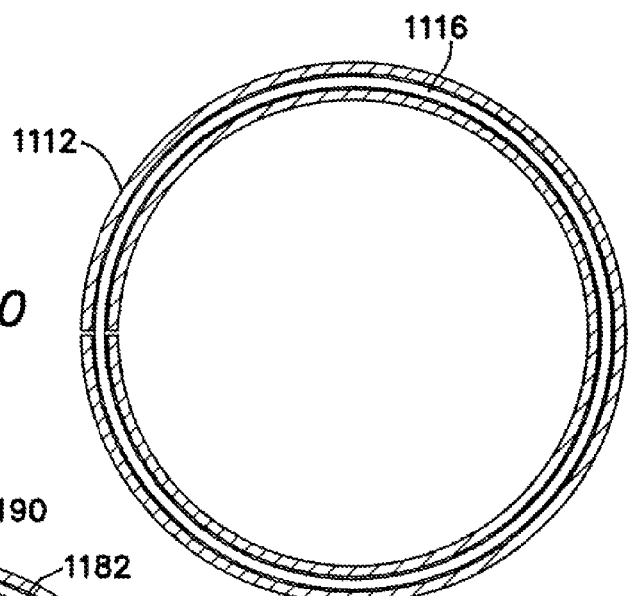
FIG. 50 is a section view taken from line 50-50 in FIG. 49 and showing the continuous hoop in a circular tube of the outer ring.
Figure 51:
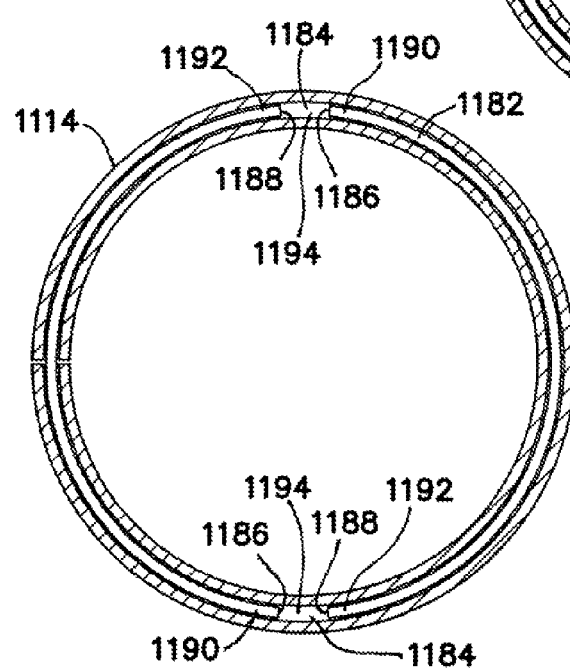
FIG. 51 is a section view taken from line 51-51 in FIG. 49 and showing the split hoop in a circular tube of the outer ring.

Referring to FIGS. 41a and 41b, with the first circular tube 1112 including the substantially rigid, noncompliant, continuous hoop 1116 within its lumen, rolling the sleeve 1106 around the outer ring 1102 includes turning the second circular tube 1114, which has the split hoop 1118 within the lumen, about the first circular tube 1112. The first, continuous hoop 1116 functions as an axle about which the outer ring 1102 is turned. The circumference of the second, split hoop 1118 expands when it is turned outside of the first circular tube 1112 and contracts when it is turned inside of the first circular tube 1112. To facilitate contraction of the circumference of the split hoop 1118, the lumen of the second circular tube 1114 is sufficiently larger than the cross-sectional periphery of the split hoop to permit the first and second ends 1122, 1124 of the split hoop to offset from each other and permit a first end portion 1126 and a second end portion 1128 of the split hoop to overlap each other. Alternatively, the second circular tube 1114 may be formed of a material having sufficient elasticity to stretch and permit the first and second end portions 1126, 1128 to overlap each other.

The substantially noncompliant hoops 1116, 1118 may be made of metals, such as stainless steel, piano wire heat treated to a spring temper, or other metals that produce a substantially noncompliant hoop. The substantially noncompliant hoops 1116, 1118 may also be formed of rigid polymeric materials through molding, machining, and other processes that are well known in the art. The substantially noncompliant hoops 1116, 1118 may also be formed of other suitable rigid materials that are well known in the art.

In comparison to retractors of the prior art, the substantially noncompliant hoop in a lumen of the outer ring provides greater strength, which in turn provides better retraction. The substantially noncompliant hoop controls the shape of the wound opening, rather than the wound opening controlling the shape of the retractor. In this manner, the wound retractor of the present invention provides better isolation, protection, and sealing of the wound.

In an embodiment similar to the embodiment depicted in FIGS. 39-40, FIGS. 42 and 43 depict a wound retractor 1130 having a substantially rigid, noncompliant, continuous hoop 1116 in the first circular tube 1112 of the outer ring 1102 and the second circular tube 1114 having a hollow lumen. Having the lumen of the second circular tube 1114 hollow facilitates easier turning of the second circular tube 1114 about the first circular tube 1112 when rolling the sleeve 1106 around the outer ring 1102.

In another embodiment similar to the embodiment depicted in FIGS. 39-40, FIGS. 44-45 depict a wound retractor 1140 having a substantially rigid, noncompliant, first continuous hoop 1116 in the first circular tube 1112 of the outer ring 1102 and a second split hoop 1142 in the second circular tube 1114. However, the second split hoop 1142 in this embodiment includes a space 1144 between the first end 1146 and the second end 1148 of the split hoop. The space 1144 between the first and second ends 1146, 1148 of the split hoop 1142 may be sufficient to substantially prevent the first and second ends from contacting each other when the split hoop contracts while rolling the sleeve 1106 around the outer ring 1102. In this manner, it is not necessary to provide means for the first end portion 1150 and the second end portion 1152 of the second split hoop 1142 to overlap in the second circular tube 1114 when the circumference of the split hoop contracts during rolling of the sleeve 1106 around the outer ring 1102.

In a further embodiment similar to the embodiment depicted in FIGS. 39-40, FIGS. 46-48 depict a wound retractor 1160 having the substantially rigid, noncompliant, continuous first hoop 1116 in the lumen of the first circular tube 1112 and a substantially noncompliant second hoop 1162 having two or more splits 1164 about the circumference of the hoop 1162 in the lumen of the second circular tube 1114. The splits 1164 create first ends 1166 and second ends 1168 of each portion of the second split hoop 1162. The two or more splits 1164 may be substantially equally spaced about the circumference of the second split hoop 1162. Adjacent first and second ends 1166, 1168 of the split hoop 1162 substantially abut each other. Similar to the embodiment of FIGS. 39-40, the circumference of the second split hoop 1162 expands when it is turned outside of the first circular tube 1112 and contracts when it is turned inside of the first circular tube with first end portions 1170 of the split hoop and second end portions 1172 of the split hoop overlapping each other during the contraction phase.

In an additional embodiment similar to the embodiment depicted in FIGS. 39-40, FIGS. 49-51 depict a wound retractor 1180 having the substantially rigid, noncompliant, continuous first hoop 1116 in the lumen of the first circular tube 1112 and a substantially noncompliant second hoop 1182 having two or more splits 1184 about the circumference of the hoop 1182 in the lumen of the second circular tube 1114. The splits 1184 create first ends 1186, second ends 1188, first end portions 1190 and second end portions 1192 of each portion of the second split hoop 1182. The first and second ends 1186, 1188 of adjacent hoop portions of the second split hoop 1182 are separated by spaces 1194 that permit the circumference of the split hoop 1182 to expand and contract. Similar to the embodiment of FIGS. 44 and 45, the circumference of the second split hoop 1182 expands when it is turned outside of the first circular tube 1112 and contracts when it is turned inside of the first circular tube. The sum of the spaces 1194 may be sufficient to substantially prevent the first and second ends 1186, 1188 of adjacent hoop portions from contacting each other when the second split hoop 1182 contracts while rolling the sleeve 1106 around the outer ring 1102. Also similar to the embodiment of FIGS. 44 and 45, it is not necessary to provide means for the first end portions 1190 and the second end portions 1192 of the split hoop 1182 to overlap when the circumference of the split hoop contracts during rolling of the sleeve 1106 around the outer ring 1102.

Figure 52:
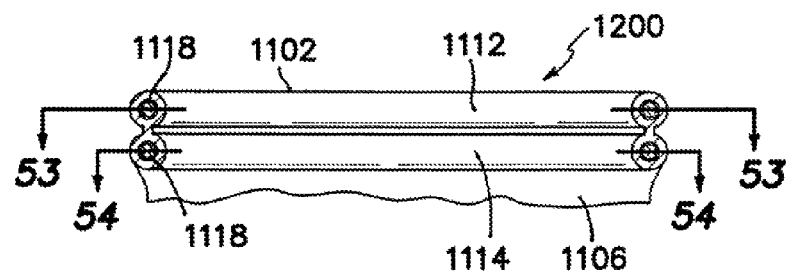
FIG. 52 is a side section view of the double-tube outer ring of the wound retractor having a split hoop in each of the circular tubes of the outer ring with the split hoops each having a single split with the ends of each of the hoops abutting each other.
Figure 53:
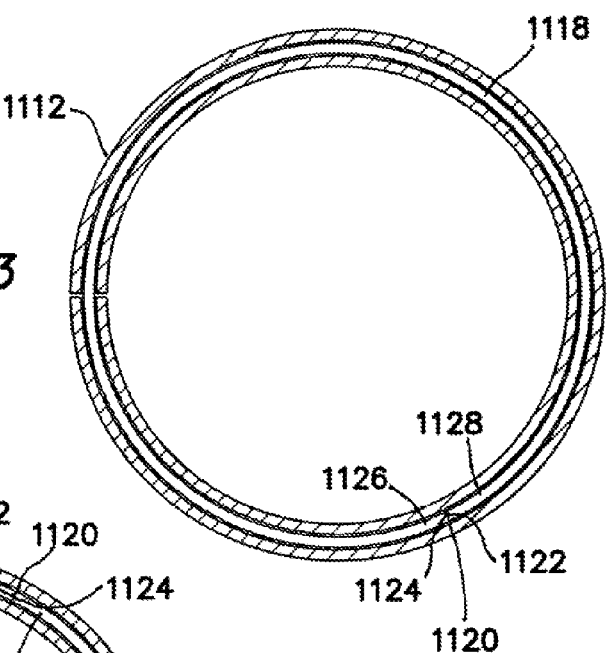
FIG. 53 is a section view taken from line 53-53 in FIG. 52 and showing the split hoop in a circular tube of the outer ring.
Figure 54:
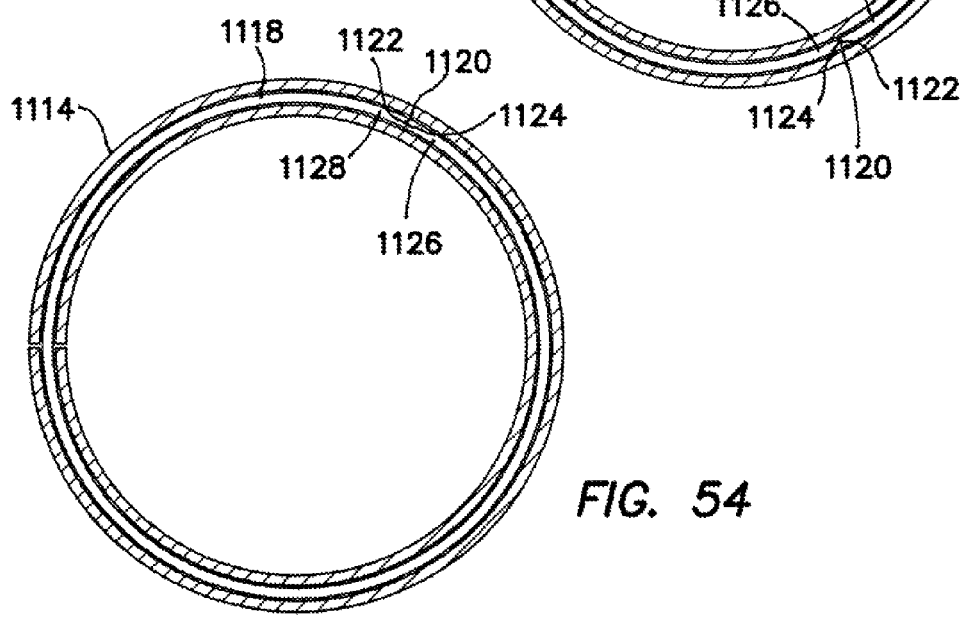
FIG. 54 is a section view taken from line 54-54 in FIG. 52 and showing the split hoop in a circular tube of the outer ring.

Referring to FIGS. 52-54, a wound retractor 1200 may include the double-tube outer ring 1102 having a substantially noncompliant, first split hoop 1118 positioned in the lumen of the first circular tube 1112 and a substantially noncompliant, second split hoop 1118 positioned in the lumen of the second circular tube 1114. As stated above, the substantially noncompliant, split hoop 1118 includes a single split 1120 about its circumference with the split creating a first end 1122 of the split hoop, a second end 1124 of the split hoop, a first end portion 1126 and a second end portion 1128 of the respective split hoop. When the split hoop 1118 is in its neutral position, the first and second ends 1122, 1124 of the respective hoops 1118 substantially abut each other.

With continued reference to FIGS. 52-54, with each of the first and second circular tubes 1112, 1114 including a split hoop 1118, it is not necessary to provide means for the first end portion 1126 and the second end portion 1128 to overlap each other when rolling the sleeve 1106 around the outer ring 1102. Since the split hoop 1118 in the each of the first and second circular tubes 1112, 1114 has substantially abutting first and second ends 1122, 1124 and no means are provided for the first and second end portions 1126, 1128 of the split hoops to overlap each other, each of the split hoops 1118 functions as an axle about which the outer ring 1102 may turn for half a rotation, or 180°. More particularly, the first circular tube 1112 may be rolled outside the second circular tube 1114 with the circumference of the first split hoop 1118 in the first circular tube expanding to clear the second split hoop 1118 in the second circular tube. Then the second circular tube 1114 may be rolled outside the first circular tube 1112 with the circumference of the second split hoop 1118 in the second circular tube expanding to clear the first split hoop 1118 in the first circular tube. These steps may be repeated until the wound 1104 is retracted to the desired degree.

In another embodiment similar to the embodiment depicted in FIGS. 52-54, FIGS. 55-57 depict a wound retractor 1210 having a double-tube outer ring 1102 with a substantially noncompliant, first split hoop 1142 positioned in the lumen of the first circular tube 1112 and a substantially noncompliant, second split hoop 1142 positioned in the lumen of the second circular tube 1114. As stated above, the substantially noncompliant, split hoop 1142 includes a single split about its circumference with the split creating a first end 1146 of the split hoop, a second end 1148 of the split hoop, a first end portion 1150 and a second end portion 1152 of the respective split hoop. When the split hoop 1142 is in its neutral position, there is a space 1144 between the first and second ends 1146, 1148 of the respective split hoop 1142. The spaces 1144 in each of the split hoops 1142 may be sufficient to substantially prevent the first and second ends 1146, 1148 from contacting each other when the split hoops contract while rolling the sleeve 1106 around the outer ring 1102.

Figure 55:
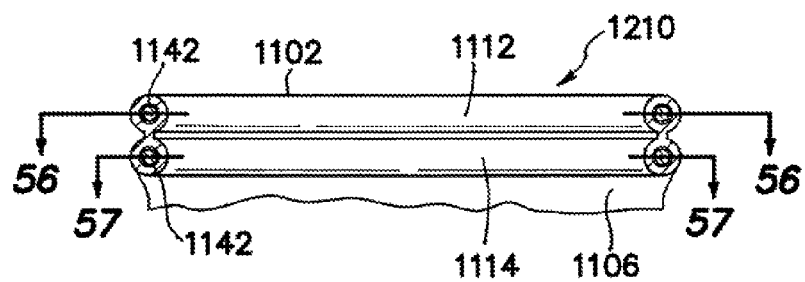
FIG. 55 is a side section view of the double-tube outer ring of the wound retractor having a split hoop in each of the circular tubes of the outer ring with the split hoops each having a single split with a space between the ends of each of the hoops.
Figure 56:
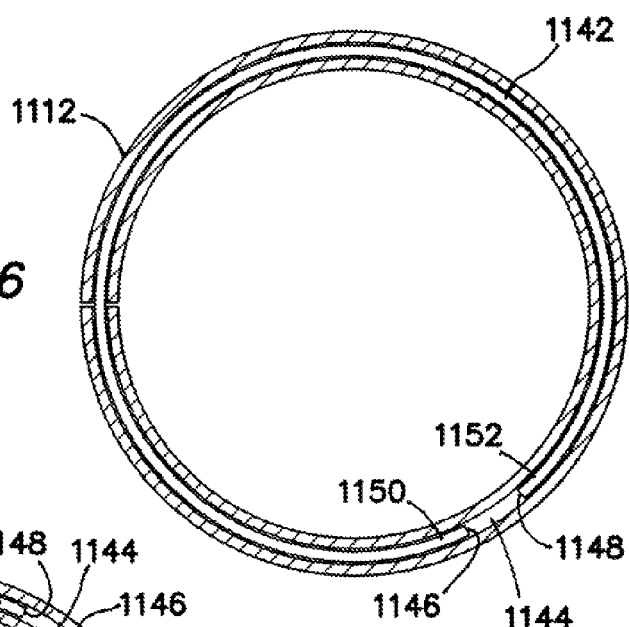
FIG. 56 is a section view taken from line 56-56 in FIG. 55 and showing the split hoop in a circular tube of the outer ring.
Figure 57:
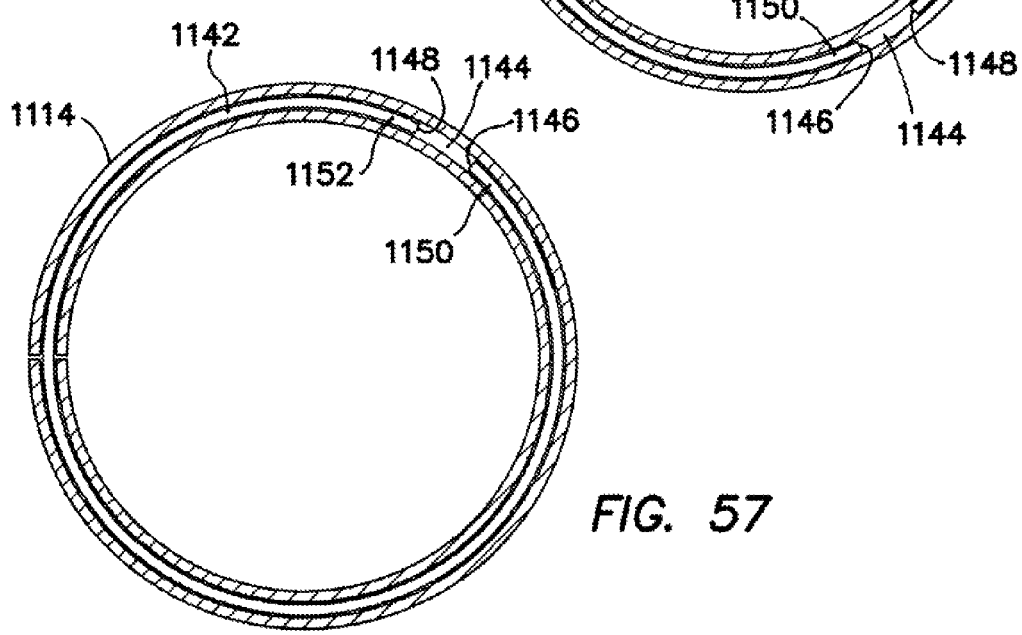
FIG. 57 is a section view taken from line 57-57 in FIG. 55 and showing the split hoop in a circular tube of the outer ring.

With continued reference to FIGS. 55-57, with each of the first and second circular tubes 1112, 1114 including a split hoop 1142, it is not necessary to provide means for the first end portion 1150 and the second end portion 1152 to overlap each other when rolling the sleeve 1106 around the outer ring 1102. Since the split hoop 1142 in the each of the first and second circular tubes 1112, 1114 has a space 1144 between the first and second ends 1146, 1148, the split hoops 1142 may rotate about each other. More particularly, the first circular tube 1112 may be rolled outside the second circular tube 1114 with the circumference of the first split hoop 1142 in the first circular tube expanding and the circumference of the second split hoop 1142 in the second circular tube contracting to clear each other. Then the second circular tube 1114 may be rolled outside the first circular tube 1112 with the circumference of the second split hoop 1142 in the second circular tube expanding and the circumference of the first split hoop 1142 in the first circular tube contracting to clear each other. These steps may be repeated until the wound 1104 is retracted to the desired degree.

In another embodiment similar to the embodiment depicted in FIGS. 52-54, FIGS. 58-60 depict a wound retractor 1220 having a double-tube outer ring 1102 with a substantially noncompliant, first split hoop 1162 having two or more splits 1164 about the circumference of the split hoop positioned in the lumen of the first circular tube 1112 and a substantially noncompliant, second split hoop 1162 having two or more splits 1164 about the circumference of the split hoop positioned in the lumen of the second circular tube 1114. As stated above, the splits 1164 create first ends 1166, second ends 1168, first end portions 1170 and second end portions 1172 of each portion of the respective split hoop 1162. The two or more splits 1164 may be substantially equally spaced about the circumference of the split hoops 1162. When the split hoops 1162 are in their neutral positions, the first and second ends 1166, 1168 of adjacent hoop portions of the respective split hoops 1162 substantially abut each other.

Figure 58:
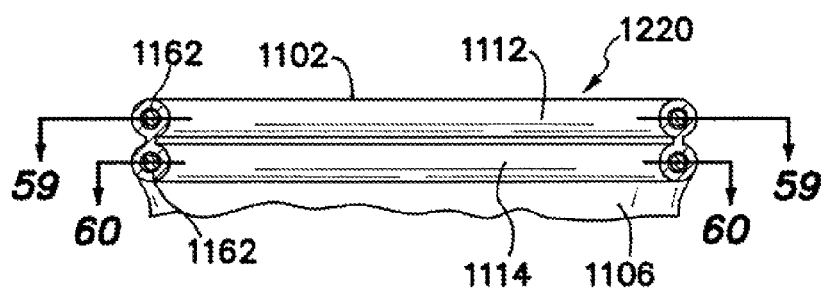
FIG. 58 is a side section view of the double-tube outer ring of the wound retractor having a split hoop in each of the circular tubes of the outer ring with the split hoops each having more than one split with the ends of each of the hoop portions of each respective hoop abutting each other.
Figure 59:
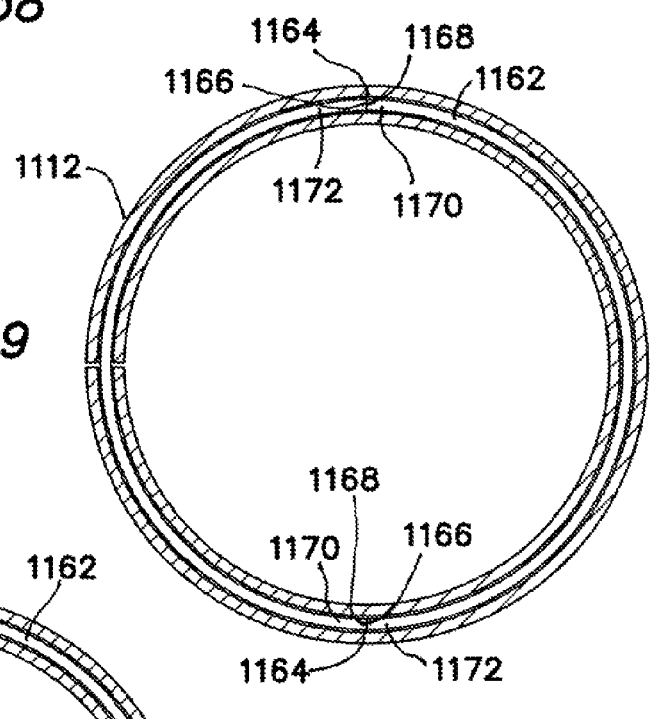
FIG. 59 is a section view taken from line 59-59 in FIG. 58 and showing the split hoop in a circular tube of the outer ring.
Figure 60:
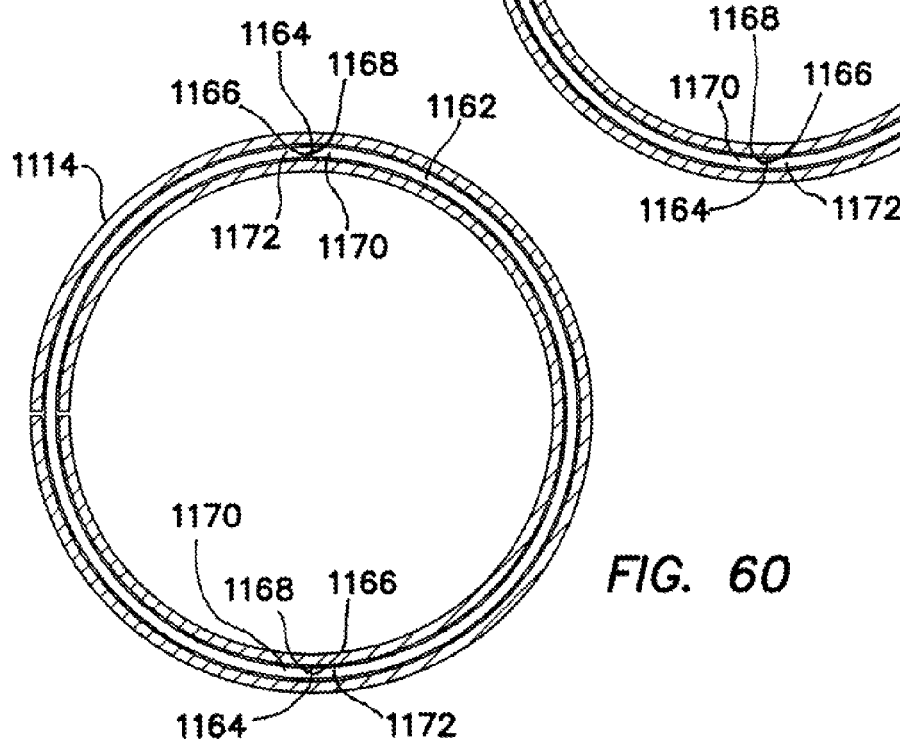
FIG. 60 is a section view taken from line 60-60 in FIG. 58 and showing the split hoop in a circular tube of the outer ring.

With continued reference to FIGS. 58-60, with each of the first and second circular tubes 1112, 1114 including a split hoop 1162, it is not necessary to provide means for the first end portions 1170 and the second end portions 1172 of adjacent portions of the split hoops to overlap each other when rolling the sleeve 1106 around the outer ring 1102. Since the portions of the split hoops 1162 in the each of the first and second circular tubes 1112, 1114 have substantially abutting first and second ends 1166, 1168 and no means are provided for the first and second end portions 1170, 1172 of the split hoops to overlap each other, each of the split hoops 1162 functions as an axle about which the outer ring 1102 may turn for half a rotation. More particularly, the first circular tube 1112 may be rolled outside the second circular tube 1114 with the circumference of the first split hoop 1162 in the first circular tube expanding to clear the second split hoop 1162 in the second circular tube. Then the second circular tube 1114 may be rolled outside the first circular tube 1112 with the circumference of the second split hoop 1162 in the second circular tube expanding to clear the first split hoop 1162 in the first circular tube. These steps may be repeated until the wound 1104 is retracted to the desired degree.

In another embodiment similar to the embodiment depicted in FIGS. 52-54, FIGS. 61-63 depict a wound retractor 1230 having a double-tube outer ring 1102 with a substantially noncompliant, first split hoop 1182 having two or more splits 1184 about the circumference of the split hoop positioned in the lumen of the first circular tube 1112 and a substantially noncompliant, second split hoop 1182 having two or more splits 1184 about the circumference of the split hoop positioned in the lumen of the second circular tube 1114. As stated above, the splits 1184 create first ends 1186, second ends 1188, first end portions 1190 and second end portions 1192 of each portion of the respective split hoop 1182. The two or more splits 1184 may be substantially equally spaced about the circumference of the split hoops 1182. When the split hoops 1182 are in their neutral positions, there is a space 1194 between the first and second ends 1186, 1188 of adjacent portions of the respective split hoops 1182. The spaces 1194 permit the circumferences of the respective split hoops 1182 to expand and contract. The sum of the spaces 1194 of the respective split hoops 1182 may be sufficient to substantially prevent the first and second ends 1186, 1188 of adjacent hoop portions from contacting each other when the respective split hoops 1182 contract while rolling the sleeve 1106 around the outer ring 1102.

Figure 61:
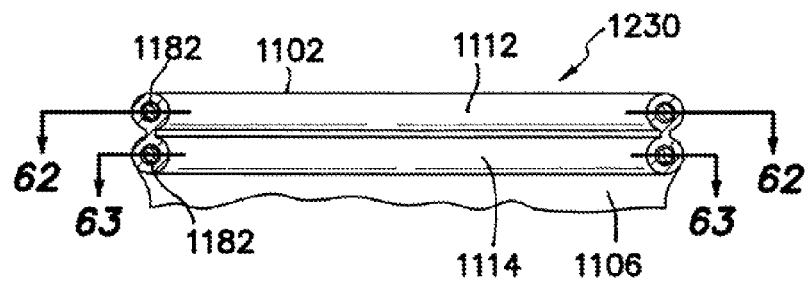
FIG. 61 is a side section view of the double-tube outer ring of the wound retractor having a split hoop in each of the circular tubes of the outer ring with the split hoops each having more than one split with a space between the ends of each of the hoop portions of each respective hoop.
Figure 62:
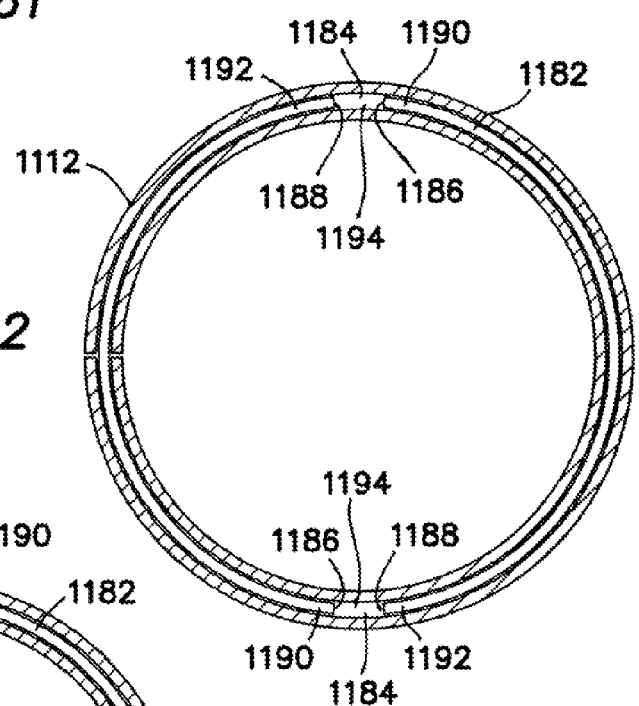
FIG. 62 is a section view taken from line 62-62 in FIG. 61 and showing the split hoop in a circular tube of the outer ring.
Figure 63:
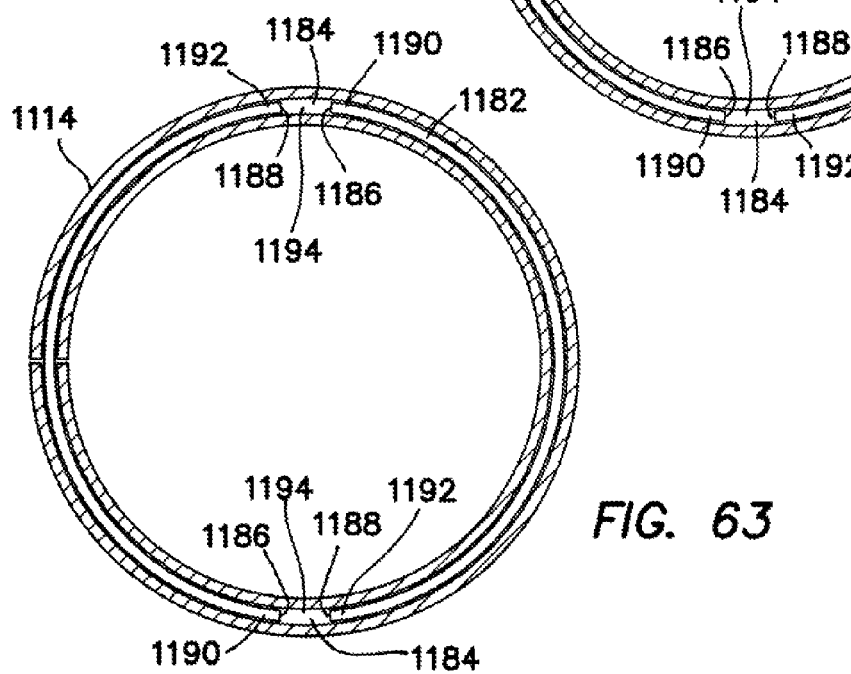
FIG. 63 is a section view taken from line 63-63 in FIG. 61 and showing the split hoop in a circular tube of the outer ring.

With continued reference to FIGS. 61-63, with each of the first and second circular tubes 1112, 1114 including a split hoop 1182, it is not necessary to provide means for the first end portions 1190 and the second end portions 1192 to overlap each other when rolling the sleeve 1106 around the outer ring 1102. Since the split hoop 1182 in the each of the first and second circular tubes 1112, 1114 has a space 1194 between the first and second ends 1186, 1188 of adjacent portions of the respective split hoops 1182, the split hoops may rotate about each other. More particularly, the first circular tube 1112 may be rolled outside the second circular tube 1114 with the circumference of the first split hoop 1182 in the first circular tube expanding and the circumference of the second split hoop 1182 in the second circular tube contracting to clear each other. Then the second circular tube 1114 may be rolled outside the first circular tube 1112 with the circumference of the second split hoop 1182 in the second circular tube expanding and the circumference of the first split hoop 1182 in the first circular tube contracting to clear each other. These steps may be repeated until the wound 1104 is retracted to the desired degree.

In other embodiments that incorporate the low-durometer, double-tube outer ring 1102, combinations of the various split hoops 1118, 1142, 1162, 1182 may be positioned within the first and second circular tubes 1112, 1114 of the outer ring 1102. For example, one of the first and second circular tubes 1112, 1114 may include a split hoop 1118 having a single split 1120 with the first and second ends 1122, 1124 of the split hoop substantially abutting each other. The other one of the first and second circular tubes 1112, 1114 may include either: a split hoop 1142 having a single split with a space 1144 between the first and second ends 1146, 1148 of the split hoop 1142; a split hoop 1162 having two or more splits 1164 with adjacent first and second ends 1166, 1168 of adjacent hoop portions substantially abutting each other; or a split hoop 1182 having two or more splits 1188 with a space 1194 between the first and second ends 1186, 1188 of adjacent hoop portions. In another example, one of the first and second circular tubes 1112, 1114 may include a split hoop 1142 having a single split with a space 1144 between the first and second ends 1146, 1148 of the split hoop 1142. The other one of the first and second circular tubes 1112, 1114 may include either: a split hoop 1162 having two or more splits 1164 with adjacent first and second ends 1166, 1168 of adjacent hoop portions substantially abutting each other; or a split hoop 1182 having two or more splits 1188 with a space 1194 between the first and second ends 1186, 1188 of adjacent hoop portions. In another example, one of the first and second circular tubes 1112, 1114 may include a split hoop 1162 having two or more splits 1164 with adjacent first and second ends 1166, 1168 of adjacent hoop portions substantially abutting each other. The other one of the first and second circular tubes 1112, 1114 may include a split hoop 1182 having two or more splits 1188 with a space 1194 between the first and second ends 1186, 1188 of adjacent hoop portions.

Figure 64:
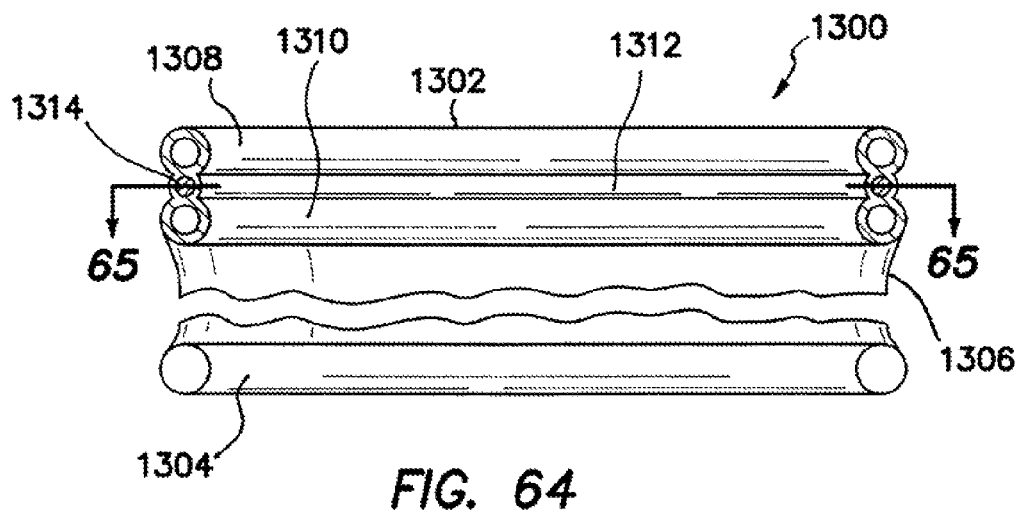
FIG. 64 is a side section view of a wound retractor having a triple-tube outer ring with a continuous hoop positioned in the center circular tube of the outer ring.
Figure 65:
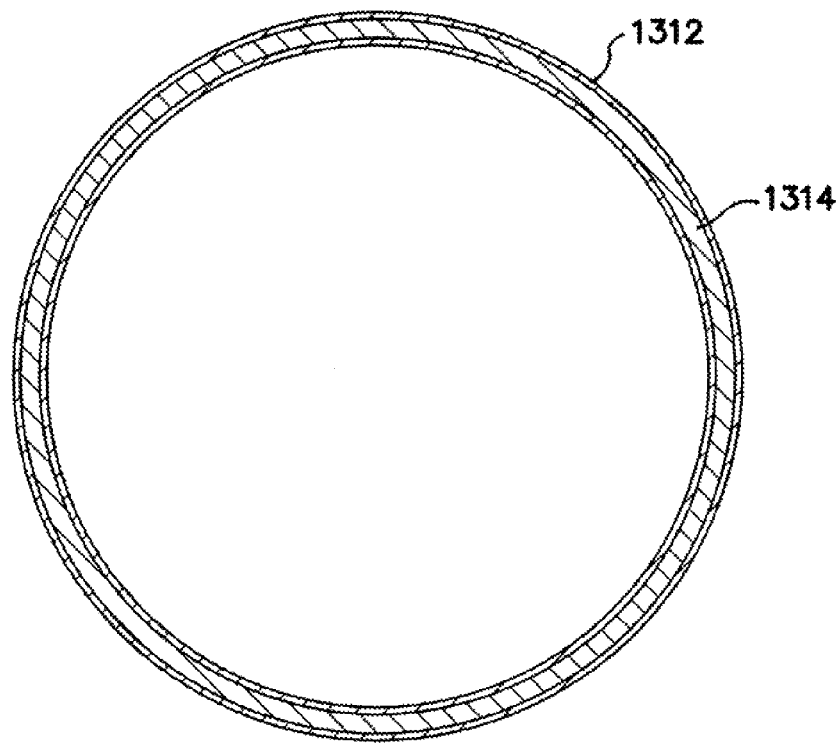
FIG. 65 is a section view taken from line 65-65 in FIG. 64 and showing the continuous hoop in the lumen of the center circular tube of the outer ring.

Referring to FIGS. 64 and 65, other embodiments of a wound retractor 1300 include a triple-tube outer ring 1302, an inner ring 1304, and a distensible sleeve 1306 coupling the outer ring 1302 and the inner ring 1304. The triple-tube outer ring 1302 includes a first circular tube 1308, a second circular tube 1310 and a third circular tube 1312 positioned between, and coupled to, the first and second circular tubes. The third circular tube 1312 includes a lumen. The first and second circular tubes 1308, 1310 may each include a lumen also. The cross-sectional diameters of the first and second circular tubes 1308, 1310 are substantially equal. The cross-sectional diameter of the third circular tube 1312 may be smaller than the cross-sectional diameters of the first and second circular tubes 1308, 1310 or may be substantially equal to the cross-sectional diameters of the first and second circular tubes. The lumen of the third circular tube 1312 includes a substantially rigid, noncompliant, continuous hoop 1314. The lumens of the first and second circular tubes 1308, 1310 may be hollow. In this manner, the cross-section of the outer ring 1302 is substantially symmetrical.

Similar to the depiction in FIGS. 25c through 25e, the outer ring 1302 may be formed by transforming an extruded elastomeric tube into a circular ring. To place the continuous hoop 1314 into the third circular tube 1312, the hoop may include a split that produces at least a first and second end. One of the first and second ends of the hoop 1314 may be fed into the lumen of the third circular tube 1312 and continually fed until substantially the entire hoop 1314 is within the lumen of the third circular tube. The at least first and second ends of the hoop 1314 may then be joined together to form the continuous hoop 1314. The at least first and second ends of the hoop 1314 may be joined by welding, brazing, mechanical means, or any other means that is well known in the art.

With the third circular tube 1312 including the substantially rigid, noncompliant, continuous hoop 1314 within its lumen, rolling the sleeve 1306 around the outer ring 1302 includes turning the first and second circular tubes 1308, 1310 about the third circular tube 1312. The continuous hoop 1314 functions as an axle about which the outer ring 1302 is turned. Positioning the continuous hoop 1314 substantially symmetrically between the first and second circular tubes 1308, 1310 provides even motion when turning the first and second circular tubes about the continuous hoop 1314 to roll the sleeve 1306 around the outer ring 1302.

Figure 66A:
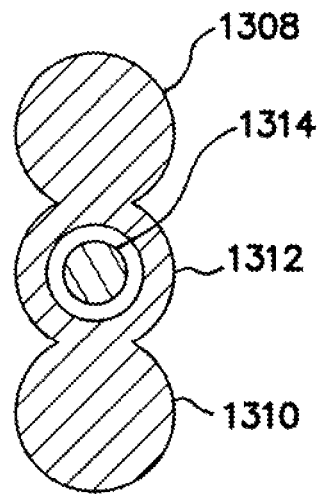
FIGS. 66a through 66h are section views of various embodiments of triple-tube outer rings for the wound retractor.
Figure 66B:
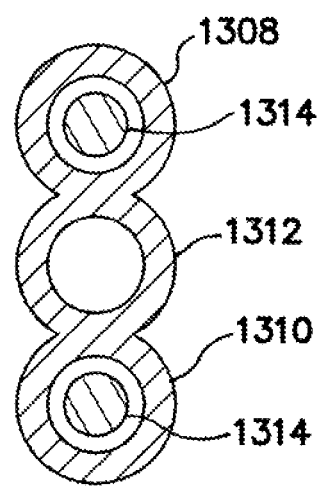
Figure 66C:
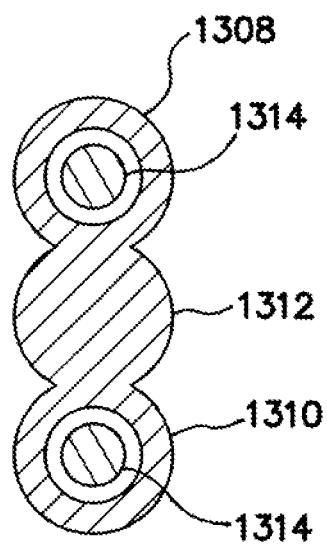
Figure 66D:
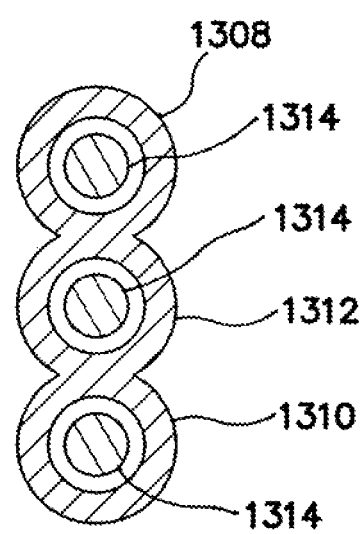
Figure 66E:
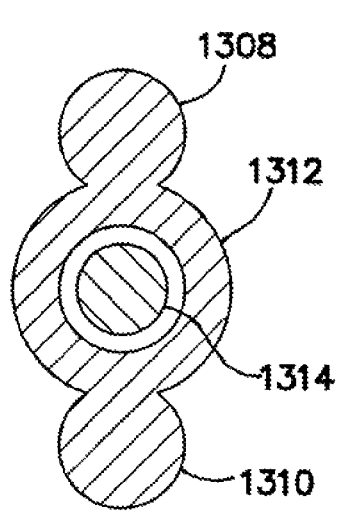
Figure 66F:
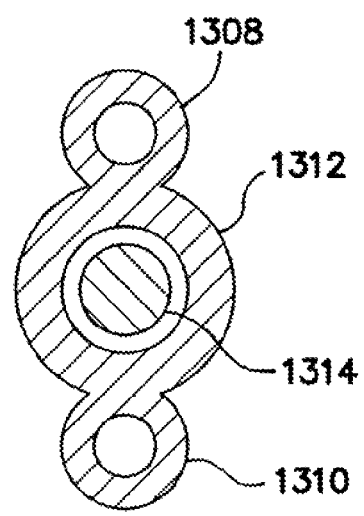
Figure 66G:
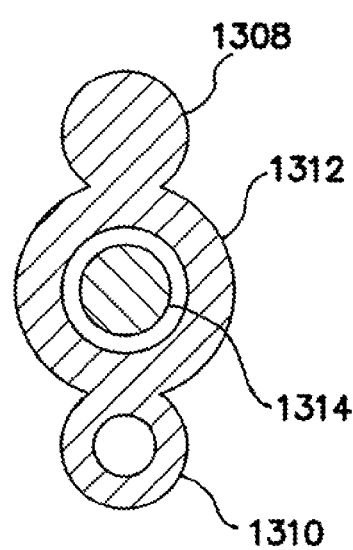
Figure 66H:
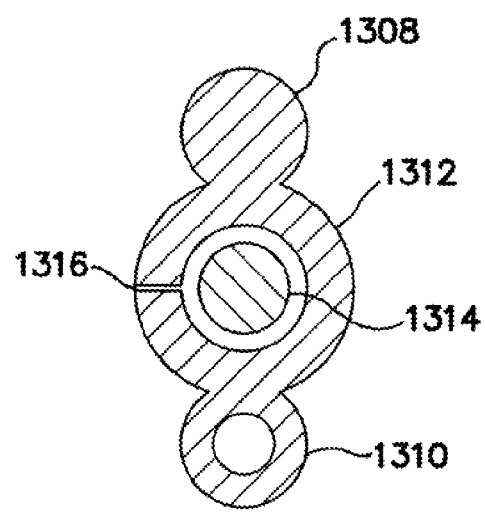

In another aspect, depicted in FIGS. 66a-66d, the cross-sectional diameters of the first, second and third circular tubes 1308, 1310 and 1312 may be substantially equal, or the cross-sectional diameter of the third circular tube 1312 may be larger than the cross-sectional diameters of the first and second circular tubes 1308, 1310, as depicted in FIGS. 66e-66h. Also, the first and second circular tubes 1308, 1310 may be solid, as depicted in FIGS. 66a and 66e. Alternatively, all three circular tubes 1308, 1310, 1312 may include a lumen as depicted in FIGS. 66b, 66d and 66f. With lumens in each of the three circular tubes 1308, 1310, 1312, the hoop 1314 may be included in only the third circular tube 1312 (FIG. 66f), in only the first and second circular tubes 1308 (FIG. 66b), or in all three circular tubes 1308, 1310, 1312 (FIG. 66d). In another aspect, the third circular tube 1312 may be solid while the first and second circular tubes 1308, 1310 have lumens with a hoop 1314 positioned in each of the lumens (FIG. 66c). In a further aspect, one of the first and second circular tubes 1308, 1310 may be solid while the third circular tube 1312 and the other of the first and second circular tubes includes a lumen (FIGS. 66g, 66h) with the hoop 1314 positioned in the lumen of the third circular tube. In an additional aspect, the hoop 1314 may be inserted into the lumen of a circular tube 1308, 1310, 1312 via a slit 1316 in the wall of the circular tube (FIG. 66h).

Figure 67:
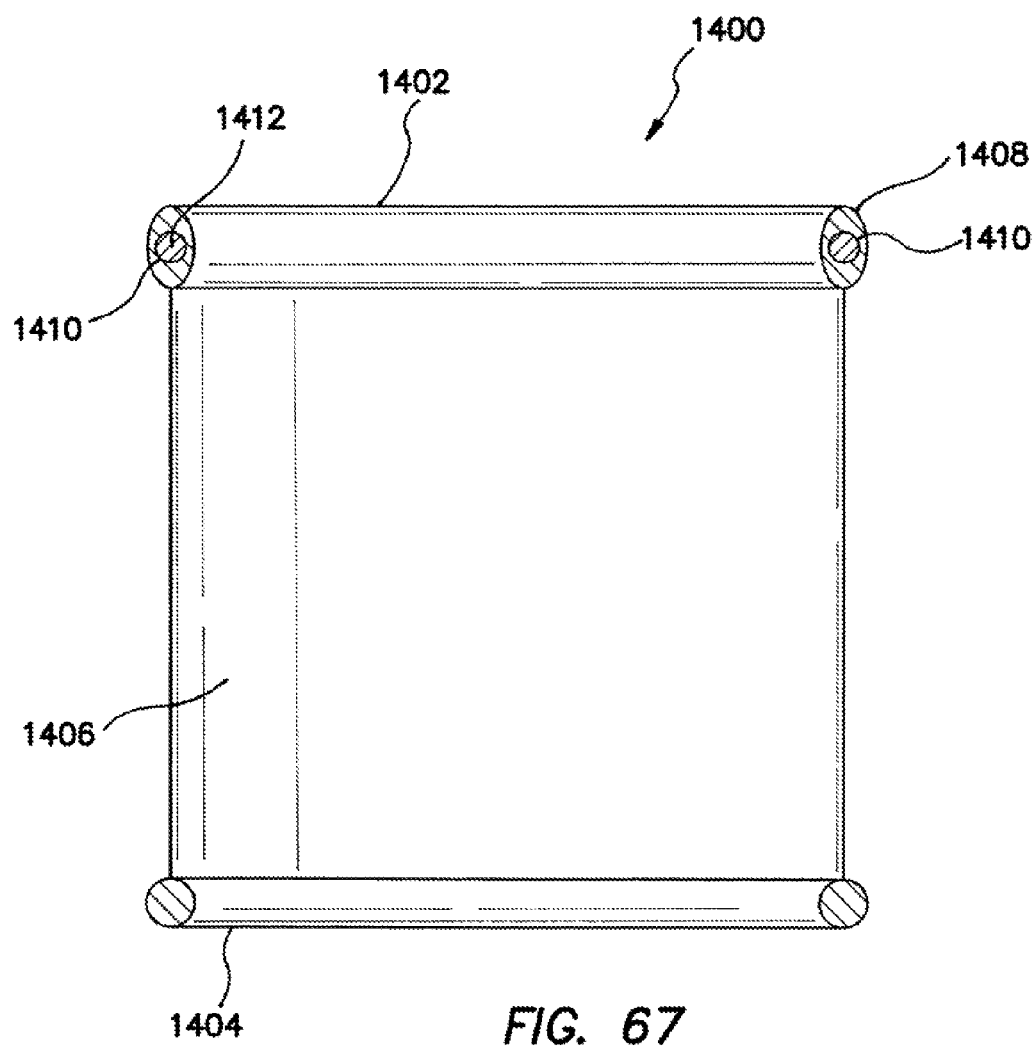
FIG. 67 is a section view of a wound retractor having an oval-shaped outer ring with a continuous hoop positioned within a lumen of the outer ring.

Referring to FIG. 67, other embodiments of a wound retractor 1400 include a single-tube outer ring 1402, an inner ring 1404, and a distensible sleeve 1406 coupling the outer ring 1402 and the inner ring 1404. The single-tube outer ring 1402 includes a tube 1408 having a substantially oval cross-section and a lumen 1410 positioned substantially in the center of the oval cross-section. A substantially rigid, non-compliant, continuous hoop 1412 is positioned within the lumen 1410 of the tube 1408. In this manner, the cross-section of the outer ring 1402 is substantially symmetrical.

Similar to the depiction in FIGS. 25c through 25e, the outer ring 1402 may be formed by transforming an extruded elastomeric tube into a circular ring. To place the continuous hoop 1412 into the lumen 1410 of the tube 1408, the hoop may include a split that produces at least a first and second end. One of the first and second ends of the hoop 1412 may be fed into the lumen 1410 of the tube 1408 and continually fed until substantially the entire hoop 1412 is within the lumen of the tube. The at least first and second ends of the hoop 1412 may then be joined together to form the continuous hoop 1412. The at least first and second ends of the hoop 1412 may be joined by welding, brazing, mechanical means, or any other means that is well known in the art.

With the tube 1408 having the substantially rigid, noncompliant, continuous hoop 1412 within its lumen 1410, rolling the sleeve 1406 around the outer ring 1402 includes turning the tube 1408 about the hoop 1412. The continuous hoop 1412 functions as an axle about which the tube 1408 is turned. Positioning the continuous hoop 1412 substantially in the center of the tube 1408 provides even motion when turning the tube 1408 about the continuous hoop 1412 to roll the sleeve 1406 around the outer ring 1402.

Figure 68:
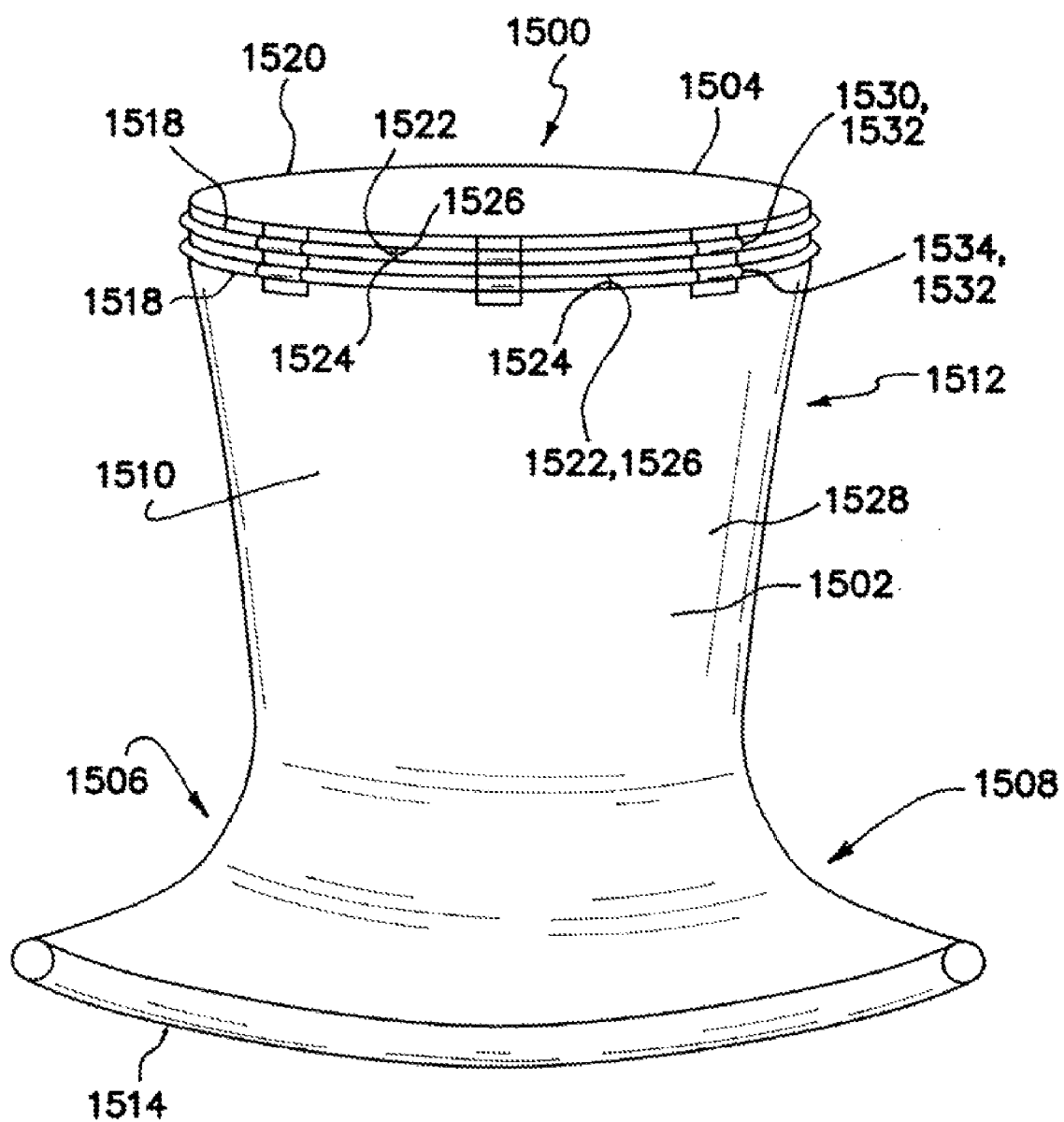
FIG. 68 is a perspective view of a wound retractor having an inner ring at a distal end of the wound retractor and a pair of rigid, noncompliant split hoops toward the proximal end of the wound retractor.

Referring to FIG. 68, other embodiments of a wound retractor 1500 include a retraction sheath 1502 having a tubular wall 1504. The tubular wall 1504 has a configuration of the frustum of a cone 1506 at a distal portion 1508 of the sheath 1502 and a configuration of a cylinder 1510 at a proximal portion 1512 of the sheath 1502. The distal end of the retraction sheath 1502 includes an inner ring 1514. The inner ring 1514 may be flexible to facilitate insertion into a wound in a body wall of a patient. The retraction sheath 1502 may be made of an elastomeric material, such as a low durometer polymeric material. The elastomeric material for forming the retraction sheath 1502 may include neoprene. The low durometer material of the retraction sheath 1502 does not have sufficient strength to adequately retract a wound 1516 (FIG. 69) without the inclusion of strengthening means, such as a hoop, placed within the proximal portion 1512 of the retraction sheath.

Figure 69:
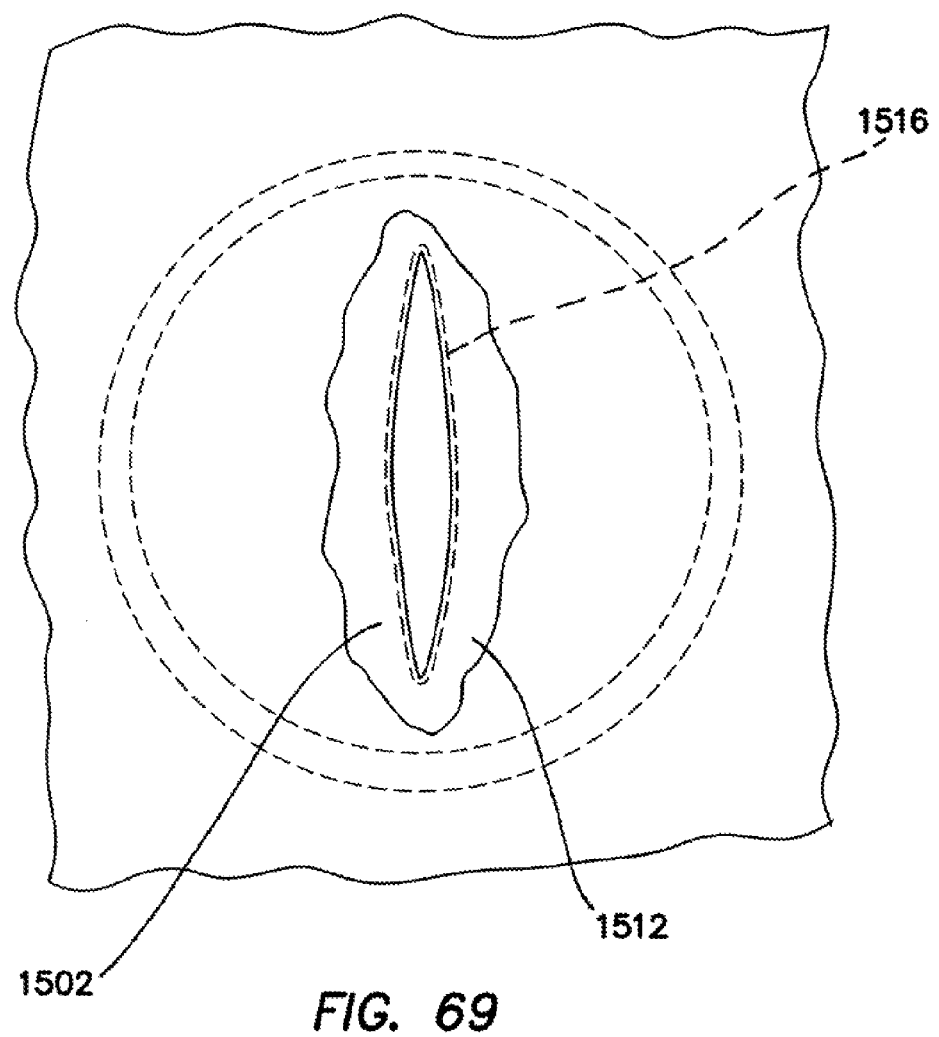
FIG. 69 is a plan view of the wound retractor of FIG. 68 disposed in a wound in a biological body wall with the wound retractor not having the rigid, noncompliant hoops positioned toward the proximal end of the wound retractor.

As depicted in FIG. 69, without strengthening means within the proximal portion 1512 of the retraction sheath 1502, the retraction sheath remains substantially closed even when deployed through the wound 1516. The proximal portion 1512 of the wound retractor 1500 may include a pair of substantially noncompliant, split hoops 1518 (FIG. 68) toward the proximal end 1520 of the retraction sheath 1502. The split hoops 1518 each include a hoop having a single split 1522 about its circumference with the split creating a first end 1524 and a second end 1526 of the split hoop. In their neutral positions, the first and second ends 1524, 1526 of the respective split hoops 1518 may substantially abut each other.

Referring again to FIG. 68, one of the surfaces, such as the outer surface 1528, of the retraction sheath 1502 includes a first row 1530 of a plurality of loops 1532 positioned about a circumference of the retraction sheath toward the proximal end 1520 of the retraction sheath and a second row 1534 of a plurality of loops 1532 positioned about a circumference of the retraction sheath toward the proximal end of the retraction sheath and distal to the first row 1530 of the plurality of loops. The loops 1532 of each of the first and second rows 1530, 1534 are sized and arranged to receive one of the split hoops 1518. A first split hoop 1518 is fed through the loops 1532 in the first row 1530 of loops and a second split hoop 1518 is fed through the loops 1532 in the second row 1534 of loops.

With continued reference to FIG. 68, with the first split hoop 1518 positioned in the first row 1530 of loops 1532 and the second split hoop 1518 positioned in the second row 1534 of loops 1532, the retraction sheath 1502 is retracted by rolling the split hoops 1518 outside of each other with each of the split hoops 1518 performing as an axle about which the other split hoop is rolled outside of. More particularly, the first split hoop 1518 that is positioned in the first row 1530 of loops 1532 may be rolled outside the second split hoop 1518 that is positioned in the second row 1534 of loops 1532 with the circumference of the first split hoop 1518 that is positioned in the first row 1530 of loops 1532 expanding to clear the second split hoop 1518 that is positioned in the second row 1534 of loops 1532. Then, the second split hoop 1518 that is positioned in the second row 1534 of loops 1532 may be rolled outside the first split hoop 1518 that is positioned in the first row 1530 of loops 1532 with the circumference of the second split hoop 1518 that is positioned in the second row 1534 of loops 1532 expanding to clear the first split hoop 1518 that is positioned in the first row 1530 of loops 1532. These steps may be repeated until the wound 1516 is retracted to the desired degree.

Figure 70:
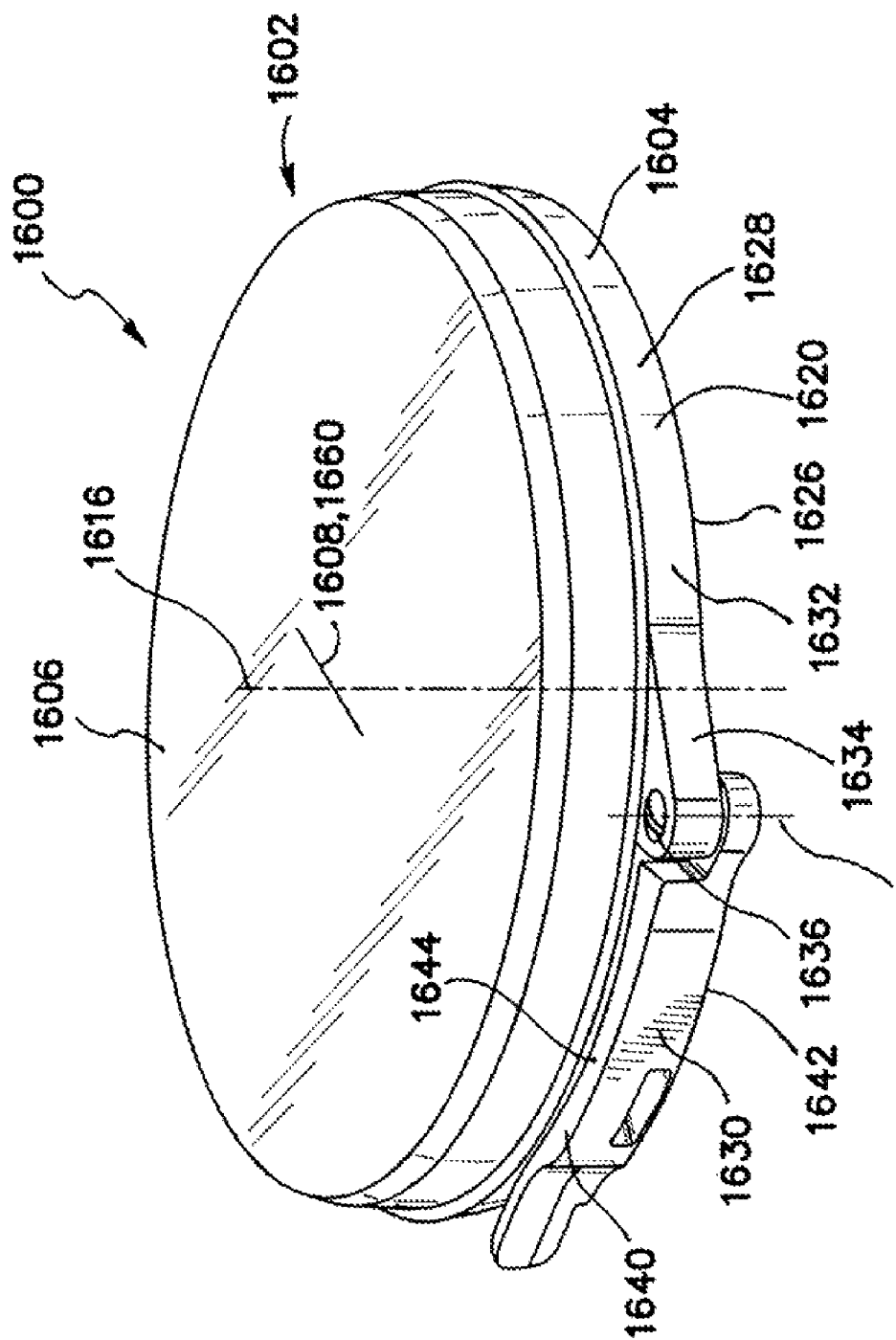
FIG. 70 is a top perspective view of a gel cap having a lever for coupling the gel cap to the outer ring of a wound retractor.

Referring to FIG. 70, the surgical access device 1600, such as a gel cap 1602, is used to seal the opening between the body cavity 404 (see FIG. 4) and the area outside the body cavity while providing access into the body cavity from outside the body cavity. The gel cap 1602 includes a cap ring 1604 that couples to the outer ring 102 of the wound retractor 100 and a gel pad 1606 coupled to the cap ring. The gel pad 1606 is made of a gel material and includes an access portion 1608 or passage through the gel for providing passage from external the body to the body cavity 404. In one aspect, the access portion 1608 may include a plurality of intersecting dead-end slits 1660, 1662. The access portion 1608 forms an instrument seal in the presence of an instrument, such as the arm of a surgeon, inserted therethrough and a zero seal in the absence of an instrument inserted therethrough. Unlike foam rubber or other similar types of elastic materials, the gel provides a gas tight seal around a variety of shapes and sizes of hands or instruments inserted therethrough.

In one aspect, the gel material from which the gel pad 1606 is made is an elastomeric gel. Some such gels have been described in U.S. patent application Ser. No. 10/381,220, filed Mar. 20, 2003, the disclosure of which is hereby incorporated by reference as if set forth in full herein. The gel can be prepared by mixing a triblock copolymer with a solvent for the midblocks. The endblocks are typically thermoplastic materials, such as styrene, and the midblocks are thermoset elastomers, such as isoprene or butadiene, e.g., Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and by the nature of the endblocks is processable as thermoplastic elastomers henceforward. The mixture or slurry has a minimum temperature at which it becomes a gel, i.e., the minimum gelling temperature (MGT). This temperature in one aspect corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing a means for visually confirming when the transformation of the slurry to the gel state is substantially complete and that the gel may be cooled. In addition to triblocks there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a seventy percent (70%) SEB thirty percent (30%) SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include polyvinyl chloride (PVC), isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing boding sites or a surface charge. Additionally, oil based colorants may be added to the slurry to create gels of different colors.

In one aspect, the mixture/slurry used with the various embodiments of the caps that are described herein are composed of ninety percent (90%) by weight of mineral oil and ten percent (10%) by weight of KRATON G1651. From a thermodynamic standpoint, this mixture behaves similar to mineral oil. Mineral oil has a considerable heat capacity and therefore at about 130° C. it can take three (3) or four (4) hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect the gel may be air-cooled. Those familiar with the art will recognize that other cooling techniques that are well know in the art may be employed and are contemplated as within the scope of the present invention.

Many of the properties of the KRATON/oil mixture will vary with adjustments in the weight ratio of the components. In general, the greater the percentage of mineral oil, the less firm the mixture; the greater the percentage of KRATON, the more firm the mixture. If the resultant gel is too soft it can lead to excessive tenting or doming of the cap during surgery when a patient's abdominal cavity is insufflated. Excessive tenting or doming may cause the slits to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about one (1.0) atmosphere. The slurry may be stirred while under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about ten percent (10%). Degassing the slurry helps reduce the potential of the finished gel to oxidize.

Degassing the slurry tends to make the resultant gel firmer. A degassed slurry composed of about 91.6% by weight of mineral oil and 8.4% by weight of KRATON G1651, an eleven-to-one ratio, results in a gel having about the same firmness as a gel made from a slurry that is not degassed composed of ninety percent (90%) by weight of mineral oil and ten percent (10%) by weight of KRATON G1651, a nine-to-one ratio.

Mineral oil is of a lighter density than KRATON and the two components will separate after mixing, with the lighter mineral oil rising to the top of the container. This separation may occur when attempting to form a static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

Figure 71:
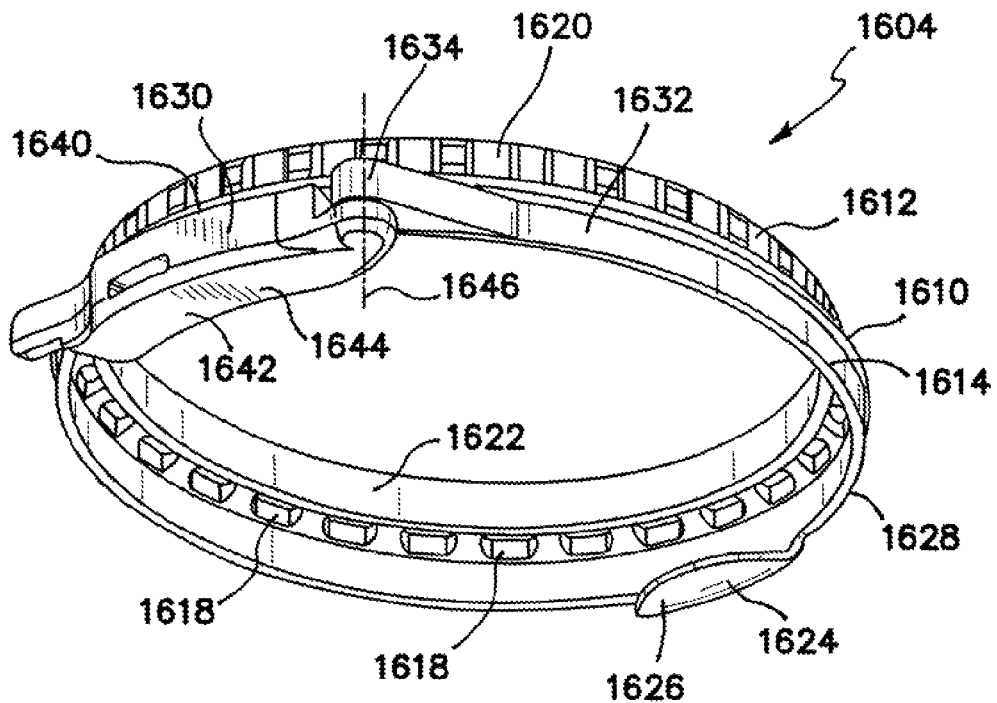
FIG. 71 is a bottom perspective view of a cap ring of the gel cap of FIG. 70.
Figure 72:
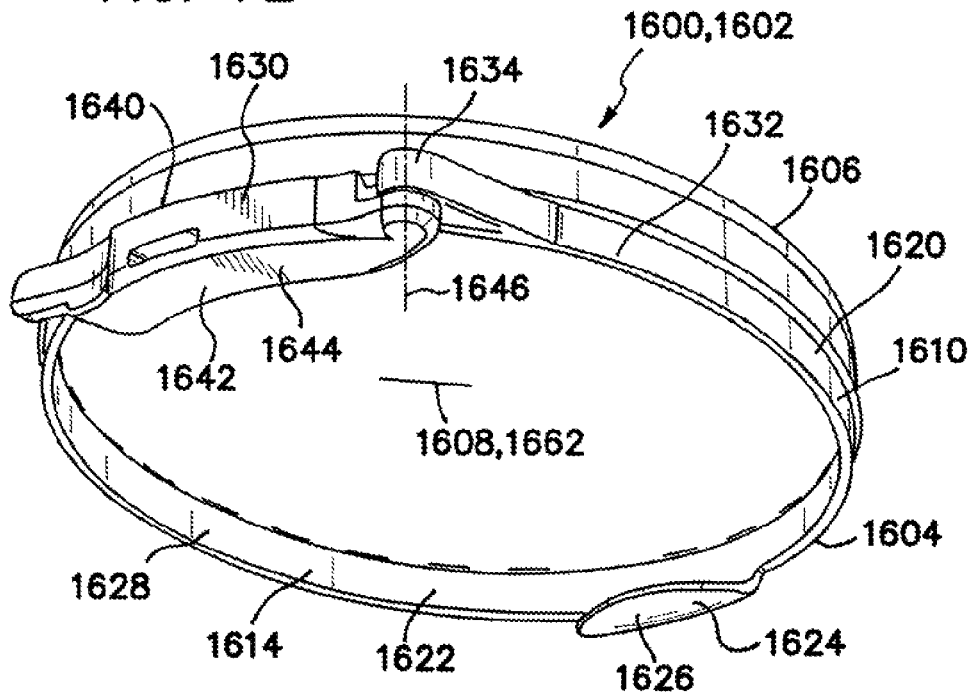
FIG. 72 is a bottom perspective view of the gel cap of FIG. 70

To combine the gel pad 1606 with the cap ring 1604, the cap ring may be placed into a mold that includes the shape of the desired gel pad and the uncured gel is added to the mold. Referring to FIG. 71, in one aspect, the cap ring 1604 includes a substantially cylindrical ring 1610 having a first, proximal portion 1612, a second, distal portion 1614 and a longitudinal axis 1616 (FIG. 70) extending through the proximal and distal portions. The gel pad 1606 is positioned at the proximal portion 1612 of the cap ring 1604. The proximal portion 1612 of the cap ring 1604 may include a plurality of apertures 1618 distributed about the circumference of the cap ring. The apertures 1618 may extend through the wall of the proximal portion 1612 of the cap ring 1604. Sufficient gel may be added to the mold to cover and fill the apertures 1618 (see FIG. 72). When adding uncured gel into the mold, the gel flows through the apertures 1618 and remains in the apertures. Also, for reasons that will be described below, sufficient gel may be added to the mold to extend into the distal portion 1614 of the cap ring 1604. When the gel pad 1606 is cured, the gel in the apertures 1618 connects the gel at the outer portion 1620 of the cap ring 1604 to the gel at the inner portion 1622 of the cap ring, thus forming a mechanical lock between the gel and the cap ring. As will be described in more detail below, other means may be used to couple the gel pad 1606 to the cap ring 1604.

Figure 73:
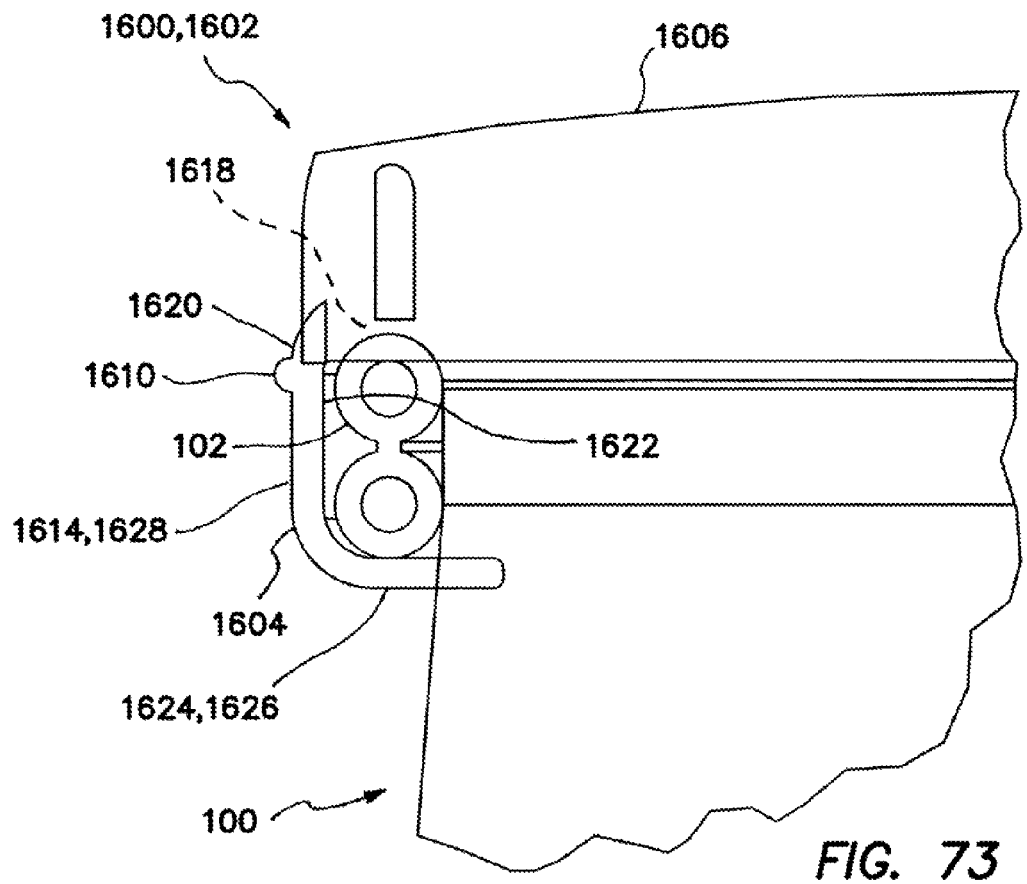
FIG. 73 is a partial section view of the gel cap of FIG. 70 coupled to the outer ring of the wound retractor.

The distal portion 1614 of the cap ring 1604 is substantially cylindrical and is configured to receive the outer ring 102 of the wound retractor 100. In one aspect, the distal portion 1614 of the cap ring 1604 includes a lip 1624 at the distal end 1626 thereof (see FIG. 71). The lip 1624 curves radially inwardly from the wall 1628 of the distal portion 1614 of the cap ring 1604 and extends around a portion of the circumference of the cap ring. In one aspect, the lip 1624 extends around about 30° of the circumference of the cap ring 1604; however, the lip may extend longer or shorter distances around the circumference of the cap ring. The lip 1624 is configured to receive the distal-most circular tube 108, 110 of the outer ring 102 such that the outer ring is positioned between the lip 1624 and the gel pad 1606 (see FIG. 73). More particularly, when the outer ring 102 of the wound retractor 100 is received by the distal portion 1614 of the cap ring 1604, the outer ring of the wound retractor embeds into the gel pad 1606 at the distal portion of the cap ring and displaces the gel, thereby forming a seal between the gel pad and the outer ring and sleeve 106 of the wound retractor. This places the gel pad 1606 in juxtaposition with the incision 400.

In one aspect, the distal portion 1614 of the cap ring 1604 also includes a swinging lever 1630 (FIG. 70) that swings on a plane that is substantially perpendicular to the axis 1616 of the cap ring. In one aspect, the lever 1630 is positioned substantially opposite the lip 1624 on the distal portion 1614 of the cap ring 1604. The outer surface 1632 of the cap ring 1604 may include a lug 1634 to which the lever 1630 is coupled. In one aspect, the lug 1634 includes an aperture 1636 extending substantially parallel to the longitudinal axis 1616 of the cap ring 1604 and is adapted to receive a hinge pin 1638 portion of the lever 1630. However, those familiar with the art will recognize that the hinge pin may be positioned on the lug and the aperture may be positioned in the lever. Also, other means that are well known in the art may be used to hinge the lever to the cap ring. When coupled to the cap ring 1604, the lever 1630 includes a proximal end 1640 and a distal end 1642. The lever 1630 includes a first, distal substantially flat lip 1644 positioned at the distal end 1642 of the lever and lying in a plane that is positioned substantially perpendicular to an axis 1646 of the pin 1638 on the lever. It should be noted that the axis 1646 of the pin on the lever 1630 is substantially parallel to the longitudinal axis 1616 of the cap ring 1604. The lever 1630 may also include a second, proximal substantially flat lip 1648 positioned at the proximal end 1640 of the lever and also lying in a plane that is substantially perpendicular to the axis 1646 of the pin 1638 on the lever such that the proximal lip of the lever is substantially parallel to the distal lip 1644 of the lever. Both of the distal and proximal lips 1644, 1648 of the lever 1630 extend from the same side of the lever.

Figure 75:
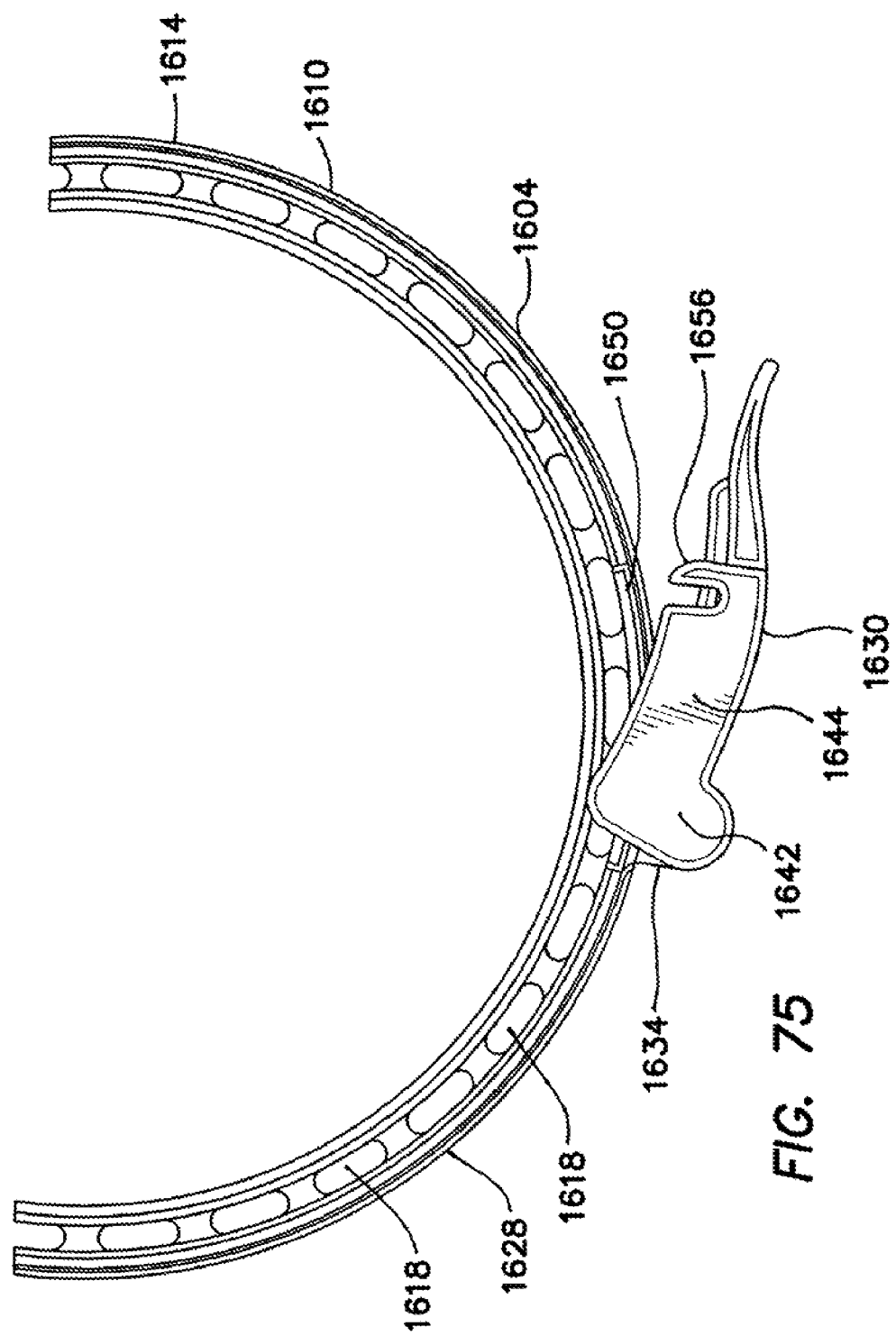
FIG. 75 is a partial bottom view of the cap ring of FIG. 70 with the lever in a first, open state.
Figure 76:
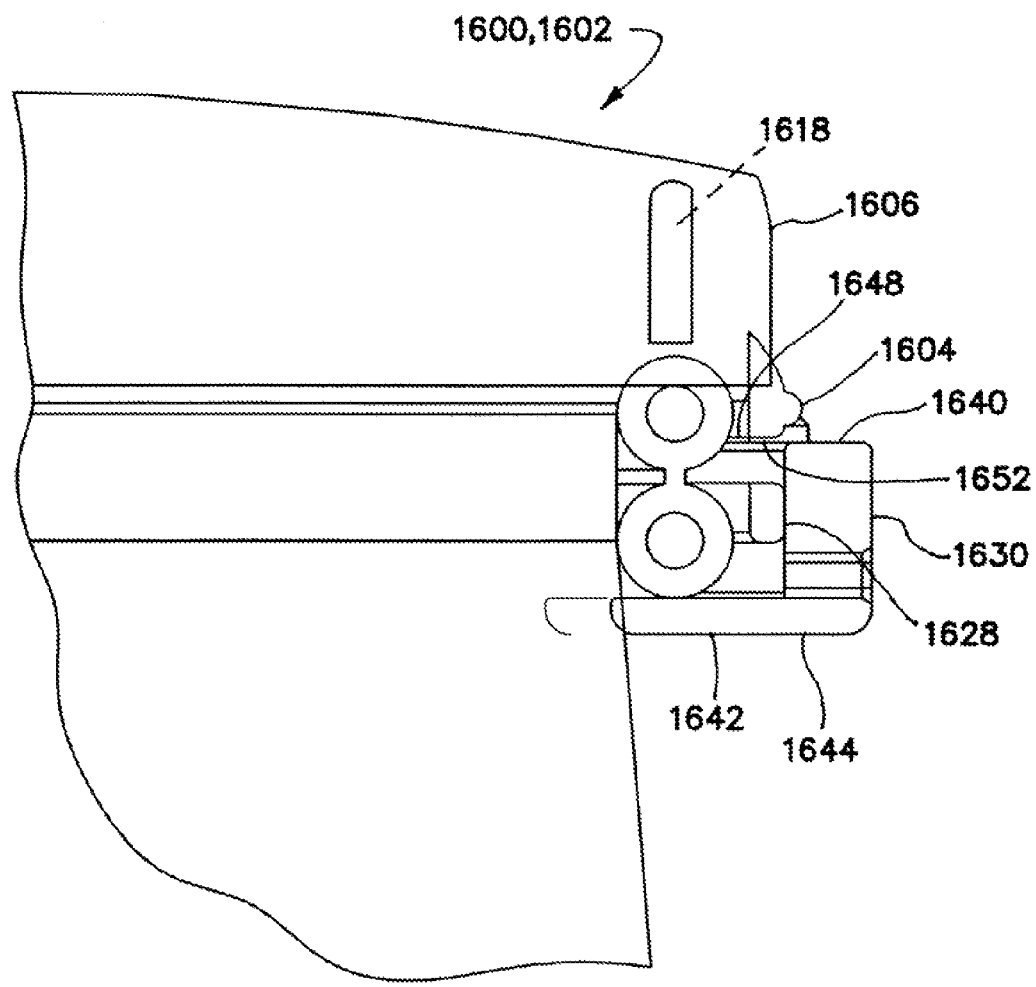
FIG. 76 is a partial section view of the gel cap of FIG. 70 coupled to the outer ring of the wound retractor with the lever in a second, closed state.

In a first, open state (FIG. 75), the lever 1630 is swung outwardly, away from the body of the cap ring 1604 to provide clearance for inserting the outer ring 102 of the wound retractor 100 into the gel cap. In a second, closed state (FIG. 76), the lever 1630 is swung toward the cap ring 1604 such that the distal and proximal lips 1644, 1648 of the lever protrude radially inwardly from the body of the lever and radially inwardly through the wall 1628 of the cap ring. In one aspect, the wall 1628 of the distal portion 1614 of the cap ring 1604 includes an aperture 1650 or groove for receiving the distal lip 1644 of the lever 1630. Similarly, the wall 1628 of the distal portion 1614 of the cap ring 1604 also includes a second aperture 1652, such as a slot, for receiving and supporting the proximal lip 1648 of the lever 1630. In one aspect, the distal lip 1644 on the lever 1630 extends around about 60° of the circumference of the cap ring and the proximal lip 1648 on the lever extends around about 45° of the circumference of the cap ring; however, the distal and proximal lips may extend longer or shorter distances around the circumference of the cap ring.

Figure 77:
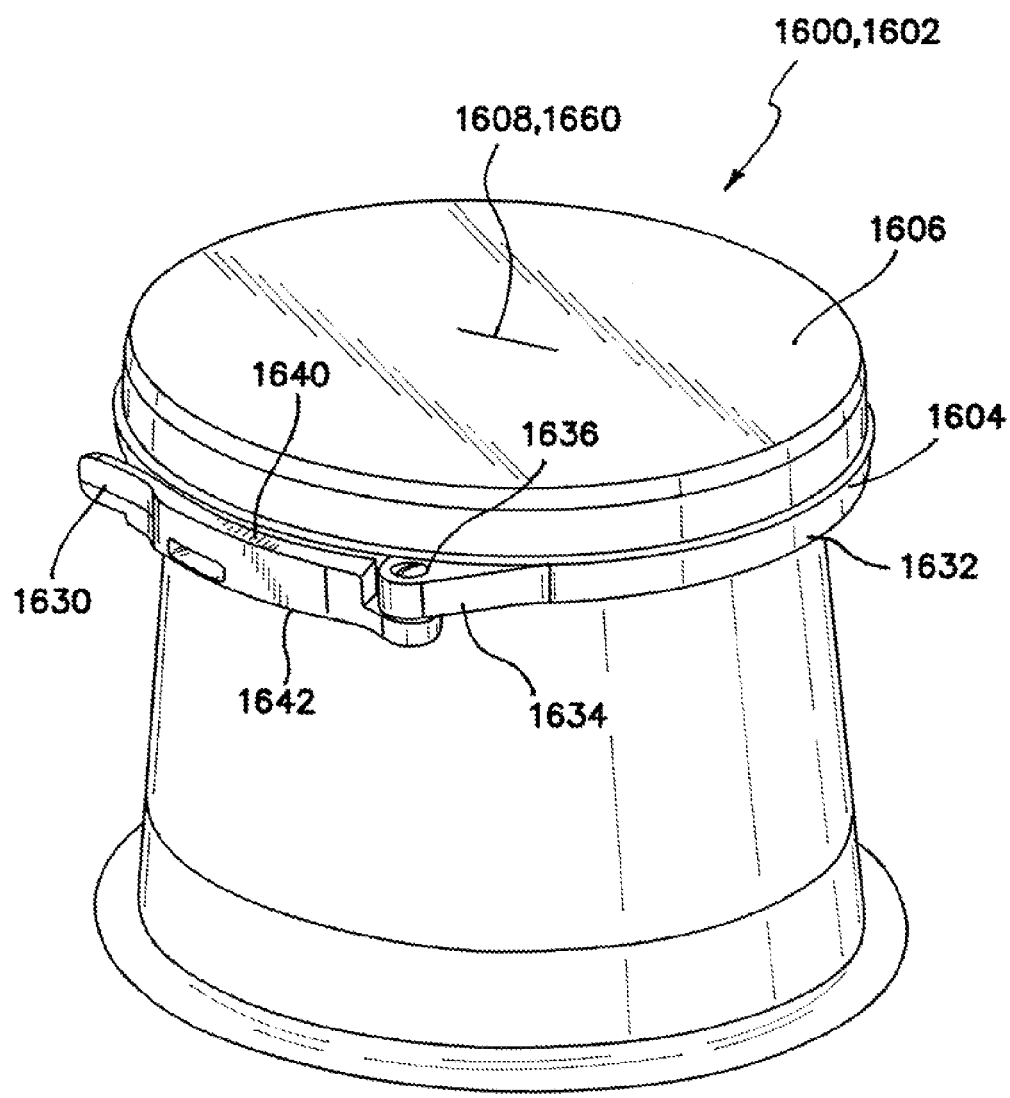
FIG. 77 is a top perspective view of the gel cap of FIG. 70 coupled to the wound retractor.

In use, the wound retractor 100 is first used to retract the incision in the body wall of a patient, as described above. With the lever 1630 in the first state, the gel cap 1602 is brought to the outer ring 102 of the wound retractor 100 at an angle with the lip portion 1624 of the cap ring 1604 toward the patient. The lip portion 1624 of the cap ring is slid under the distal-most circular tube 108, 110 of the outer ring 102, between the outer ring and the patient, and then the remainder of the gel cap 1602 is swung onto the outer ring. The lever 1630 is then swung closed into the second state (FIG. 77). In the second state, the distal lip 1644 of the lever 1630 abuts the distal surface of the distal-most circular tube 108, 110 of the outer ring 102 of the wound retractor 100 and secures the gel cap 1602 to the wound retractor. More particularly, with the gel cap 1602 mounted onto the outer ring 102 of the wound retractor 100 and the lever 1630 positioned in the second state, the lip portion 1624 of the cap ring 1604 and the distal lip 1644 of the lever receive the outer ring of the wound retractor. The outer ring 102 of the wound retractor 100 is positioned between the lip portion 1624 of the cap ring 1604 and the distal lip 1644 of the lever 1630 at the distal end of the outer ring of the wound retractor and the gel pad 1606 at the proximal end of the outer ring of the wound retractor.

Figure 74:
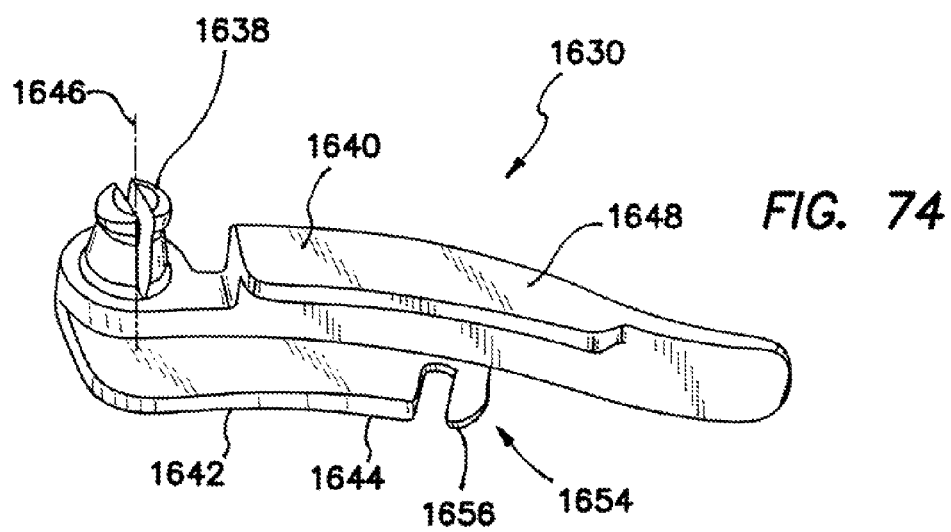
FIG. 74 is a top perspective view of the lever portion of the gel cap of FIG. 70.
Figure 78:
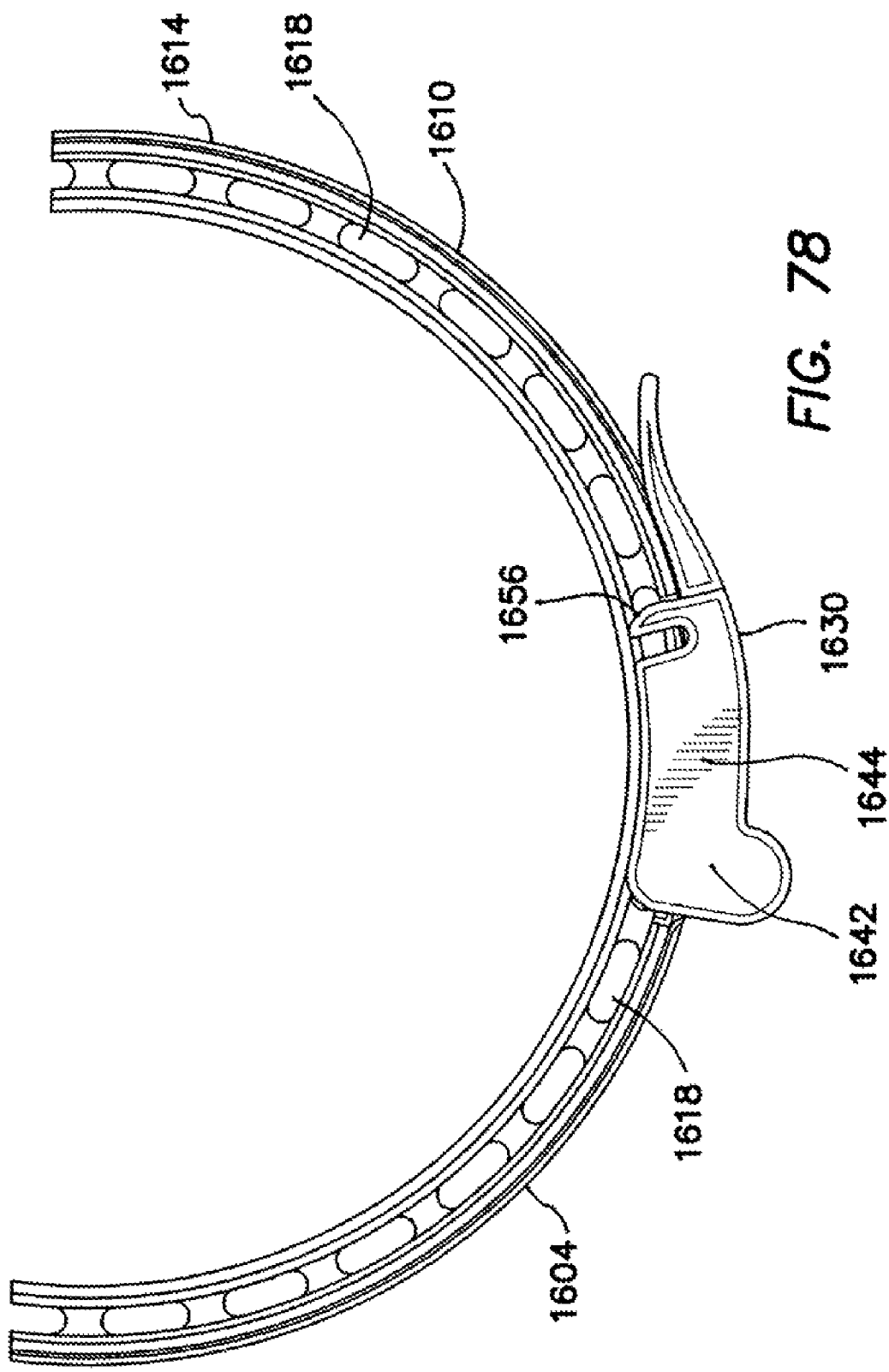
FIG. 78 is a partial bottom view of the cap ring of FIG. 70 with the lever in the second, closed state.
Figure 79:
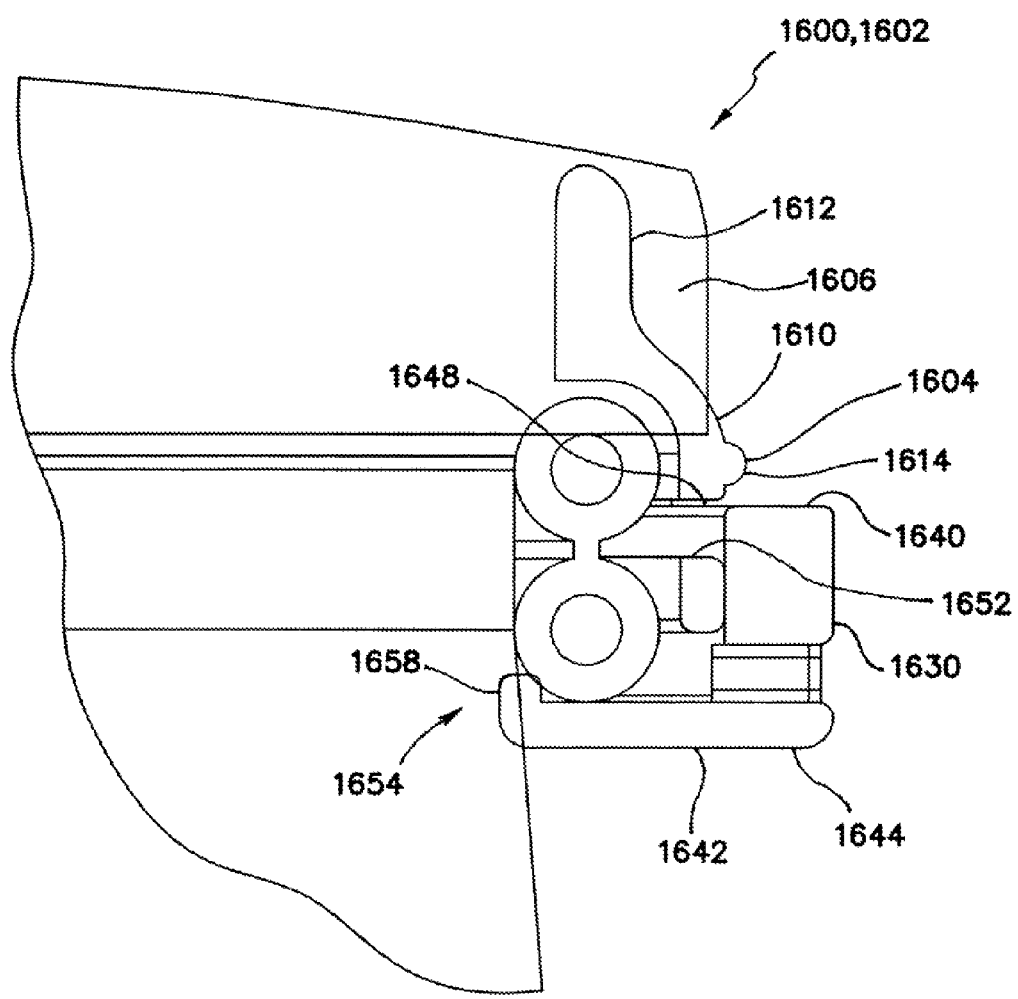
FIG. 79 is a partial section view of the gel cap of FIG. 70 coupled to the outer ring of the wound retractor with the lever in a second, closed state and the lever having a catch for engaging the outer ring of the wound retractor to hold the lever in the closed state.
Figure 80:
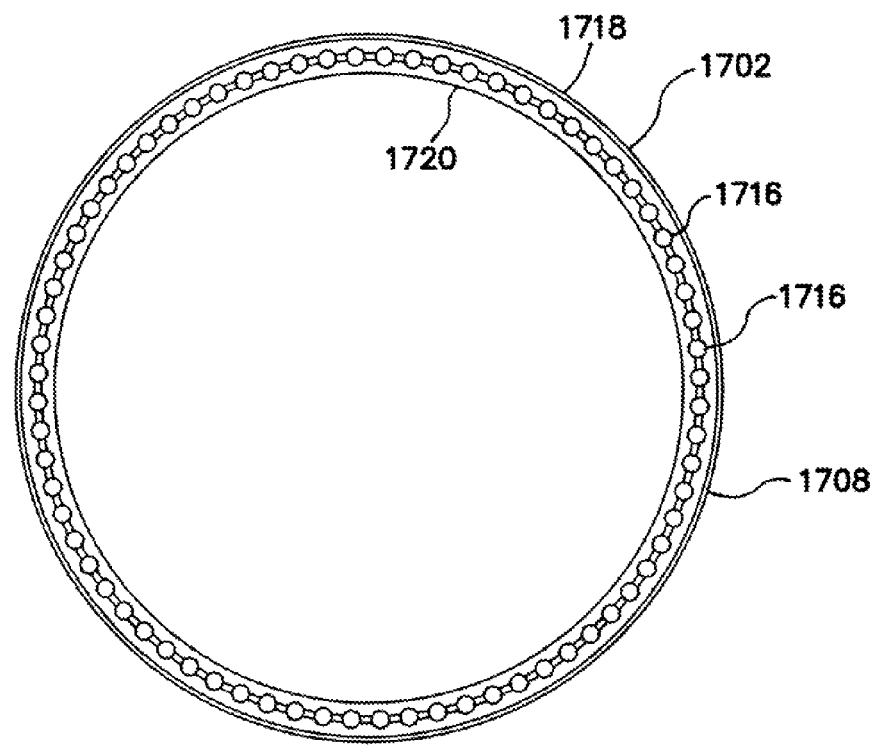
FIG. 80 is a top plan view of a cap ring portion of a gel cap having a plurality of lips for coupling the gel cap to the outer ring of the wound retractor.
Figure 83:
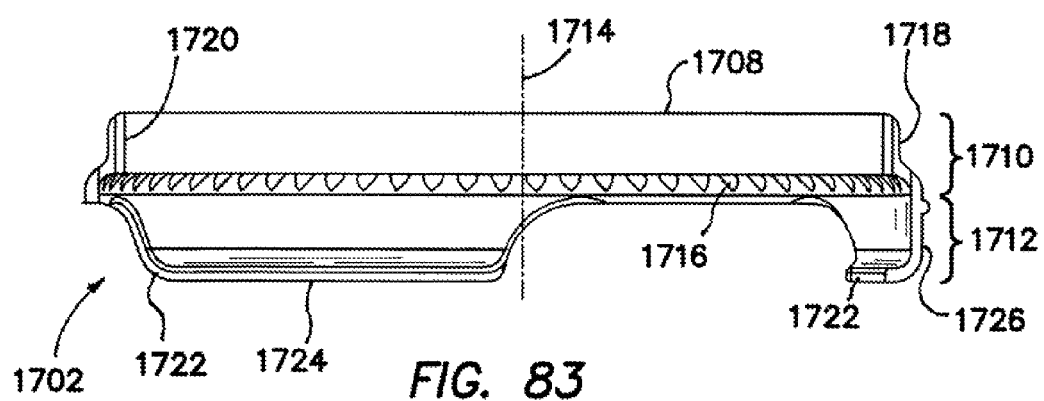
FIG. 83 is a side section view of the cap ring of FIG. 80.
Figure 81:
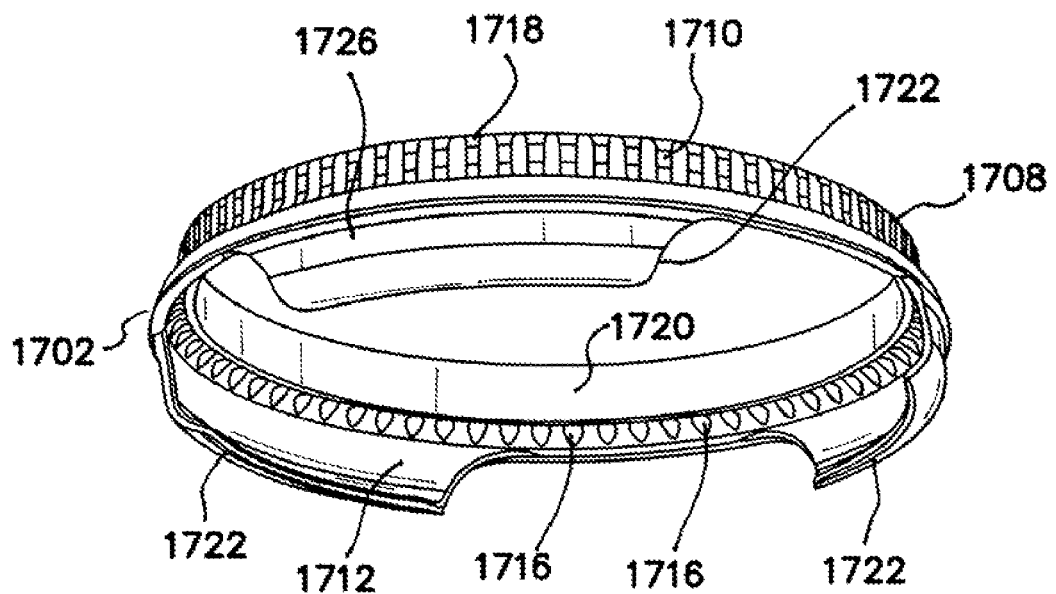
FIG. 81 is a bottom perspective view of the cap ring of FIG. 80 depicting lips for engaging the outer ring of the wound retractor.
Figure 82:
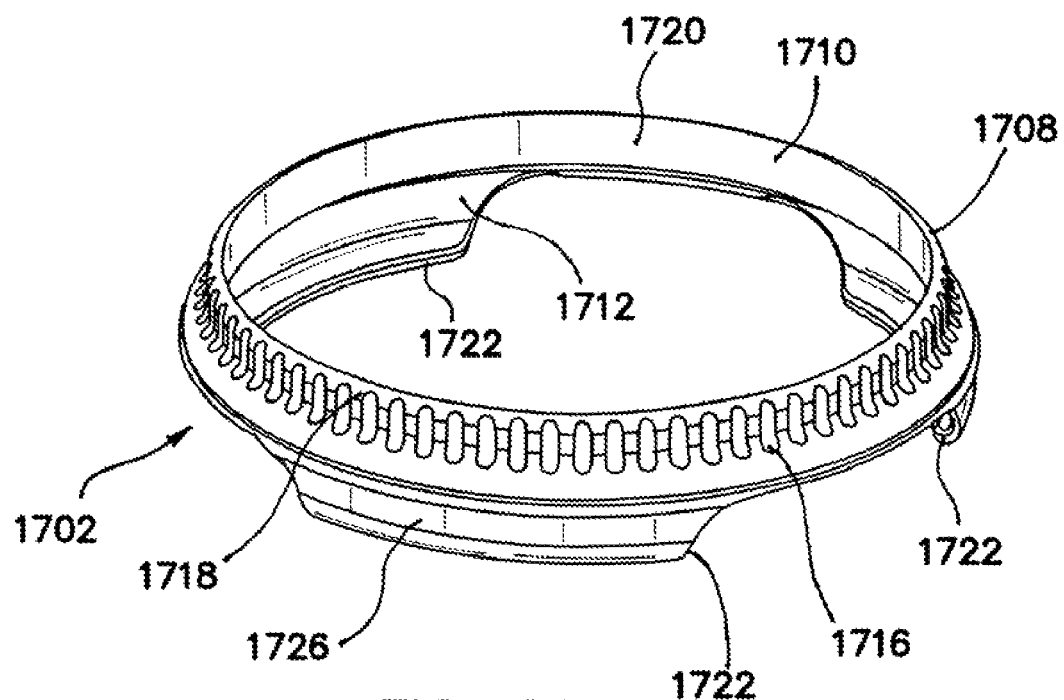
FIG. 82 is a top perspective view of the cap ring of FIG. 80.
Figure 84:
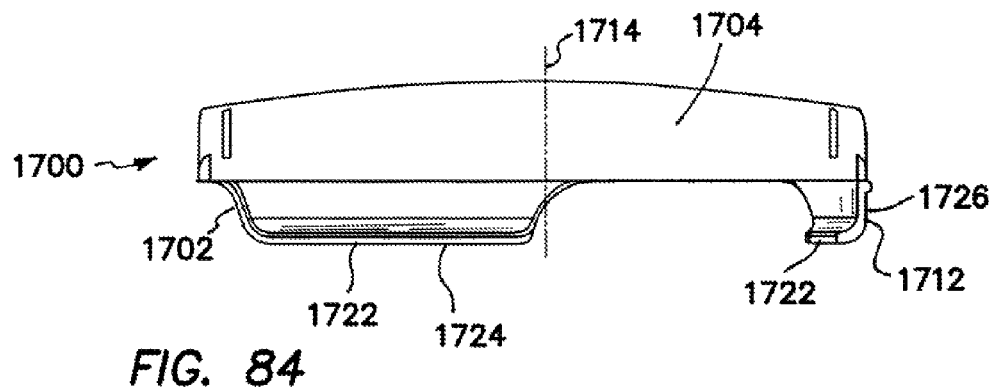
FIG. 84 is a side section view of the gel cap incorporating the cap ring of FIG. 80.
Figure 85:
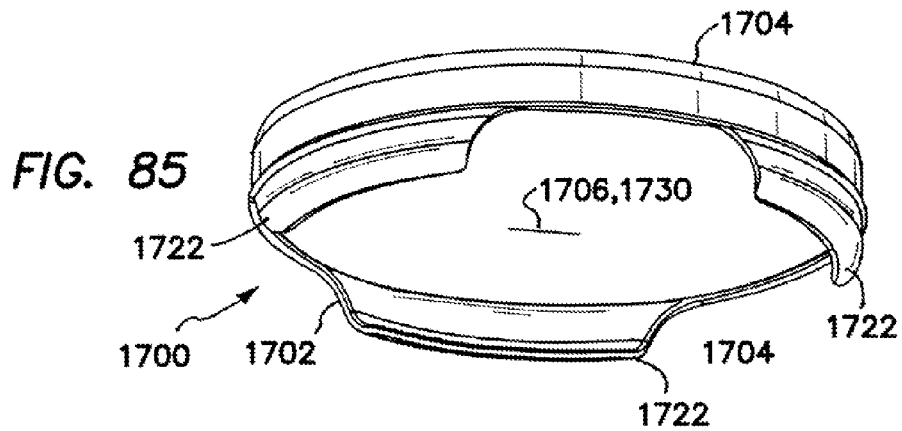
FIG. 85 is a bottom perspective view of the gel cap of FIG. 84.
Figure 86:
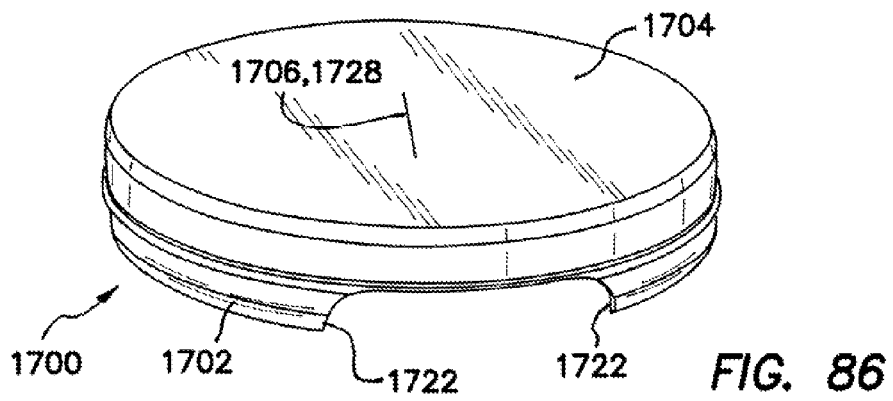
FIG. 86 is a top perspective view of the gel cap of FIG. 84.
Figure 87:
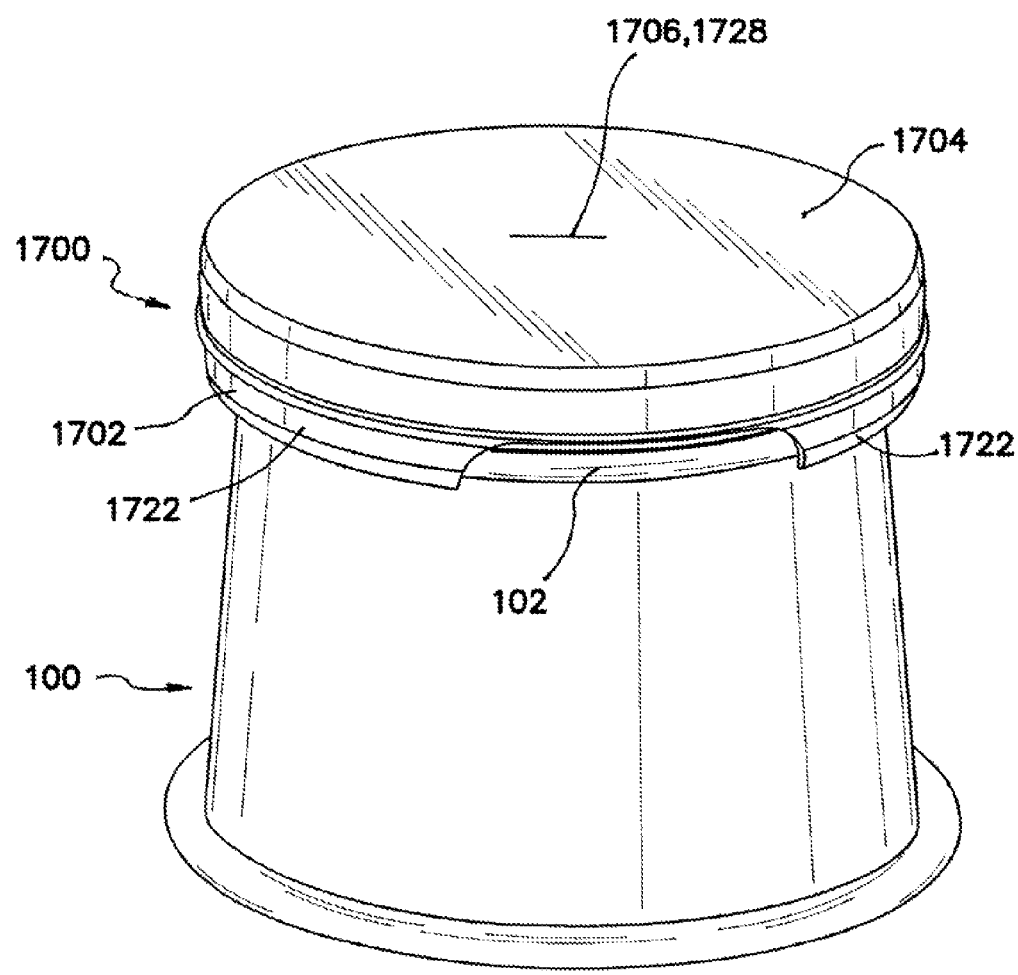
FIG. 87 is a top perspective view of the gel cap of FIG. 84 coupled to the outer ring of the wound retractor.
Figure 88:
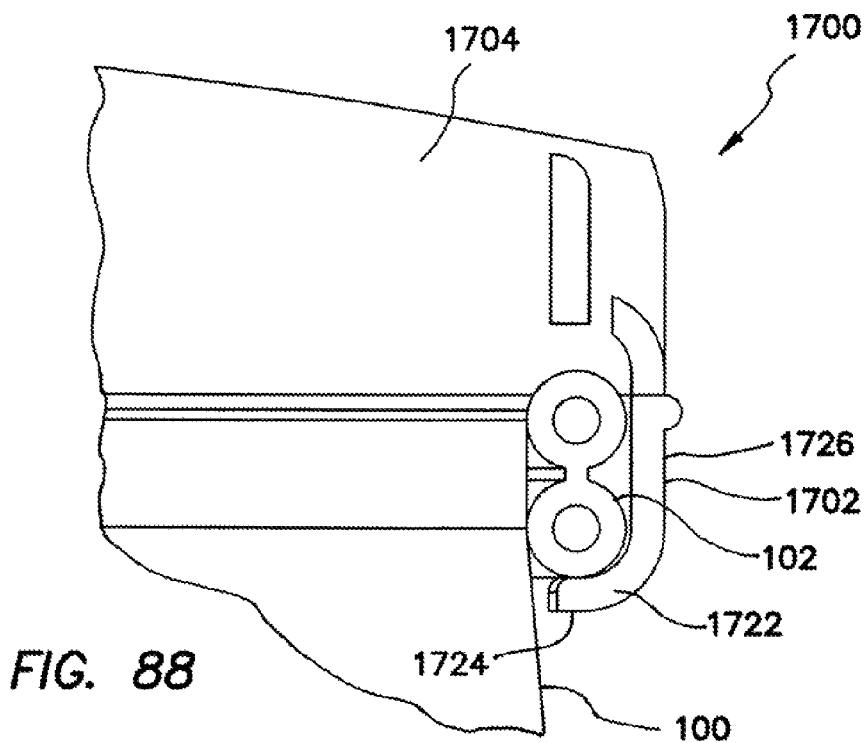
FIG. 88 is a partial section view of the gel cap of FIG. 84 coupled to the outer ring of the wound retractor.
Figure 89:
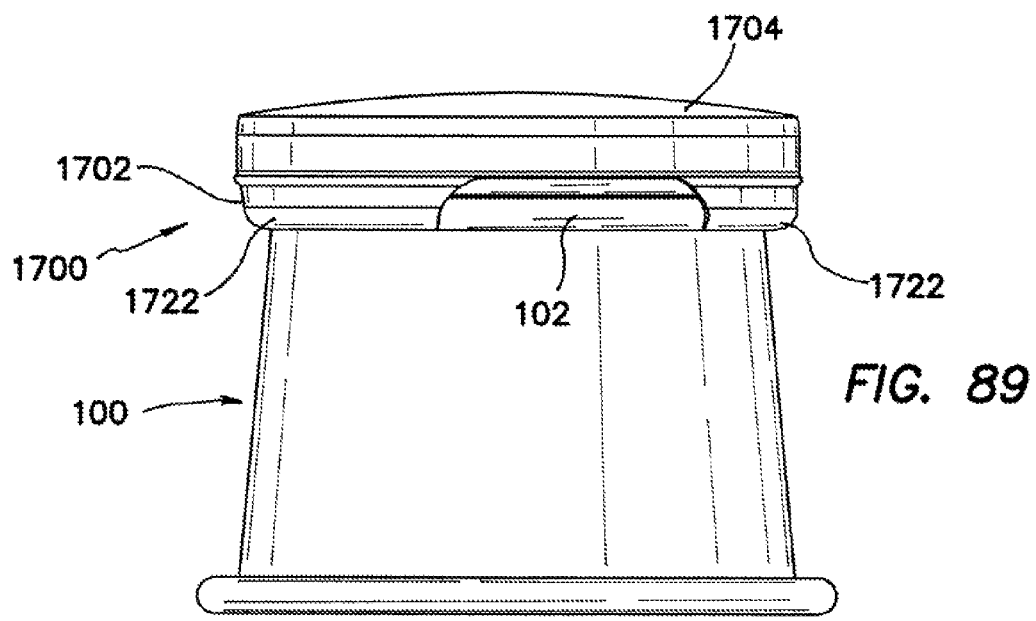
FIG. 89 is a side view of the gel cap of FIG. 84 coupled to the outer ring of the wound retractor.

The lever 1630 includes locking means 1654 (FIG. 74) to prevent unintended opening of the lever from the second state to the first state. In one aspect, to positively lock the lever 1630 into the second state, one of the distal and proximal lips 1644, 1648 of the lever includes a latch 1656 that engages the aperture/groove 1650, 1652 in the cap ring through which the lip protrudes (see FIG. 78). In another aspect, the distal lip 1644 of the lever 1630 includes a catch 1658 (FIG. 79) protruding proximally to engage the distal-most circular tube 108, 110 of the outer ring 102 of the wound retractor 100 at a position on the inner circumference of the outer ring.

With the gel cap 1602 mounted onto the outer ring 102 of the wound retractor 100 and the lever 1630 positioned in the second state, the proximal lip 1648 on the lever positioned in the aperture 1652 in the cap ring 1604 provides support for the lever to counteract cantilever forces induced by the displaced gel of the gel pad 1606. Support of the proximal lip 1648 also helps the distal lip 1644 maintain the position of the outer ring 102 of the wound retractor 100 against the gel pad 1606.

In another aspect, the gel cap 1602 may include more than one lever 1630 with the levers substantially equally spaced between each other and the lip 1624 on the cap ring 1604. In a further aspect, the lip 1624 on the cap ring 1604 may be omitted and at least two levers 1630 used to secure the gel cap 1602 to the wound retractor 100.

The gel cap 1602 with the lip 1624 and lever 1630 on the cap ring is best suited for use with wound retractors 100 having an outer ring 102 that is substantially rigid and noncompliant. If the outer ring 102 of the wound retractor 100 were not rigid, the outer ring would tend to pull out of the gel cap 1602, thereby compromising the seal between the gel pad 1606 and the wound retractor and potentially resulting in deflation of the insufflated body cavity.

In one aspect, cyanoacrylate, e.g., SUPERGLUE or KRAZY GLUE, may be used to bond or otherwise attach the gel pad 1606 to the cap ring 1604. The glue may attach to either the rubber or styrene component of the tri-block and the bond is frequently stronger than the gel material itself. In another aspect, a solvent may be used to dissolve the plastics in the cap ring 1604 and the polystyrene in the gel pad 1606. The solution of solvent is applied to the gel pad 1606 and cap ring 1604 in either a spray or dip form. In effect, the solution melts both the plastic of the cap ring 1604 as well as the polystyrene in the gel pad 1606 to allow a chemical bond to form between the two, which remains when the solvent evaporates.

In one aspect, gel is cast into a DYNAFLEX or KRATON polymer support structure, e.g., the cap ring 1604. By using KRATON polymer or a similar material in the cap ring 1604, ring adhesion between the gel pad 1606 and the cap ring can be achieved. The polystyrene in the gel pad 1606 is identified as achieving adhesion with polyphenylene oxide (PPO), polystyrene and other polymers.

In the casting process the gel pad 1606 and the cap ring 1604 are heated to a temperature above about 130° C. and held at that temperature for several hours, e.g., about three (3) to four (4) hours. The temperature used is not sufficient to deform the cap ring 1604.

The cap ring 1604 in one aspect includes a polymer, e.g., polyethylene (PE). In one aspect, the polyethylene is a low density polyethylene (LDPE) or high density polyethylene (HDPE), or ultra high molecular weight polyethylene (UHM-WPE). In one aspect, the cap ring 1604 may be made of a polymer, such as polycarbonate and may be fabricated by methods including injection molding.

The gel includes mineral oil. PE has a higher molecular weight than mineral oil. PE is dissolved by mineral oil at high temperatures. As such, as the PE and the mineral oil in the gel pad intermix as both are heated to and held at temperatures above about 130° C., a bond between the PE and gel pad is formed.

In one aspect, the cap ring 1604 includes polycarbonate. The polycarbonate of the cap ring 1604 does not form bonds with gel at 130° C. However, by raising the temperature to about 150° C. for a few minutes during casting, bonding occurs between the gel pad 1606 and the cap ring 1604. As such, heating the gel pad 1606 and cap ring 1604 to temperatures at which both the polystyrene of the gel and the polycarbonate are simultaneously beyond their melt points allows bonds to form between the gel pad 1606 and the cap ring 1604. Alternatively, the gel pad 1606 and cap ring 1604 may be heated to near or at the glass transition temperature of the polycarbonate cap ring to form the bond between the gel pad and the cap ring.

Referring to FIGS. 80-89, another embodiment of a gel cap 1700 includes a cap ring 1702 that couples to the outer ring 102 of the wound retractor 100 and a gel pad 1704 coupled to the cap ring. Similar to the aspect of the gel cap 1602, the gel pad 1704 is made of a gel material and includes an access portion 1706 or passage through the gel for providing a passage from external the body to the body cavity 404. In one aspect, the access portion 1706 may include a plurality of intersecting dead-end slits 1728, 1730. The access portion 1706 forms an instrument seal in the presence of an instrument, such as the arm of a surgeon, inserted therethrough and a zero seal in the absence of an instrument inserted therethrough.

To combine the gel pad 1704 with the cap ring 1702, the cap ring may be placed into a mold that includes the shape of the desired gel pad and the uncured gel is added to the mold. In one aspect, the cap ring 1702 includes a substantially cylindrical ring 1708 having a first, proximal portion 1710, a second, distal portion 1712 and a longitudinal axis 1714 extending through the proximal and distal portions. The gel pad 1704 is positioned at the proximal portion 1710 of the cap ring 1702. The proximal portion 1710 of the cap ring 1702 may include a plurality of apertures 1716 distributed about the circumference of the cap ring. The apertures 1716 may extend through the wall of the proximal portion 1710 of the cap ring 1702. Sufficient gel may be added to the mold to cover and fill the apertures 1716. When adding uncured gel into the mold, the gel flows through the apertures 1716 and remains in the apertures. Also, for reasons that will be described below, sufficient gel may be added to the mold to extend into the distal portion 1712 of the cap ring 1702. When the gel pad 1704 is cured, the gel in the apertures 1716 connects the gel at the outer portion 1718 of the cap ring 1702 to the gel at the inner portion 1720 of the cap ring, thus forming a mechanical lock between the gel and the cap ring.

The distal portion 1712 of the cap ring 1702 is substantially cylindrical and is configured to receive the outer ring 102 of the wound retractor 100. In one aspect, the distal portion 1712 of the cap ring 1702 includes a plurality of lips 1722 at the distal end 1724 thereof. The lips 1722 curve radially inwardly from the wall 1726 of the distal portion 1712 of the cap ring 1702 and extend around a portion of the circumference of the cap ring. In one aspect, there are three lips 1722 equally spaced about the circumference of the distal portion 1712 of the cap ring 1702. Each of the three (3) lips may extend about 60° around the circumference of the cap ring 1702; however, the lips may extend longer or shorter distances around the circumference of the cap ring. Also, there may be more lips 1722 with each lip extending a shorter distance around the circumference of the cap ring 1702 and the more than three lips being substantially equally spaced about the circumference of the distal portion of the cap ring. In another aspect, there may be two lips 1702 that are substantially diametrically opposed about the circumference of the distal portion of the cap ring with each of the lips extending a sufficient distance around the circumference of the cap ring 1702 to facilitate adequate coupling of the gel cap 1700 to the outer ring 102 of the wound retractor 100. The lips 1722 are configured to receive the distal-most circular tube 108, 110 of the outer ring 102 of the wound retractor 100 such that the outer ring is positioned between the lips 1722 and the gel pad 1704. More particularly, when the outer ring 102 of the wound retractor 100 is received by the distal portion 1712 of the cap ring 1702, the outer ring of the wound retractor embeds into the gel pad 1704 at the distal portion 1712 of the cap ring 1702 and displaces the gel, thereby forming a seal between the gel pad and the outer ring and sleeve 106 of the wound retractor. This places the gel pad 1704 in juxtaposition with the incision 400.

In use, the wound retractor 100 is first used to retract the incision in the body wall of a patient, as described above. The gel cap 1700 is brought to the outer ring 102 of the wound retractor 100 at an angle, with one of the lip portions 1722 of the cap ring 1702 toward the patient. The lip portion 1722 of the cap ring that is toward the patient is slid under the distal-most circular tube 108, 110 of the outer ring 102, between the outer ring and the patient, and then the remainder of the gel cap 1700 is swung onto the outer ring with the remaining lip portions snapping into place under the distal-most circular tube. In an alternative aspect, the gel cap 1700 may be brought to the outer ring 102 substantially parallel to the outer ring and the lip portions 1722 snapped into place under the distal-most circular tube 108, 110 of the outer ring 102 at the same time.

The gel cap 1700 with the plurality of lips 1722 on the cap ring 1702 is best suited for use with wound retractors 100 having an outer ring 102 that is substantially rigid and noncompliant. If the outer ring 102 of the wound retractor 100 were not rigid, the outer ring would tend to pull out of the gel cap 1700, thereby compromising the seal between the gel pad 1704 and the wound retractor and potentially resulting in deflation of the insufflated body cavity.

The cap ring 1702 in one aspect includes a polymer, e.g., polyethylene (PE). In one aspect, the polyethylene is a low density polyethylene (LDPE) or high density polyethylene (HDPE), or ultra high molecular weight polyethylene (UHMWPE). In one aspect, the cap ring 1702 may be made of a polymer, such as polycarbonate and may be fabricated by methods including injection molding.

Figure 90:
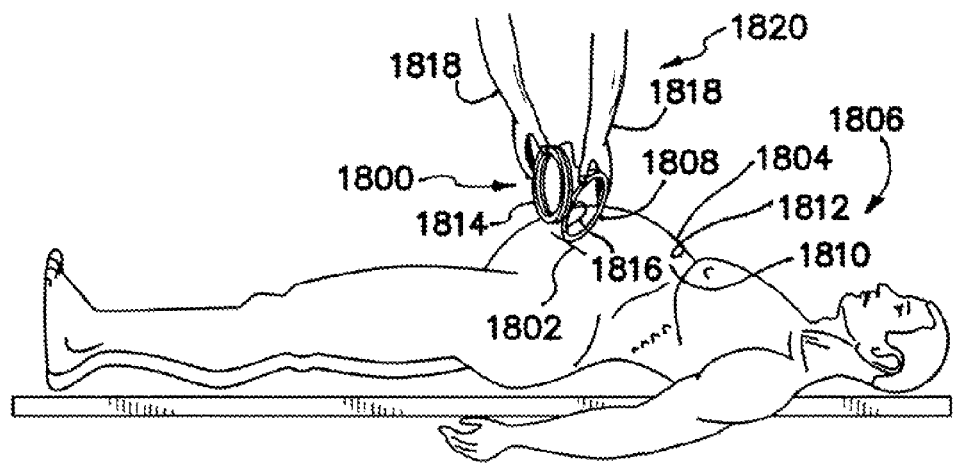
FIG. 90 depicts a technique for placing a surgical wound retractor within an incision.
Figure 91:
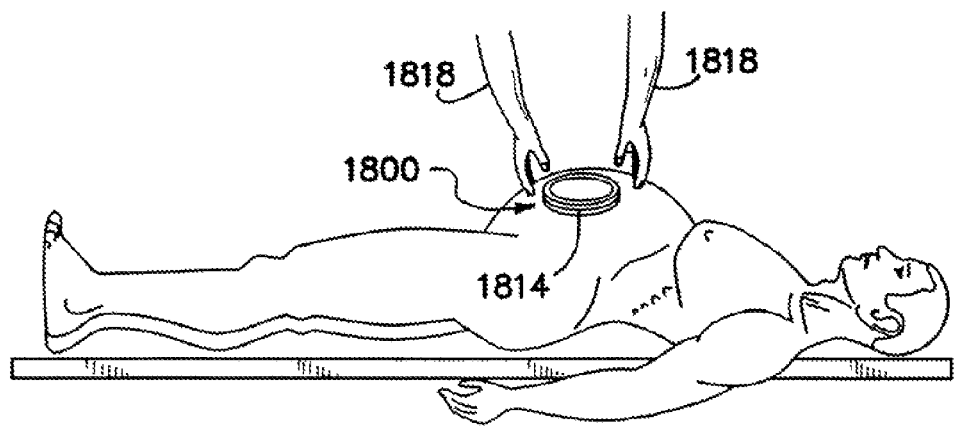
FIG. 91 depicts the surgical wound retractor within an incision.

Referring to the drawings, FIGS. 90 and 91 depict the placement of a wound retractor 1800 into an incision 1802 made through a body wall 1804 of a patient 1806. Generally, a first, inner ring 1808 is deformed and placed into the incision 1802. The first, inner ring 1808 is released when it has passed through the body wall 1804 of the patient 1806 and has reached a body cavity 1810 or a reasonably open space. The inner ring 1808 typically returns to a substantially circular condition and is subsequently drawn or pulled outwardly and against the inner surface 1812 of the body wall 1804. Tension between the inner ring 1808 and the external components, such as a second, outer ring 1814, of the wound retractor 1800 is transmitted by means of a substantially cylindrical distensible sleeve 1816 that is coupled between the inner ring 1808 and the outer ring 1814. Tension is increased between the inner and outer rings 1808, 1814 by winding the sleeve 1816 upon the second, outer ring. As the sleeve 1816 is shortened, it supplies a retracting or opening force away from the axis of the assembled wound retractor 1800. The second, outer ring 1814 is easily turned upon itself or inverted by the use of one or two hands 1818 of a single user 1820 and does not require the use of tools or assistants.

Figure 92:
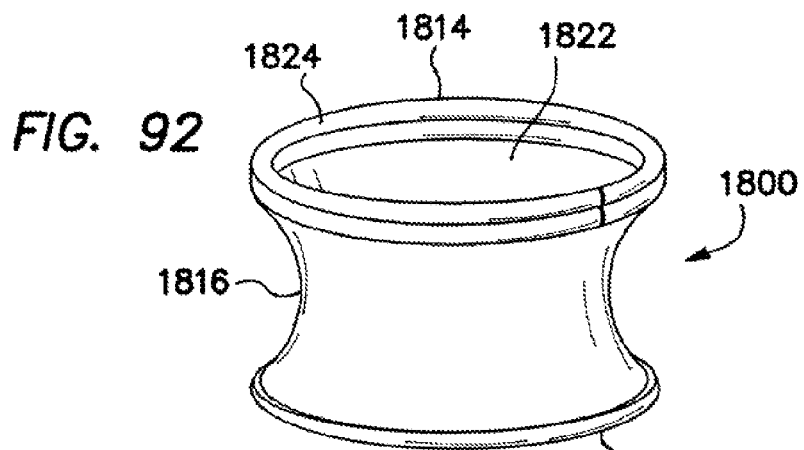
FIG. 92 is a perspective view of an assembled surgical wound retractor.
Figure 93:
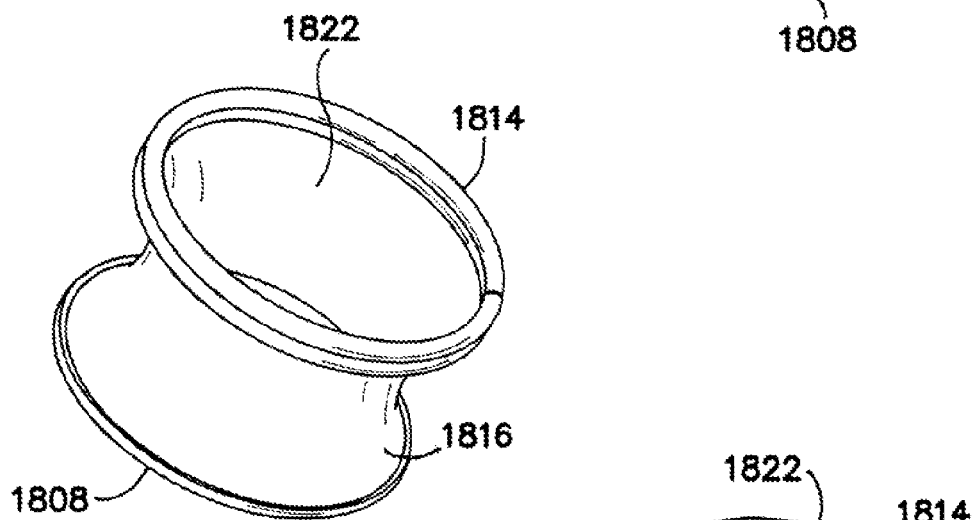
FIG. 93 is a perspective view of an assembled surgical wound retractor of FIG. 92.
Figure 94:
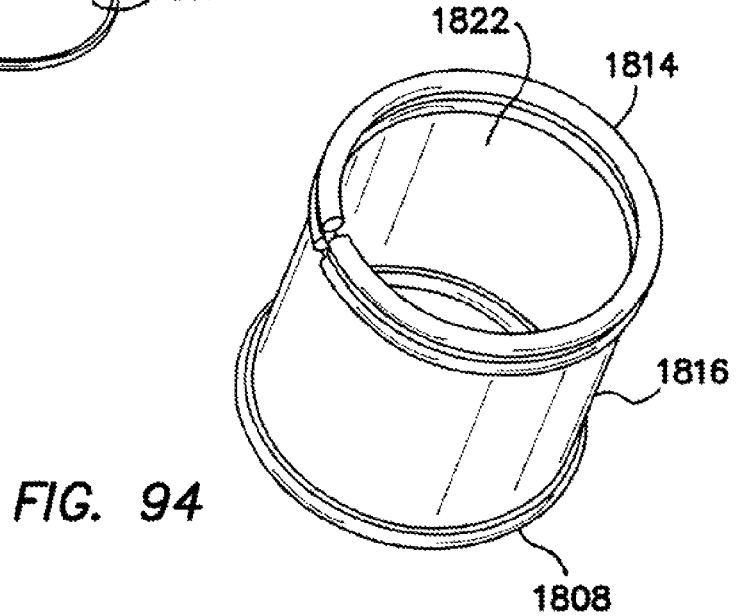
FIG. 94 is a perspective view of an assembled surgical wound retractor having a rigid central support in an outer ring of the wound retractor.
Figure 95:
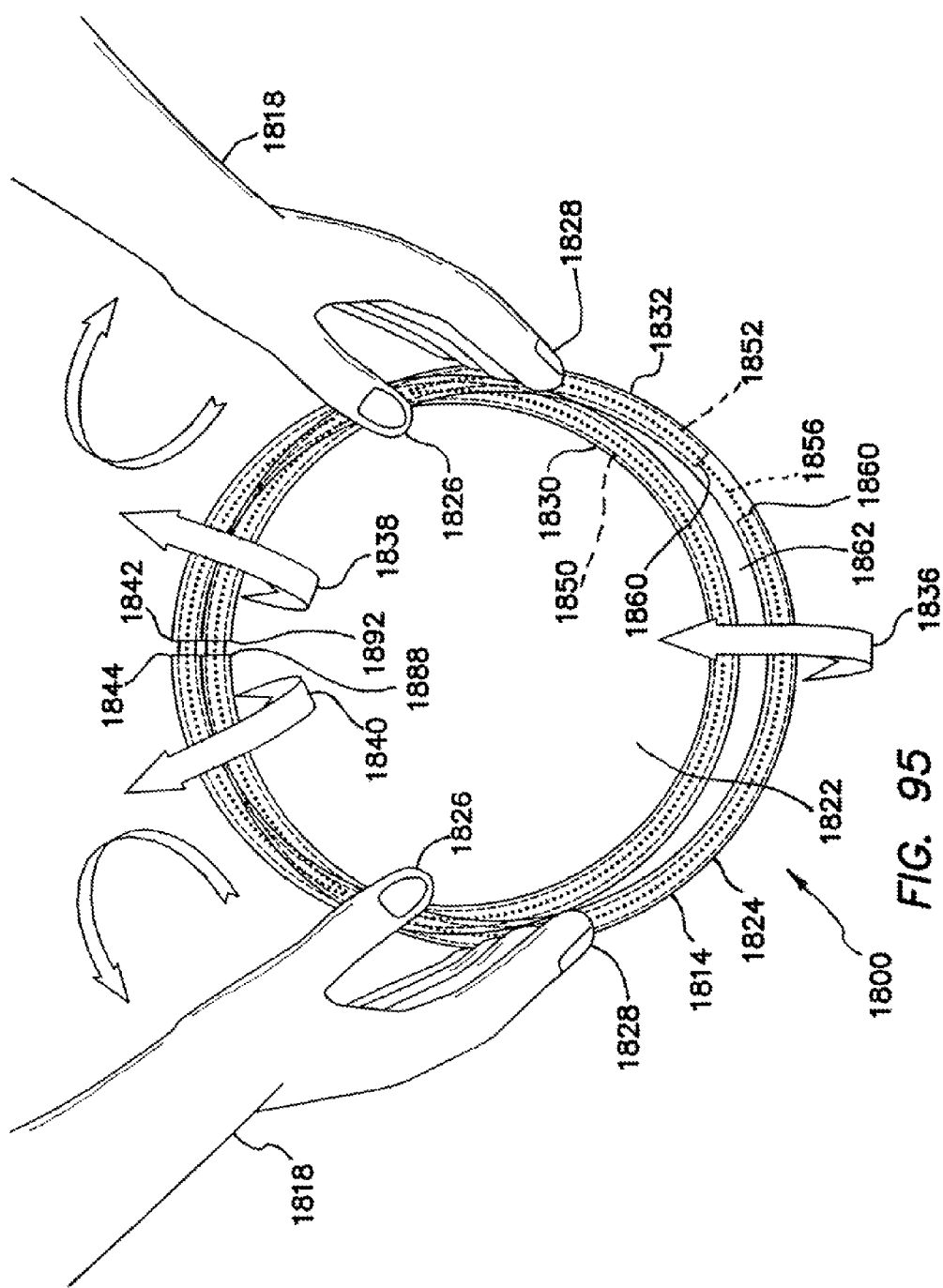
FIG. 95 is a plan view depicting a first step of a technique employed to wind a sleeve of a wound retractor upon the rigid outer ring of the wound retractor.
Figure 96:
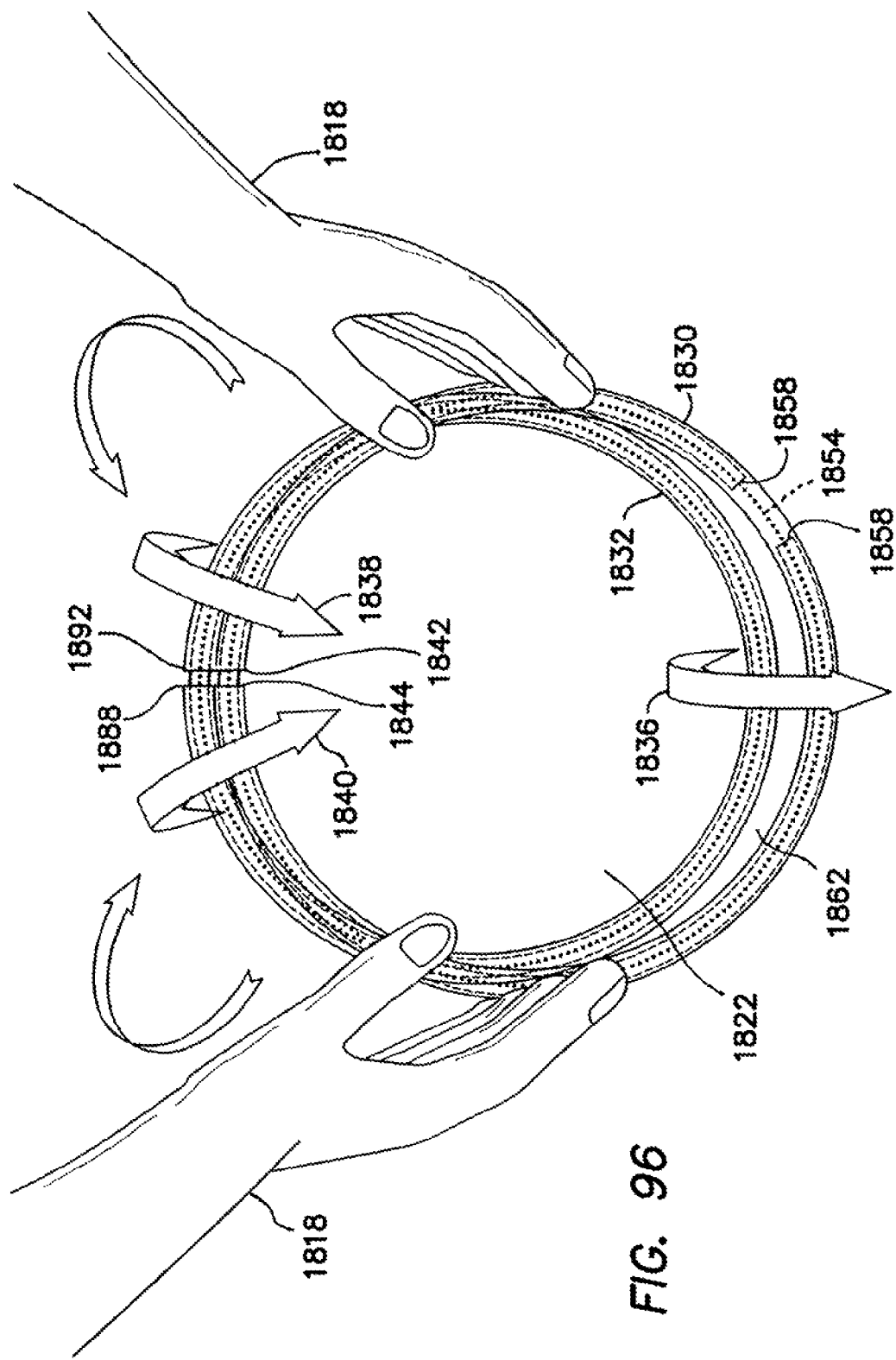
FIG. 96 is a plan view depicting a second step of the technique employed to wind the sleeve of the wound retractor upon the rigid outer ring of the wound retractor.
Figure 97:
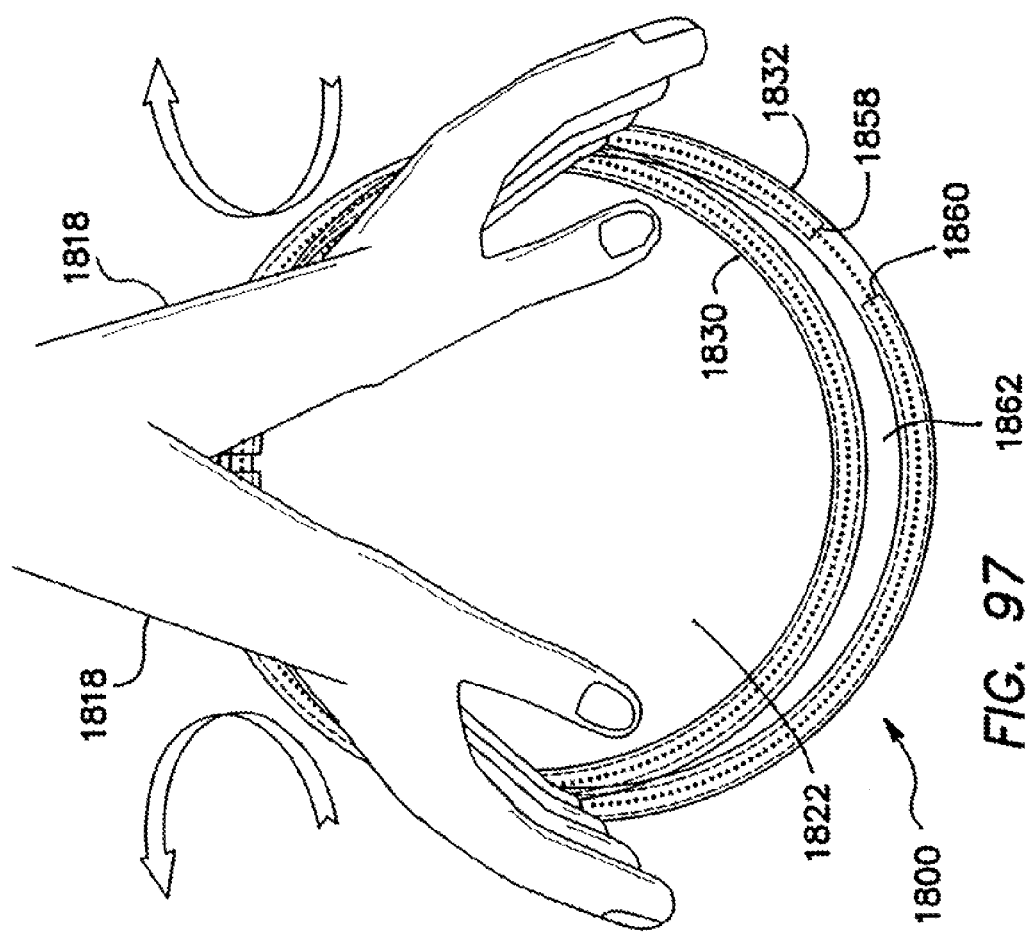
FIG. 97 is a plan view depicting a third step of the technique employed to wind the sleeve of the wound retractor upon the rigid outer ring of the wound retractor.
Figure 98:
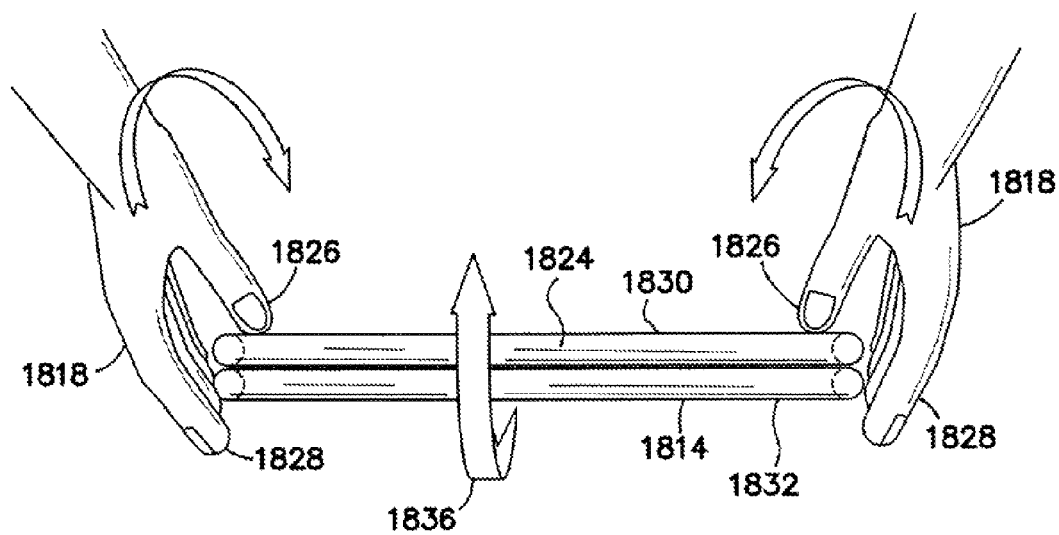
FIG. 98 is a side view depicting the first step of the technique employed to wind the sleeve of the wound retractor upon the rigid outer ring of the wound retractor.
Figure 99:
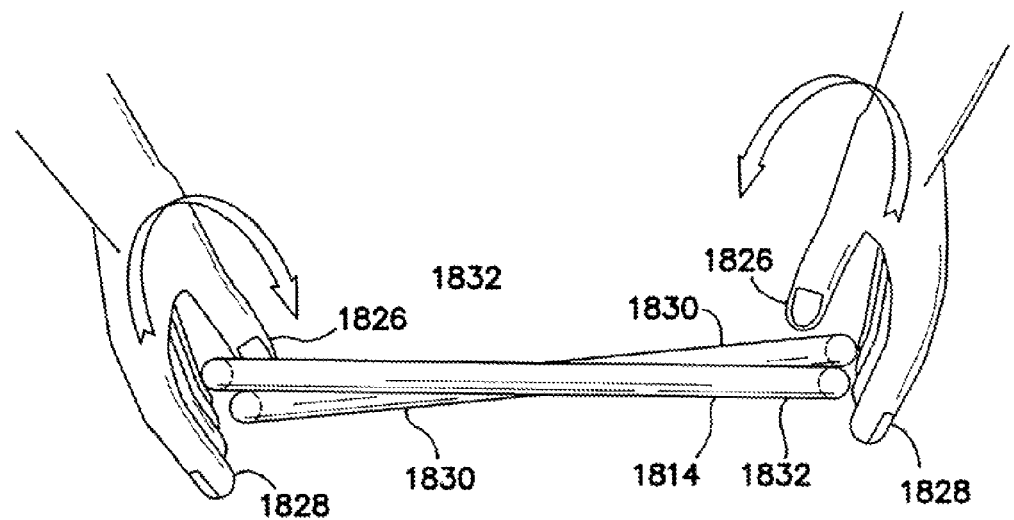
FIG. 99 is a side view depicting the second step of the technique employed to wind the sleeve of the wound retractor upon the rigid outer ring of the wound retractor.
Figure 102A:
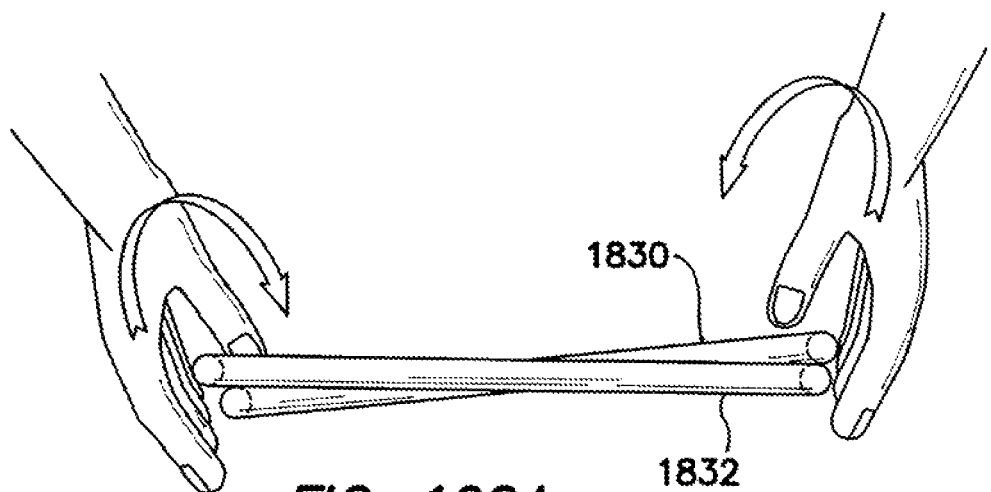
FIGS. 102A through 102C are side views depicting the sequence of winding the sleeve upon the rigid outer ring of the wound retractor.
Figure 102B:
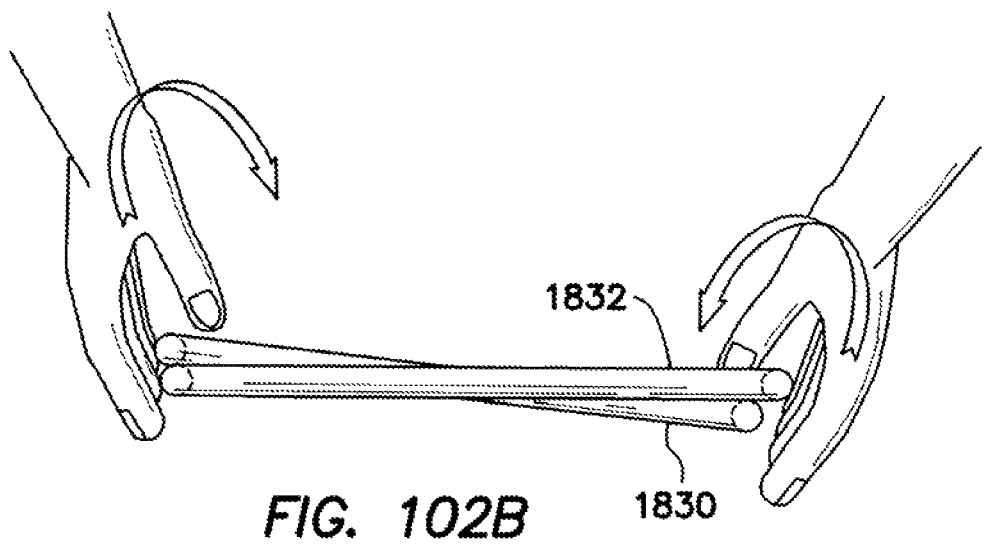
Figure 102C:
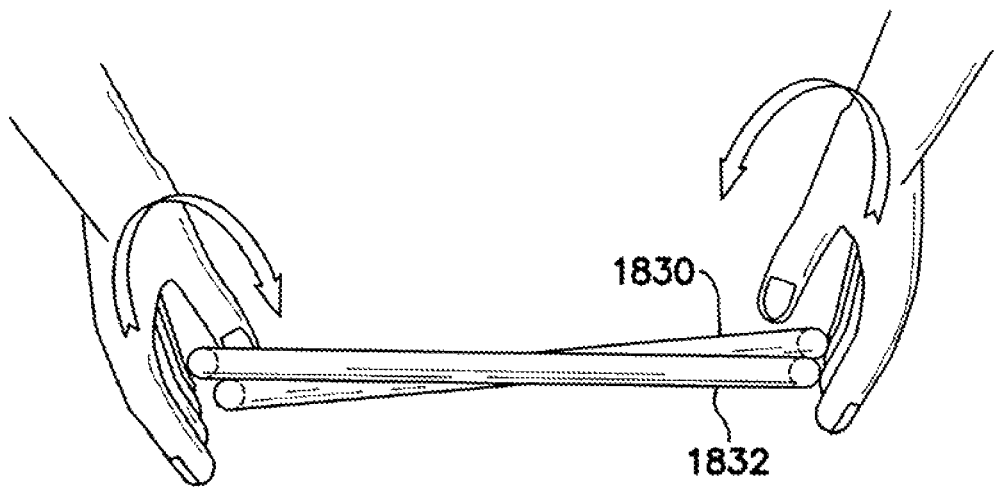
Figure 103A:
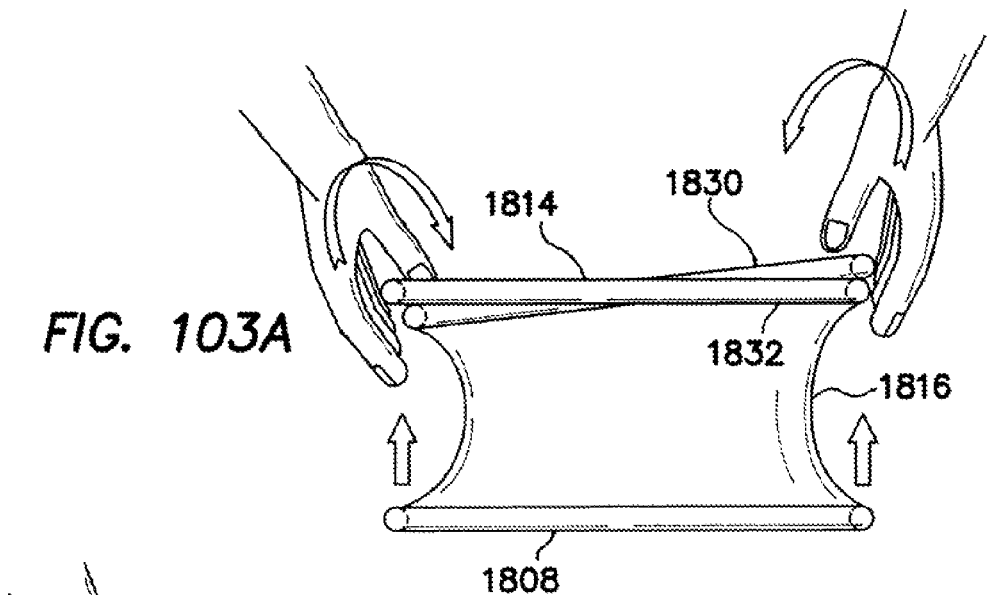
FIGS. 103A through 103C are side views depicting the proportions of changes of the length of the sleeve as the winding of the sleeve progresses.
Figure 103B:
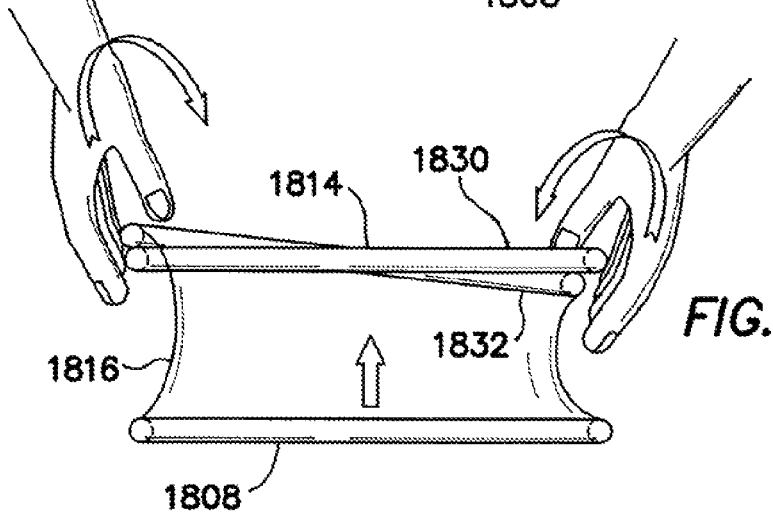
Figure 103C:
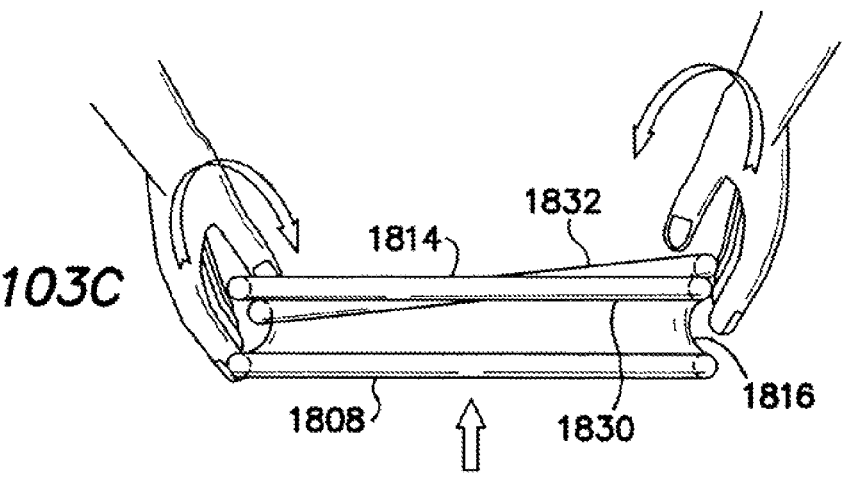
Figure 104:
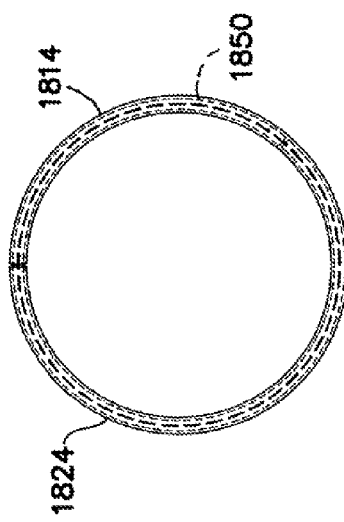
FIG. 104 is a plan view of the rigid outer ring of the wound retractor in a normal at-rest state.
Figure 106:
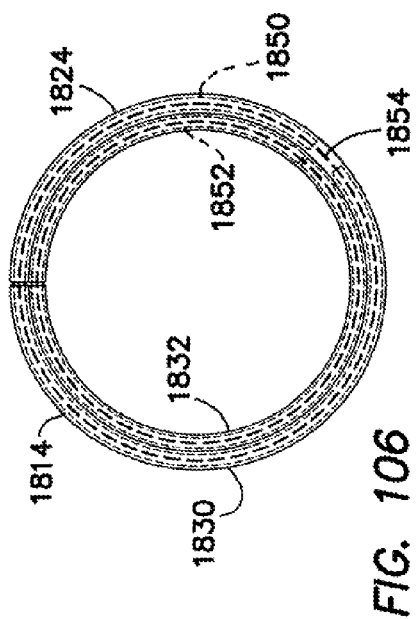
FIG. 106 is a plan view of the rigid outer ring of the wound retractor in a first winding state.
Figure 105:
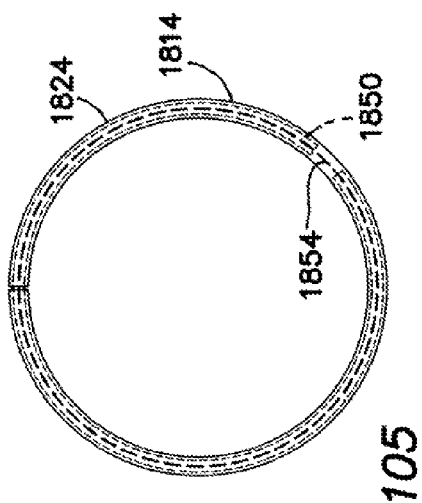
FIG. 105 is a plan view of the rigid outer ring of the wound retractor in an expanded state.
Figure 107:
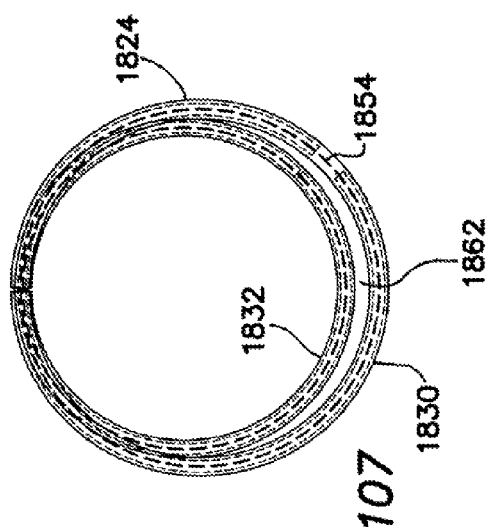
FIG. 107 is a plan view of the rigid outer ring of the wound retractor in a second winding state.
Figure 108:
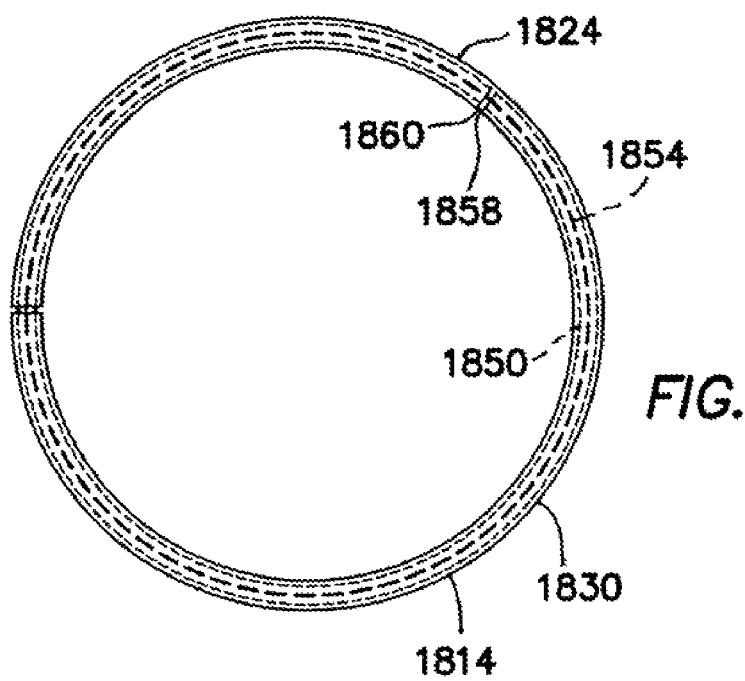
FIG. 108 is a plan view of the rigid outer ring in a normal at-rest state.
Figure 109:
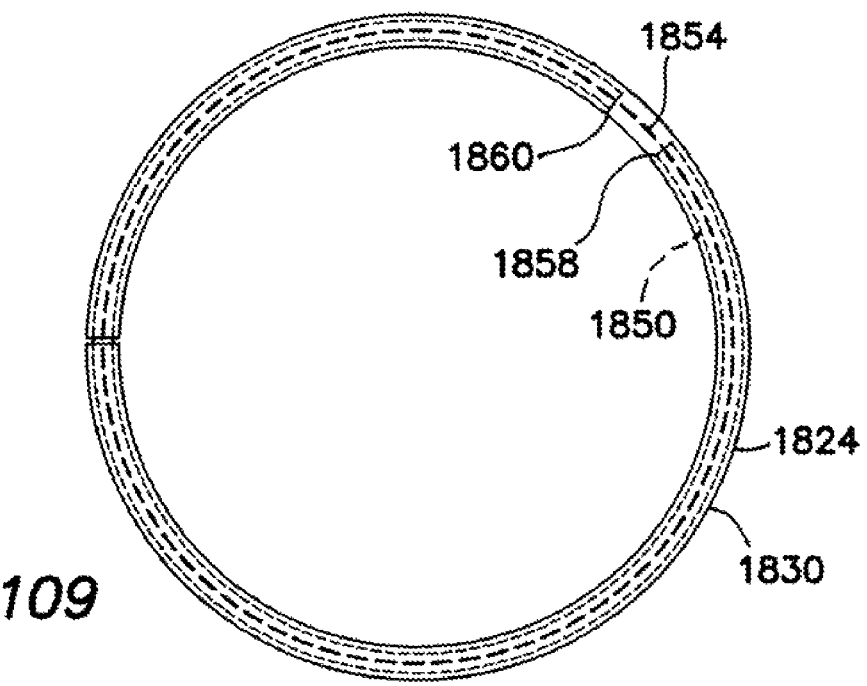
FIG. 109 is a plan view of the rigid outer ring in an expanded state.
Figure 110:
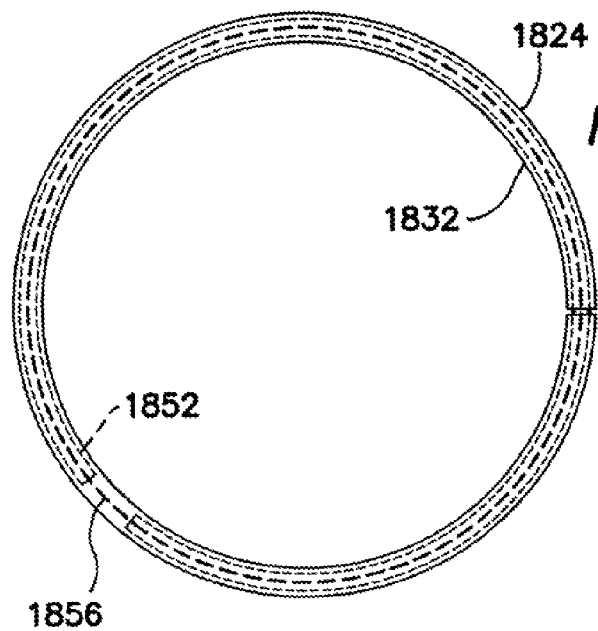
FIG. 110 is a plan view depicting the positioning of a first rigid tube within the outer ring.
Figure 112:
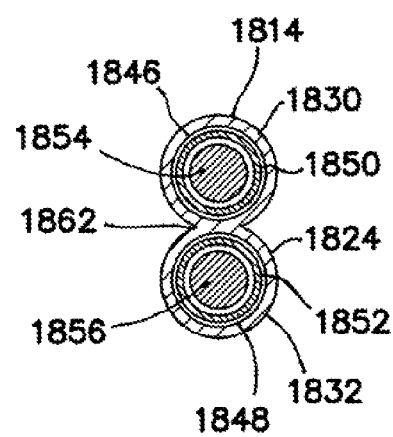
FIG. 112 is a detail section view of the rigid outer ring.
Figure 111:
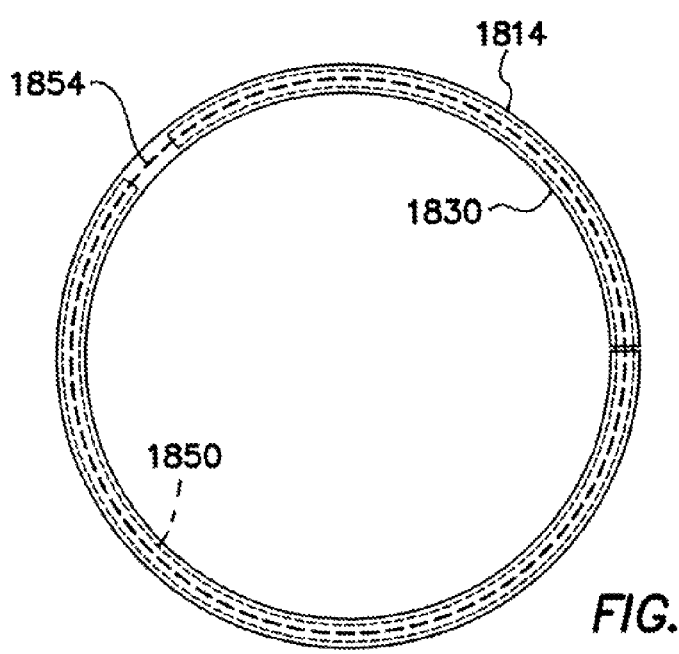
FIG. 111 is a plan view depicting the positioning of a second rigid tube within the outer ring.

Referring to FIGS. 92-94, the inner ring 1808 of the wound retractor 1800 may be circular, oval, elliptical or otherwise shaped to provide easy insertion through the incision 1802 (FIG. 90) or opening in the body wall 1804 (FIG. 90) and appropriate retraction once in place. The cylindrical sleeve 1816 may be made from a thin film and include a first, distal end that is coupled to the inner ring 1808. The sleeve 1816 has a diameter and a length that forms an open central region 1822 that is appropriate for the required retraction and thickness of the body wall 1804 (FIG. 90). A second, proximal end of the sleeve 1816 is coupled to the second, outer ring 1814 that is sized and configured to provide a rigid, noncompliant, substantially circular structure. The rigid, noncompliant outer ring 1814 may include an extruded or molded profile that facilitates an inversion step for winding the sleeve 1816 upon the outer ring.

The process of winding the sleeve 1816 upon the outer ring 1814 is illustrated in FIGS. 95-103. A user 1820 (FIG. 90) grasps the outer ring 1814 and rolls it inwardly toward the center of the wound retractor 1800. The user 1820 may roll the outer ring 1814 sequentially or asymmetrically using one hand 1818 at a time, or the user may use both hands symmetrically. The outer ring 1814 may be rolled over and over several times, resulting in a shortening of the functional length of the sleeve 1816 coupled thereto. The outer ring 1814 is substantially rigid and noncompliant and, therefore, requires considerable force to invert or roll. An object of the invention is to minimize the force required to invert the outer ring 1814 and increase the tension upon the sleeve 1816. A very soft plastic or rubber material may be used to make a first circular tube 1830 and a second circular tube 1832 of a multiple-tube outer cover portion 1824 of the outer ring 1814, such as a double-tube outer ring or a triple-tube outer ring. The soft material favors traction between the outer ring 1814 and the hands 1818 of the user 1820. The rolling or inverting may, therefore, be accomplished with the thumbs 1826 and fingertips 1828 of the user 1820.

The first circular tube 1830 of the outer ring 1814 rotates through the open central region 1822 of the second circular tube 1832 of the outer ring, resulting in a first winding of the sleeve 1816. The second circular tube 1832 of the outer ring 1814 may then be rotated through the open central region 1822 of the first circular tube 1830 of the outer ring, resulting in a second winding of the sleeve 1816. These actions may be repeated until appropriate tension is placed upon the sleeve 1816 and sufficient retraction 1834 (FIG. 101) is applied to the incision 1802 (FIG. 90) in the body wall 1804. In one aspect, the hands 1818 of the user 1820 alternately move the first circular tube 1830 of the outer ring 1814 through the central region 1822 of the second circular tube 1832 of the outer ring and so on in a first direction (FIG. 95) 1836, 1838, 1840 that results in a winding of the sleeve 1816 outwardly and away from the axis of the wound retractor 1800. Alternatively, the hands 1818 of the user 1820 alternately move the first circular tube 1830 of the outer ring 1814 through the central region 1822 of the second circular tube 1832 of the outer ring and so on in a second direction (FIG. 96) that results in a winding of the sleeve 1816 inwardly toward the axis of the wound retractor 1800. The inner ring 1808 of the wound retractor 1800 is adapted for juxtaposition with the inner surface 1812 of the body wall 1804 and the outer ring 1814 of the wound retractor is adapted for juxtaposition with the outer surface of the body wall. Both the inner ring 1808 and the outer ring 1814 are adapted for disposition relative to the incision 1802 in the body wall 1804. The sleeve 1816 is adapted to traverse the incision 1802 in the body wall 1804.

The construction of the rigid, noncompliant outer ring 1814 is further detailed in FIGS. 95, 96 and 104-112 where a generally circular structure is shown having a flexible, elastomeric plastic or rubber extrusion or molded elongate body 1824 having a first end 1842 and a second end 1844. The outer ring 1815 of the wound retractor 1800 also includes at least one lumen. In one aspect, the outer ring 1814 of the wound retractor 1800 includes a first lumen 1846 and a second lumen 1848 extending from the first end 1842 to the second end 1844 through the elongate body 1824. This construction generally favors an extrusion manufacturing method.

A rigid, noncompliant metal or plastic tubular hoop 1850 extends from the first end 1842 of the elongate body to the second end 1844 of the elongate body 1824. The rigid, noncompliant tubular hoop 1850 may be made from a substantially straight tube and bent or formed into an open circular form having a tube diameter slightly smaller than the lumen diameter of the elongate body 1824 when it is coupled end to end. More particularly, a first circular rigid, noncompliant tubular hoop 1850 is inserted into the first lumen 1846 of the elongate body 1824. The first tubular hoop 1850 includes a split that forms open ends 1858 of the first tubular hoop. A second circular rigid, noncompliant tubular hoop 1852 is inserted into the second lumen 1848 of the elongate body 1824. The second tubular hoop 1852 includes a split that forms open ends 1860 of the second tubular hoop.

A first core 1854 may be inserted into the lumen of the first circular rigid, noncompliant tubular hoop 1850 and a second core 1856 may be inserted into the lumen of the second circular rigid, noncompliant tubular hoop 1852. Each of the first and second cores 1854, 1856 may include a first end and a second end to facilitate insertion into the respective lumens of the first and second tubular hoops 1850, 1852. At least one of the first and second cores 1854, 1856 may include a substantially rigid, noncompliant wire or a stranded cable. The first core 1854 is advanced through the lumen of the first rigid, noncompliant tubular hoop 1850 so that the ends of the core are an appropriate distance away from the open ends 1858 thereof (FIG. 96), such as substantially opposite the open ends of the first tubular hoop. The second core 1856 is similarly advanced through the lumen of the second rigid, noncompliant tubular hoop 1852 so that the ends of the core are an appropriate distance away from the open ends 1860 thereof (FIG. 95), such as substantially opposite the open ends of the second tubular hoop. The ends of the first and second cores 1854, 1856 may be positioned about 180° from the open ends of the rigid, noncompliant circularly formed tubular hoops 1850, 1852.

The cores 1854, 1856 stabilize the open ends of the rigid, noncompliant tubular hoops 1850, 1852 within the lumens 1846, 1848 of the outer ring 1814 so that the open ends of the rigid, noncompliant tubular hoops remain substantially constantly aligned as they open and close in response to the rolling action 1836, 1838, 1840 applied to the outer ring. Each of the combinations of the first tubular hoop 1850 with the first core 1854 and second tubular hoop 1852 with the second core 1856 functions as an axle about which the outer ring 1814 may turn for half a rotation, or 180°. More particularly, the first circular tube 1830 of the outer ring 1814 of the wound retractor 1800 may be rolled outside the second circular tube 1832 of the outer ring with the circumference of the first split tubular hoop 1850 in the first circular tube expanding to clear the second split tubular hoop 1852 in the second circular tube. Likewise, the second circular tube 1832 of the outer ring 1814 of the wound retractor 1800 may be rolled outside the first circular tube 1830 of the outer ring with the circumference of the second split tubular hoop 1852 in the second circular tube expanding to clear the first split tubular hoop 1850 in the first circular tube.

Referring to FIGS. 112-116, an outer ring 1814 is shown including an extruded or molded profile 1824 having a first circular tube 1830 and a second circular tube 1832. The outer ring 1814 may include a cross section that resembles the numeral eight (8). The first circular tube 1830 and the second circular tube 1832 are axially spaced from each other and are coupled together through a substantially thin mid-section 1862. The outer ring 1814 includes the first lumen 1846 in the first circular tube 1830 and the second lumen 1848 in the second circular tube 1832. A first rigid, noncompliant tubular hoop 1850 having a split that forms open ends 1858 may be inserted into the first lumen 1846 of the outer ring 1814 and a second rigid, noncompliant tubular hoop 1852 having a split that forms open ends 1860 may be inserted into the second lumen 1848 of the outer ring. A rigid, noncompliant core 1854, 1856, such as a wire hoop or a loop of stranded cable, is inserted into the lumen of each of the rigid, noncompliant tubular hoops 1850, 1852 and advanced until the ends of the respective core are positioned well within the rigid, noncompliant tubular hoops. The first and second cores 1854, 1856 serve to maintain alignment of the two opposed ends of the rigid, noncompliant tubular hoops 1850, 1852. The tubular hoops 1850, 1852 containing cores 1854, 1856 are subsequently advanced to positions well within the lumens 1846, 1848 of the outer ring 1814. More particularly, the first tubular hoop 1850 is oriented such that the open ends 1858 of the first tubular hoop are positioned away from the first and second ends 1842, 1844 of the first circular tube 1830 of the outer ring 1814, such as substantially opposite the first and second ends of the first circular tube. Similarly, the second tubular hoop 1852 is oriented such that the open ends 1860 of the second tubular hoop are positioned away from the first and second ends 1888, 1892 of the second circular tube 1832 of the outer ring 1814, such as substantially opposite the first and second ends of the first circular tube.

Figure 113:
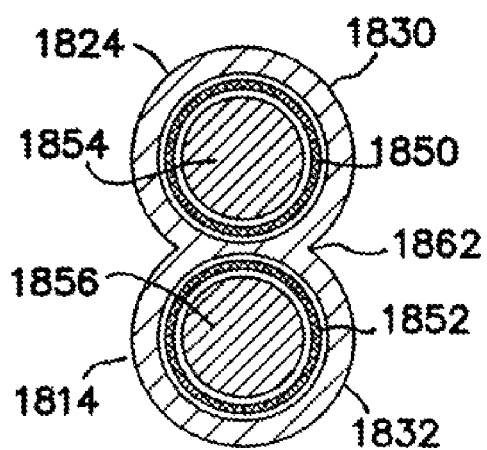
FIG. 113 is a section view of a rigid outer ring having two portions.

Referring to FIG. 113, the outer ring 1814 may include a highly resilient outer portion 1824, a first rigid, noncompliant composite tubular hoop 1850, a second rigid, noncompliant composite tubular hoop 1852, a first core 1854, such as a rigid, noncompliant metallic member and a second core 1856, such as a rigid, noncompliant metallic central member. The rigid, noncompliant tubular hoops 1850, 1852 are sized and configured to maintain a generally circular shape relative to the central axis of the wound retractor 1800 (FIG. 90). In addition, the cores 1854, 1856 within the tubular hoops 1850, 1852 provide additional rigidity and also maintain alignment of the ends 1858, 1860 of the tubular hoops. The rigid, noncompliant composite tubular hoops 1850, 1852 may be made from composites that are well known in the art, such as phenolic, polycarbonate, polyester or other plastics filled with glass fiber, carbon fiber or other well known materials.

Figure 114:
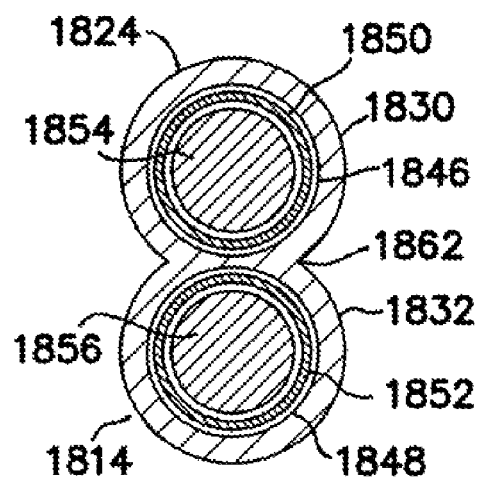
FIG. 114 is a section view of a rigid outer ring having two portions.

Referring to FIG. 114, the outer ring 1814 may include a highly resilient outer portion 1824, a first rigid, noncompliant metallic tubular hoop 1850, a second rigid, noncompliant metallic tubular hoop 1852, a first core 1854, such as a rigid, noncompliant metallic member, and a second core 1856, such as a rigid, noncompliant metallic member. The rigid, noncompliant tubular hoops 1850, 1852 are sized and configured to maintain a generally circular shape relative to the central axis of the wound retractor 1800 (FIG. 90). In addition, the cores 1854, 1856 within the rigid, noncompliant tubular hoops 1850, 1852 provide additional rigidity and also maintain alignment of the ends 1858, 1860 of the central tubular hoops.

Figure 115:
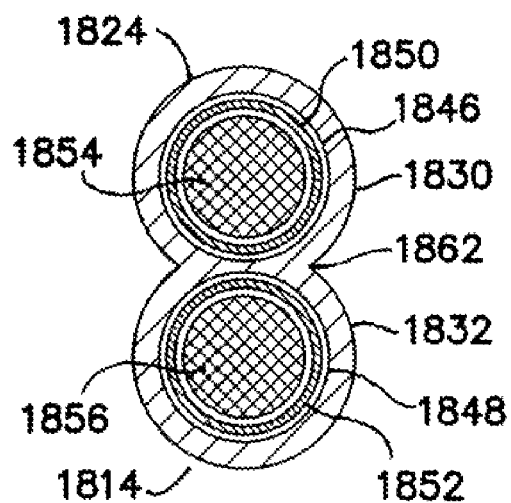
FIG. 115 is a section view of a rigid outer ring having two portions.

Referring to FIG. 115, the outer ring 1814 may include a highly resilient outer portion 1824, a first rigid, noncompliant metallic tubular hoop 1850, a second rigid, noncompliant metallic tubular hoop 1852, a first core 1854, such as a substantially rigid, noncompliant composite member and a second core 1856, such as a substantially rigid, noncompliant composite member. The rigid, noncompliant tubular hoops 1850, 1852 are sized and configured to maintain a generally circular shape relative to the central axis of the wound retractor 1800 (FIG. 90). In addition, the composite cores 1854, 1856 within the rigid, noncompliant tubular hoops 1850, 1852 provide additional rigidity and also maintain alignment of the ends 1858, 1860 of the central tubular hoops. The rigid, noncompliant composite cores 1854, 1856 may be made from composites that are well known in the art, such as phenolic, polycarbonate, polyester or other plastics filled with glass fiber, carbon fiber or other well known materials.

Figure 116:
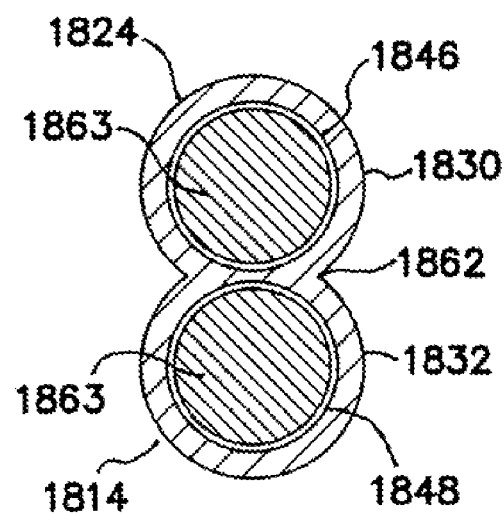
FIG. 116 is a section view of a rigid outer ring having two portions.

Referring to FIG. 116, the outer ring 1814 may include a highly resilient outer portion 1824 and solid hoops 1863 within the lumens 1846, 1848 of the external retention member.

Figure 117:
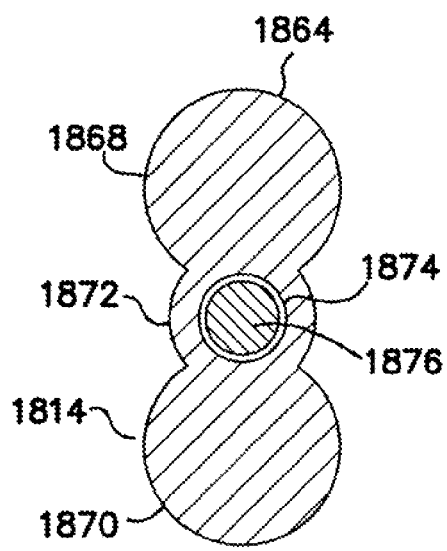
FIG. 117 is a section view of the rigid outer ring having three portions with a single lumen that is positioned in the center portion.

Referring to FIG. 117, the outer ring 1814 may include a highly resilient extruded or molded outer portion 1864 having a first circular tube 1868, a second circular tube 1870 and a third circular tube 1872. The first circular tube 1868 is a large diameter cord. The second circular tube 1870 is a large diameter cord that is separated from the first circular tube 1868 by a third, smaller central circular tube 1872 that has a lumen 1874 therethrough. Alternatively, the three cords or circular tubes 1868, 1870, 1872 may all be substantially the same size. The first, second and third circular tubes 1868, 1870, 1872 are substantially coaxially aligned and each includes a substantially annular axis of substantially equal diameter. The first and second circular tubes or cords 1868, 1870 cooperate to provide a détente or snap-over as the first and second cords are sequentially rolled over the third circular tube 1872. The lumen 1874 of the central, third circular tube portion 1872 is supplied with a rigid, noncompliant hoop 1876 that is constructed from a length of material that has been formed to substantially the diameter of the wound retractor 1800. The rigid, noncompliant hoop 1876 functions as an axle.

Figure 118:
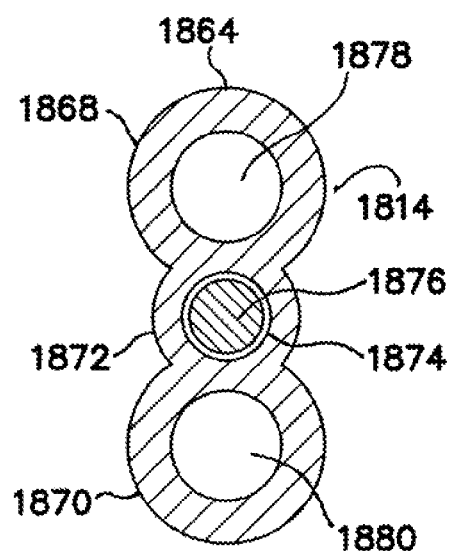

Referring to FIG. 118, the outer ring 1814 may include a moderately resilient extruded or molded outer portion 1864 having a first circular tube 1868, a second circular tube 1870 and a third circular tube 1872. The first circular tube 1868 is a large diameter cord having a lumen 1878 therethrough. The second circular tube 1870 is a large diameter cord having a lumen 1880 therethrough and is separated from the first circular tube 1868 by the third, smaller circular tube 1872 that has a lumen 1874 therethrough. Alternatively, the three circular tubes cords 1868, 1870, 1872 may all be substantially the same size. The first, second and third circular tubes 1868, 1870, 1872 are substantially coaxially aligned and each includes a substantially annular axis of substantially equal diameter. The first and second circular tubes or cords 1868, 1870 cooperate to provide a détente or snap-over as the cords are sequentially rolled over the third circular tube 1872. The lumen 1874 of the third circular tube 1872 is supplied with a rigid, noncompliant hoop 1876 that is constructed from a length of material, such as a metallic material, that has been formed to substantially the diameter of the circular retractor 1800. The rigid, noncompliant hoop 1876 functions as an axle.

Figure 119:
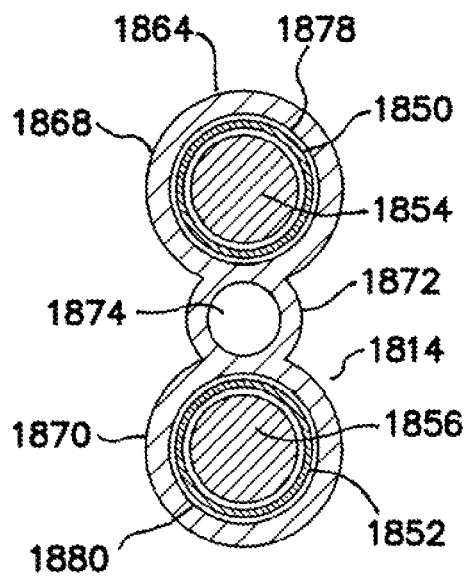

Referring to FIG. 119, the outer ring 1814 may include a highly resilient extruded or molded outer portion 1864 having a first circular tube 1868, a second circular tube 1870 and a third circular tube 1872. The first circular tube 1868 is a large diameter cord having a lumen 1878 therethrough. The second circular tube 1870 is a large diameter cord having a lumen 1880 therethrough and is separated from the first circular tube 1868 by the third, smaller circular tube 1872 that has a lumen 1874 therethrough. Alternatively, the three circular tubes or cords 1868, 1870, 1872 may all be substantially the same size. The first, second and third circular tubes 1868, 1870, 1872 are substantially coaxially aligned and each includes a substantially annular axis of substantially equal diameter. The first and second circular tubes or cords 1868, 1870 cooperate to provide a détente or snap-over as the cords are sequentially rolled over the third circular tube 1872. The lumen 1874 of the third circular tube 1872 is configured to remain hollow and unfilled. The lumens 1878, 1880 of the first and second circular tubes are supplied with rigid metallic first and second tubular hoops 1850, 1852 therein, respectively, that contain rigid, first and second cores 1854, 1856, such as noncompliant circular wires. The hollow third circular tube 1872 provides additional resilience that allows the first and second circular tubes 1868, 1870 to pass through each other.

Figure 120:
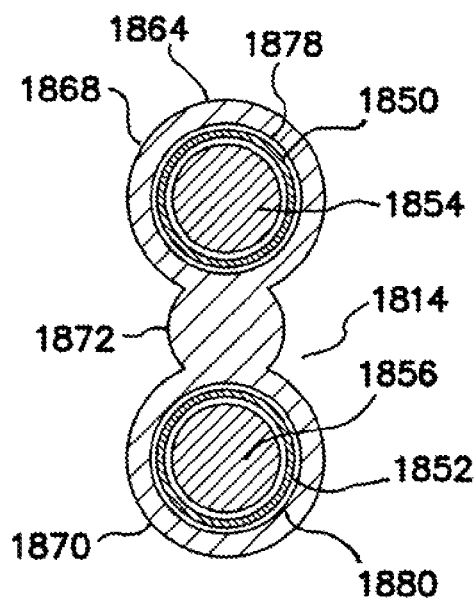

Referring to FIG. 120, the outer ring 1814 may include a highly resilient extruded or molded outer portion 1864 having a first circular tube 1868, a second circular tube 1870 and a third circular tube 1872. The first circular tube 1868 is a large diameter cord having a lumen 1878 therethrough. The second circular tube 1870 is a large diameter cord having a lumen 1880 therethrough and is separated from the first circular tube 1868 by a third, smaller circular tube 1872 that has no lumen therethrough. Alternatively, the three circular tubes or cords 1868, 1870, 1872 may all be substantially the same size. The first, second and third circular tubes 1868, 1870, 1872 are substantially coaxially aligned and each includes a substantially annular axis of substantially equal diameter. The first and second circular tubes or cords 1868, 1870 cooperate to provide a detent or snap-over as the cords are sequentially rolled over the third circular tube 1872. The cord of the third circular tube 1872 is solid. The lumens 1878, 1880 of the first and second circular tubes 1850, 1852 are supplied with rigid, metallic first and second tubular hoops 1850, 1852, respectively, therein that contain cores 1854, 1856, such as rigid, noncompliant circular wires. The solid third circular tube 1872 provides a resilient axle that allows the first circular tube 1868 and the second circular tube 1870 to pass through each other.

Figure 121:
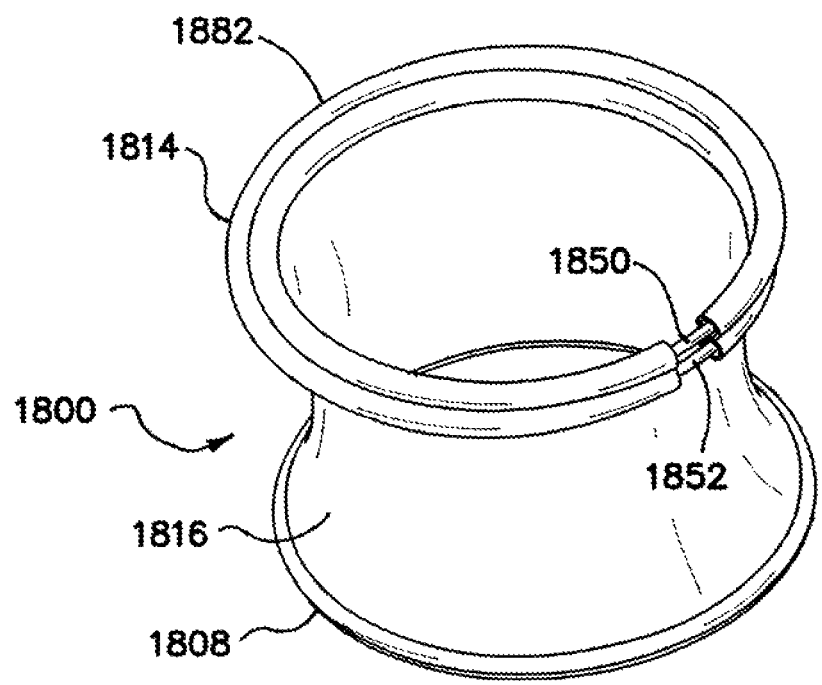
Figure 123:
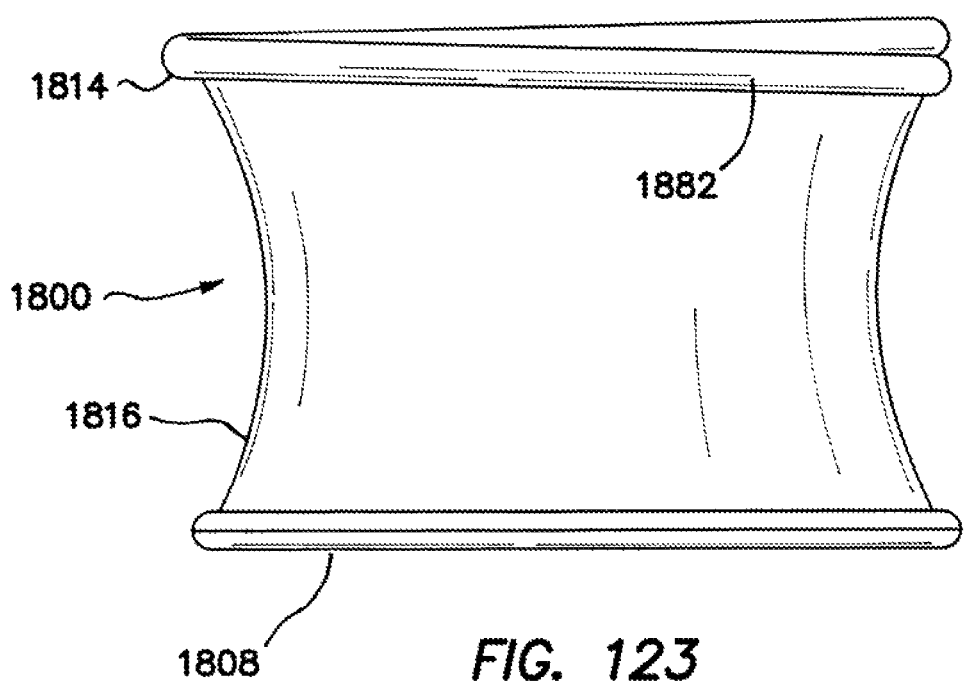
Figure 122:
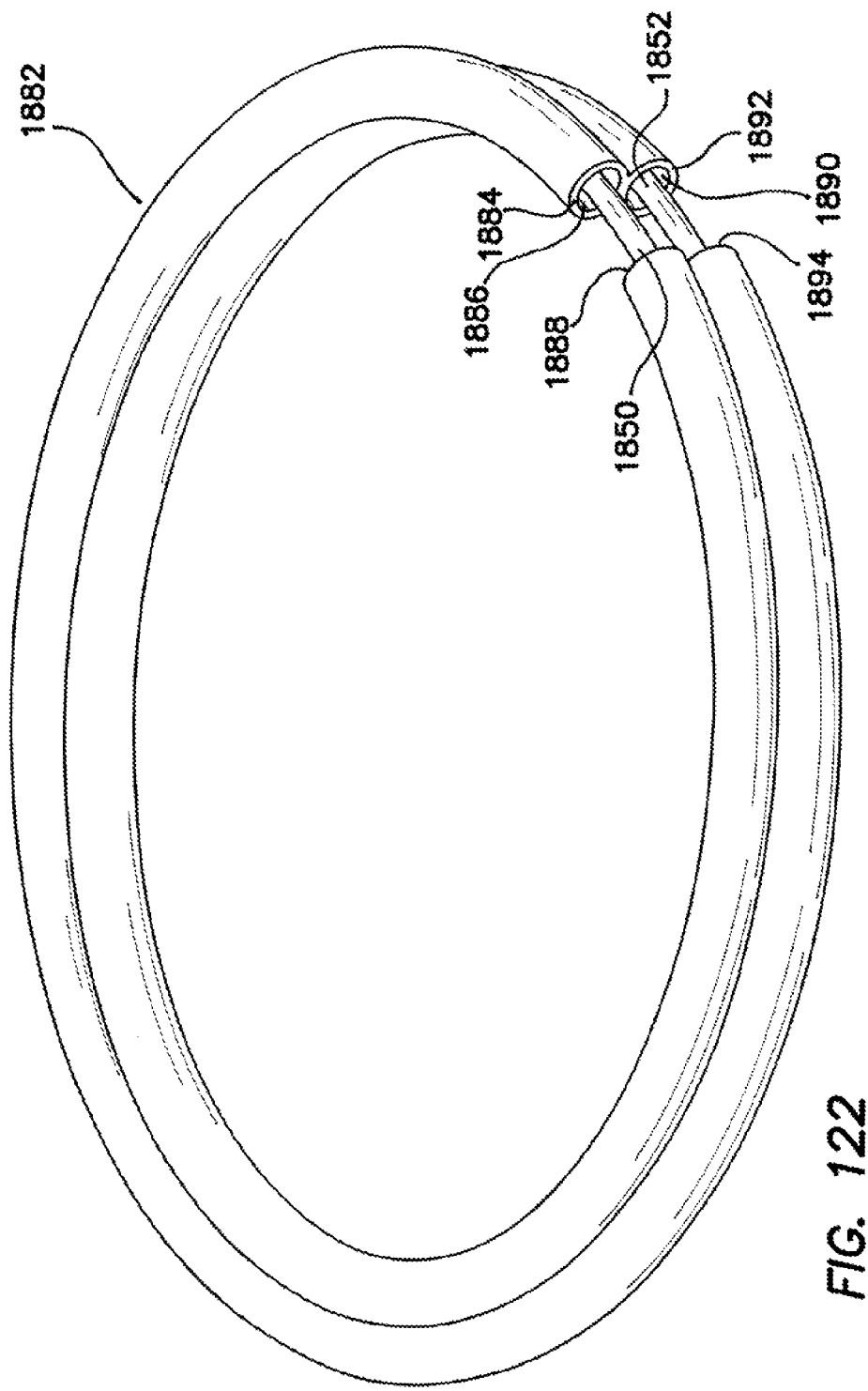

Referring to FIGS. 121-123, the wound retractor 1800 may include a first, inner ring 1808, a second, outer ring 1814, and a sleeve 1816 coupling the inner ring to the outer ring. The inner ring 1808 may be sized and configured to be deformed and placed through the incision 1802 in the body wall 1804 and subsequently into the body cavity 1810. The sleeve 1816 extends through the incision 1802 in the body wall 1804 and is coupled to the second, outer ring 1814 that is sized and configured to be inverted upon itself or rolled to wind the sleeve 1816 upon the second, outer ring. The outer ring 1814 may include a helical rigid, noncompliant element having a shape similar to a Mobius strip. The helical outer ring 1814 may be formed by twisting an extruded or molded element, such as a dual-lumen element 1882, so that the first end 1884 of the first lumen 1886 communicates with the second end 1888 of the second lumen 1890 and the first end 1892 of the second lumen 1890 communicates with the second end 1894 of the first lumen 1886.

The ends 1884, 1888, 1892, 1894 of the extruded or molded form 1814 are not joined together. A first split tubular hoop 1850 is inserted into the first end 1884 of the first lumen 1886 and advanced until it exits the second end 1894 of the first lumen where it is then inserted into the first end 1892 of the second lumen 1890. A first core 1854, such as a rigid, noncompliant wire or a cable may then be inserted into the first tubular hoop 1850 and advanced until the ends of the first core are well within the solid portion of the first tubular hoop, such as substantially opposite the ends 1884, 1886 of the first tubular hoop. The ends of the first core 1854 may be separated from the ends of the first rigid, noncompliant tubular hoop 1850 by about 180°. The first tubular hoop 1850 and first core 1854 are then advanced within the first lumen 1886 of the extruded or molded element to a point distant from the first and second ends 1884, 1888 of the twisted circular form 1814. A second rigid, noncompliant tubular hoop 1852 and a second core 1856 are inserted into the first end 1892 of the second lumen 1890 of the extruded or molded element and advanced as described above. The assembly, which forms an outer ring 1814 in the form of a twisted external rigid, noncompliant outer ring, may be inverted or rolled to wind the sleeve 1816 upon the outer ring. The helical orientation of the rigid, noncompliant outer ring 1814 avoids an extreme detent or snap-over associated with two discrete rigid, noncompliant portions that must pass through each other in a rolling or inverting motion to wind the sleeve 1816 upon the rigid, noncompliant outer ring.

An advantage associated with the modified surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments.

What is claimed is:

1. A wound retractor adapted to retract a surgical incision in a body wall, comprising:
    a first, inner ring adapted to be inserted into the incision and to be juxtaposed with an inner surface of the body wall;
    a second, outer ring adapted for juxtaposition with an outer surface of the body wall, the outer ring comprising three substantially circular tubes, substantially coaxially aligned and coupled together such that the third tube is disposed between the first and second tubes, the first tube having a first lumen and the second tube having a second lumen;
    a first rigid, noncompliant hoop having a split therein, the first hoop being positioned in the first lumen of the first circular tube of the outer ring,
    a second rigid, noncompliant hoop having a split therein, the second hoop being positioned in the second lumen of the second circular tube of the outer ring; and
    a distensible sleeve, the sleeve including a first, distal end and a second, proximal end, the first, distal end of the sleeve being coupled to the inner ring of the wound retractor and the second proximal end of the sleeve being coupled to the outer ring of the wound retractor.

2. The wound retractor of claim 1, wherein the third circular tube includes a third lumen.

3. The wound retractor of claim 2, wherein the hollow third circular tube provides additional resilience that facilitates the passage of the first and second circular tubes through each other.

4. The wound retractor of claim 1, wherein the diameter of the third circular tube is less than the diameter of either the first circular tube or the second circular tube.

5. The wound protector of claim 1, wherein the first and second circular tubes are adapted to provide a detent or snap-over as the first and second circular tubes are sequentially rolled over the third circular tube.

6. The wound retractor of claim 1, wherein the third circular tube is solid.

7. The wound retractor of claim 6, wherein the solid third circular tube functions as a resilient axle about which each of the first and second circular tube may rotate.

8. The wound retractor of claim 1, wherein at least one of the first and second hoops comprises a metallic material.

9. The wound retractor of claim 1, wherein at least one of the first and second hoops comprises a composite material.

10. A wound retractor adapted to retract a surgical incision in a body wall, comprising:
    a first, inner ring adapted to be inserted into the incision and to be juxtaposed with an inner surface of the body wall;
    a second, outer ring adapted for juxtaposition with an outer surface of the body wall, the outer ring comprising three substantially circular tubes, substantially coaxially aligned and coupled together such that the third tube is disposed between the first and second tubes, the third tube having a lumen;
    a rigid, noncompliant hoop having a split therein, the hoop being positioned in the lumen of the third circular tube of the outer ring; and
    a distensible sleeve, the sleeve including a first, distal end and a second, proximal end, the first, distal end of the sleeve being coupled to the inner ring of the wound retractor and the second proximal end of the sleeve being coupled to the outer ring of the wound retractor.

11. The wound retractor of claim 10, wherein the at least one of the first and second circular tubes includes a lumen.

12. The wound retractor of claim 10, wherein the first and second circular tubes are solid.

13. The wound retractor of claim 10, wherein the first and second circular tubes are adapted to provide a detent or snap-over as the first and second circular tubes are sequentially rolled over the third circular tube.

14. The wound retractor of claim 10, wherein the rigid, noncompliant hoop of the third circular tube functions as an axle about which each of the first and second circular tube may rotate.

15. The wound retractor of claim 10, wherein the diameter of the third circular tube is less than the diameter of either the first circular tube or the second circular tube.

16. The wound retractor of claim 10, wherein the three circular tubes are of substantially equal diameter.

* * * * *